(12) United States Patent
Callahan et al.

(10) Patent No.: US 7,949,474 B2
(45) Date of Patent: *May 24, 2011

(54) VISUAL-SERVOING OPTICAL MICROSCOPY

(75) Inventors: Daniel E. Callahan, Martinez, CA (US); Bahram Parvin, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/477,596

(22) Filed: Jun. 3, 2009

(65) Prior Publication Data
US 2009/0285469 A1    Nov. 19, 2009

Related U.S. Application Data

(63) Continuation of application No. 10/296,870, filed as application No. PCT/US01/18382 on Jun. 7, 2001, now Pat. No. 7,546,210.

(60) Provisional application No. 60/210,543, filed on Jun. 8, 2000.

(51) Int. Cl.
*G06F 19/00* (2011.01)
*G01N 31/00* (2006.01)
*G06K 9/00* (2006.01)
*G06K 9/36* (2006.01)

(52) U.S. Cl. ............. 702/19; 702/22; 382/133; 382/286

(58) Field of Classification Search .................. None
See application file for complete search history.

(56) References Cited

U.S. PATENT DOCUMENTS

| | | | |
|---|---|---|---|
| 5,989,835 A | 11/1999 | Dunlay et al. | |
| 6,743,576 B1 | 6/2004 | Sabry | |
| 6,875,578 B2 | 4/2005 | Giuliano | |

FOREIGN PATENT DOCUMENTS

| | | |
|---|---|---|
| FR | 2 764 983 A | 12/1998 |
| FR | 2764983 | 12/1998 |
| WO | 97/45730 | 12/1997 |
| WO | WO 97/45730 | 12/1997 |
| WO | 98/38490 | 9/1998 |
| WO | WO 98/38490 | 9/1998 |
| WO | 98/47006 | 10/1998 |
| WO | WO 98/47006 | 10/1998 |

OTHER PUBLICATIONS

Parvin, et al., Deep View: A Collaborative Framework for Distributed Microscopy (1998), Lawrence Berkeley National Laboratory, Paper LBNL 42150.
McIntosh et al., Medical and Biological Engineering and Computer (1984), May, pp. 259-262.
International Search Report dated Dec. 14, 2001, PCT/US01/18382.
Parvin et al., "Visual Servoing for On-Line Facilities," IEEE Computer Mag., pp. 56-62 (1997).
Potter et al., UltraMicros., 77:153-161 (1999).
Young et al., J. Supercomputer Appl. High Perf. Comput., pp. 171-181 (1996).
Band et al., Cancer Res., 50:7351-7357 (1990).
Ethier et al., Cancer Res. 53:627-635 (1993).
Dairkee et al., Cancer Res. 57:1590-1596 (1995).
Tomida and Tsuruo, Anti-Carec. Drug des. 14:169-177 91999), 1999.
Brown and Giaccia, Cancer Res., 58:1408-1416 (1998).

*Primary Examiner* — Lori A Clow
(74) *Attorney, Agent, or Firm* — Casimir Jones SC

(57) ABSTRACT

The present invention provides methods and devices for the knowledge-based discovery and optimization of differences between cell types. In particular, the present invention provides visual servoing optical microscopy, as well as analysis methods. The present invention provides means for the close monitoring of hundreds of individual, living cells over time; quantification of dynamic physiological responses in multiple channels; real-time digital image segmentation and analysis; intelligent, repetitive computer-applied cell stress and cell stimulation; and the ability to return to the same field of cells for long-term studies and observation. The present invention further provides means to optimize culture conditions for specific subpopulations of cells.

6 Claims, 20 Drawing Sheets

(a)

(b)

Pump_state
    current_time_secs="965701306"
    current_time_usecs="64660"
    pumpnumber="0"
    syringe_0_rate="2.100000"
    syringe_0_rate_units="ml/mn"
    syringe_1_rate="2.700000"
    syringe_1_rate_units="ml/mn"
    syringe_0_diameter="26.000000"
    syringe_1_diameter="26.000000"
    running_or_stopped="Stopped"
    mode="Proportional"
    direction="Parallel"

Pump_state
    current_time_secs="965701306"
    current_time_usecs="374190"
    pumpnumber="1"
    syringe_0_rate="2.300000"
    syringe_0_rate_units="ml/mn"
    syringe_1_rate="0.000000"
    syringe_1_rate_units="ml/mn"
    syringe_0_diameter="27.000000"
    syringe_1_diameter="25.000000"
    running_or_stopped="Stopped"

FIG. 14 B

```xml
<StackAcquisition
SINGLE_or_MULTIPLE_stack_acquisition="MULTIPLE"
seconds_interval_between_multiple_stacks="300"
TOTAL_TIME_or_NUM_STACKS_to_stop_multiple_stack_acquisition="TOTAL_TIME"
total_time_seconds_then_stop="7200"
num_stacks_then_stop="1" >

<Channel
        filterWheelPosition="0"
        headerInfo_wavelength="360nm"
        headerInfo_filenameChannelChar="0"
        description="H42"
        ACTIVE="yes"
        >
        <exposureTime_ms> 200</exposureTime_ms>
        </Channel>

<Channel
    filterWheelPosition="1"
    headerInfo_wavelength="490nm"
    headerInfo_filenameChannelChar="1"
    description="null"
    ACTIVE="yes">
        <exposureTime_ms> 1000</exposureTime_ms>
        </Channel>
<Channel
    filterWheelPosition="2"
    headerInfo_wavelength="570nm"
    headerInfo_filenameChannelChar="2"
    description="null"
    ACTIVE="yes">

<exposureTime_ms> 1000</exposureTime_ms>
</Channel>
<Channel
    filterWheelPosition="3"
    headerInfo_wavelength="380nm"
    headerInfo_filenameChannelChar="3"
    description="null"
    ACTIVE="yes">

<exposureTime_ms> 500</exposureTime_ms>
</Channel>
<Channel
    filterWheelPosition="4"
    headerInfo_wavelength="340nm"
    headerInfo_filenameChannelChar="4"
    description="null"
    ACTIVE="yes">

<exposureTime_ms> 500</exposureTime_ms>
</Channel>
<Channel
    filterWheelPosition="5"
    headerInfo_wavelength="OPEN"
    headerInfo_filenameChannelChar="5"
    description="null"
    ACTIVE="no">

<exposureTime_ms> 100</exposureTime_ms>
</Channel>

<Channel
    filterWheelPosition="6"
    headerInfo_wavelength="TRANS"
    headerInfo_filenameChannelChar="X"
    description="brightfield"
    ACTIVE="yes">
```

FIG. 14 C

```
ics_version       1.0
filename          dc051300dc.01.1
layout    parameters 4
layout    order      bits          x            y            z
layout    sizes      16            1024         1024         5
layout    coordinates              video
layout    significant_bits         16
representation    format           integer
representation    sign             signed
representation    compression                   compress
representation    byte_order 2                  1
representation    SCIL_TYPE                     g3d
parameter         origin      0    160          6            0
parameter         scale       1    0.68000001   0.68000001            0
parameter         labels      intensity   x-pos        y-pos        probe
parameter         units       relative    microns      microns      undefined
parameter         exptype     beads
parameter         exptarget   other
parameter         probe       dapi_360    fitc_490     tr_570       fura2_380    fura2_340
parameter         target      other       other        other        other        other
parameter         exposure_time           1.00         1.00         1.00         1.00         1.00
history   date        Sat May 13 23:50:22 2000
history   computer    Sun_Sparc_Ultra_170
history   laboratory  LBNL_Life_Sciences_Division
history   operator    Daniel E Callahan
history   microscope              Zeiss_Axiovert135TV
history   objective   Zeiss_Fluar_10x 0.50NA
history   camera      /dev/sdv0
history   software    SCIL-Image_1.3
history   comments    New Xe lamp, base mounted camera
```

FIG. 14 D

VISUAL-SERVOING OPTICAL MICROSCOPY

CROSS-REFERENCE TO RELATED APPLICATIONS

The present application is a continuation of U.S. patent application Ser. No. 10/296,870, filed Jun. 26, 2003, now U.S. Pat. No. 7,546,210, which is a 371 U.S. national stage entry of expired International Patent Application No. PCT/US01/18382, filed Jun. 7, 2001, which claims the benefit of expired U.S. Provisional Application No. 60/210,543, filed Jun. 8, 2000, all of which are herein incorporated by reference in their entireties.

STATEMENT REGARDING FEDERALLY SPONSORED RESEARCH OR DEVELOPMENT

This invention was made with government support under Grant No. DE-AC03-76SF00098, awarded by the Department of Energy. The Government has certain rights in the invention.

FIELD OF THE INVENTION

The present invention provides methods and devices for the knowledge-based discovery and optimization of differences between cell types. In particular, the present invention provides visual servoing optical microscopy, as well as analysis methods. The present invention further provides means to optimize culture conditions for specific subpopulations of cells.

BACKGROUND OF THE INVENTION

The current trend in telepresence research is to bring experts and facilities together from geographically dispersed locations (Hadida-Hassan et al., J. Struct. Biol., 125:229-234 [1999]; Parvin et al., "Visual Servoing for On-Line Facilities," IEEE Computer Mag., pages 56-62 [1997]; Potter et al, UltraMicros., 77:153-161 [1999]; Young et al., J. Supercomputer Appl. High Perf. Comput, pp. 170-181 [1996]; and Parvin et al., "A Collaborative Framework for Distributed Microscopy," IEEE Conf. on SuperComputing [1998]). This system, in addition to collaborative frameworks (Parvin et al., [1997], supra) is commonly used in the field. Telepresence research has focused on remote functionality of the instrument and necessary automation for large-scale data collection and analysis. The MASH project of the University of California, at Berkeley (McCanne, IEEE Internet Comput., 3:33-44 [1999]) uses MBone tools in a heterogeneous environment to develop scalable multi-media architecture for collaborative applications in fully distributed systems. NCSA's Habenero project provides smooth management and simultaneous distribution of shared information to all clients in a component-based centralized system that is primarily written in Java. Rutger University's DISCIPLE uses a CORBA framework for distributed access in a service-based, centralized system for enforcing shared virtual space. Sun Microsystem's Java Shared Development tool kit provides collaborative-aware Java code to send data to participants within a communication session. It supports three types of transport protocols, namely TCP/IP socket, light-weight reliable multicast, and remote invocation methods. In this framework, all objects are manageable and collaboration occurs within a session that includes channel, token, blobs, and listener. The University of Michigan's Upper Atmosphere Research Collaboratory (UARC) is a web-based distributed system that is mostly written in Java. This system collects data from over 40 observational platforms for space physics research for both synchronous and asynchronous collaboration. In this system, data suppliers publish their data on a data-dissemination server. Clients then subscribe, in order to receive the desired information.

In addition to the physical sciences, telepresence methods have been used in the biological sciences. For example, in the post-genomic sequencing era, quantitative imaging of complex biological materials is a critical problem. Indeed, sequential measurements obtained with different microscopy techniques preclude detailed analysis of multidimensional responses (e.g., in time and space). Quantification of spatial and temporal concurrent behavior of multiple markers in large populations of multicellular aggregates is hampered by labor intensive methods, a lack of quantitative tools, and the inability to index information. Ideally, methods would track the kinetics and quantities of multiple target proteins, their cellular context and morphological features in three-dimensions using large populations.

For example, there are several thousand antibodies and other reagents available for differentiating specific protein components of cells. Some antibodies can additionally discriminate between functional variants of proteins caused by modifications such as phosphorylation status, protein conformation, and complex formation. Of the intracellular proteins, a large number are involved in signalling pathways. These pathways are currently not well understood, due to the complexity of the potential events, the potential for multiple modifications affecting protein function, and lack of information regarding where and when a protein is actively participating in signalling. Inherent biological variability and genomic instability are additional factors that support the requirement for large population analysis. Thus, there is a need for microscopy and image analysis methods that are useful for developing a more detailed picture of cellular signalling. This is particularly true in the development of methods to diagnose and treat disease.

Today, various diseases are now understood at the molecular and genetic level. Analysis of molecules associated with disease is important for disease diagnosis and prognosis. However, the study of diseases such as cancer is currently limited by the techniques and model systems available for their characterization. Studies for the qualitative or quantitative analysis of protein and/or nucleic acid expression are compromised by the diverse cell populations in tissue samples which typically include a number of cell types (e.g., abnormal cells, epithelial cells, stromal cells, endothelial cells, inflammatory cells, etc.). Since the cells of interest (e.g., tumor cells) are often a relatively small percentage of the total cell population, it is difficult to interpret the significance of net protein or nucleic acid alterations in the typical specimen. In addition, studies of cells in culture do not account for the complex interactions that occur between cells. Furthermore, commonly used techniques rely on methods such as tissue fixation, antigen-antibody recognition, and/or histological stains that typically require that the cells analyzed be killed during the processing of the samples. This limits the amount of information available regarding the cells in the specimen.

The use of tools such as fluorescent probes and confocal microscopy have enabled the resolution of three dimensional intracellular spatial distribution of various molecular species and subcellular structures, as research in cellular physiology require the formation of theoretical hypotheses regarding experimentally observed phenomena. These hypotheses are then often formalized into mathematical models. These models are then incorporated in simulations, in an attempt to correlate experimental results with phenomena observed in vivo.

However, there are deficiencies in the existing technologies. In general, these deficiencies originate from the current limitations regarding the representation of cells. In these methods, cells are represented as ideal and simple geometric shapes with spatially homogenous behavior (i.e., physiology) and structure (i.e., anatomy). This prevents the researcher from actually expressing an observed physiological phenomena in a simulation that easily correlates to an actual experiment using an intact cell. Thus, the validation of the model and hypothesis is often very difficult.

Most current efforts in the modeling and simulation of cellular physiology are directed toward either very specific models of individual mechanisms or abstract representations of more complex phenomena. The specific models include models of individual molecular interactions (e.g., involving ion channels). The abstract models typically apply simplifications of the underlying mechanisms that are usually only appropriate to explain a limited class of physiological problems and/or observations. Thus, methods and devices are needed that facilitate real-time observations, correlations of observed phenomena with disease conditions, and means to observe cells in situ over time.

In addition, for some types of cancer (e.g., certain leukemias and testicular cancer), chemotherapy is successful in providing a cure to affected patients. However, in solid tumors (e.g., breast cancer), little progress has been made in improving therapy. Inherent or acquired multi-drug resistance (MDR) in solid tumors represents one important obstacle in providing cures via chemotherapy. In vitro chemosensitivity assays to assess drug response and predict patient response have been in development for over 40 years, but a truly successful in vitro chemosensitivity test has not been developed. Thus, there remains a need for reliable and meaningful in vitro chemosensitivity tests.

SUMMARY OF THE INVENTION

The present invention provides methods and devices for the knowledge-based discovery and optimization of differences between cell types. In particular, the present invention provides visual servoing optical microscopy, as well as analysis methods. The present invention provides means for the close monitoring of hundreds of individual, living cells over time; quantification of dynamic physiological responses in multiple channels; real-time digital image segmentation and analysis; intelligent, repetitive computer-applied cell stress and cell stimulation; and the ability to return to the same field of cells for long-term studies and observation. The present invention further provides means to optimize culture conditions for specific subpopulations of cells.

In particular, the present invention provides means for the automated detection and segmentation of a field of cells contained within a cell array, and computing the cells' responses to various stimuli as a function of computer control and external exposure, particularly for population studies. External exposure is controlled with flow of compounds that reside in computer-controlled syringes (or other suitable receptacles) positioned near the optical device (e.g., a microscope).

In preferred embodiments, VSOM provides means for structural delineation of specific sub-compartments of each cell at each selected field of view. The field of view is positioned by the user by means of the xy stage. In addition, VSOM provides means to measure responses at specific subcellular compartments for each cell in the field of view. In some embodiments, a sub-cellular response is measured at a) a programmed excitation frequency, and b) as a function of cell exposure to compounds that are being injected into the cell array. In addition, the present invention provides control of a servo-loop for adjusting the exposure of the cells of interest as a function of measured responses. The present invention provides maximum flexibility. For example, in some embodiments, the external exposure is shut off when the average response for the cells and/or subcellular compartments for all cells of interest in a field of view achieves a user-defined threshold. In alternative embodiments, the external exposure is shut off when a desired percentage of cells and/or their subcellular compartments reaches a defined threshold. In still further embodiments, the external exposure is shut of when the average response for a subset of cells and/or a subset of subcellular compartments achieves a certain profile. Each of these alternatives can be repeated as many times as desired in any combination desired.

Prior to the development of the present invention, it was technically difficult to digitally image large numbers of single living cells under a microscope. It was also difficult to simultaneously monitor multiple physiological responses in large numbers of single, living cells for an extended period of time without harming the cells. The first limitation existed largely because of the limited field of view at any given magnification. The field of view was further restricted by the limited size and resolution of the solid-state digital imaging device (i.e., charge-coupled device; CCD) inside the digital camera used. The present invention overcomes these limitations by facilitating the rapid, automatic, and repetitive monitoring of multiple fields of view (i.e., larger numbers of cells) by software control of an x,y,z microscope stage. The present invention also facilitates the simultaneous remote control of multiple microscopes from a central computer. Indeed, the present invention overcomes the memory, software, and processing resource limitations associated with presently used computers (i.e., clients) that control local microscope peripherals (e.g., scanning stages, filter wheels, perfusion pumps, robotic arms, shutters, cameras, etc.). The present invention allows VSOM to be performed by remote control using the internet, and a more powerful central computer (the server) located at a geographical location distant from the remote user(s). The server performs or distributes the more processing intensive tasks and serves as a central location for a very large database of current and previous cellular responses. Thus, the VSOM of the present invention takes advantage of the benefits derived from network access to a powerful central server and a large central database of previously observed single cell responses with previously observed correlations across multiple channels of information. In particularly preferred embodiments, the VSOM system repeatedly detects cells, logs and analyzes all of the observed cell responses across all channels, compares current cell responses, makes correlations across current channels of information, and consults a database of previously observed cell responses and previously observed correlations across different channels of information. Then, during the course of a single experiment, the system makes a series of knowledge-based decisions on how to adjust experimental parameters, in order to achieve the objective of the current experiment.

Thus, the present invention allows multiple, complete experimental cycles during the course of a single relatively short experiment. This greatly accelerates the process of searching for, discovering, and optimizing differences between different cell types. Relatively low numbers of cells are required, and because individual cell responses are monitored, specimens submitted for analysis may contain different types of cells. "Cell type" is a classification achieved by any observation that can separate a group of cells into multiple groups of cells, where each cell within a group has similar properties that distinguish it from cells in another group. This classification is typically based on repeated observation of relatively rapid physiological responses at the individual, single-cell level (e.g., observations of subcellular components, changes in morphology, cell division, cell death, detachment, etc.). However, the term also encompasses various cell types differentiated based on traditional histological criteria (e.g., epithelial cells, tumor cells, myocytes, adipocytes, nerve cells, etc.).

For large numbers of cells, the ability to rapidly make automated, knowledge-based decisions on how to alter experimental parameters during the course of an experiment was not available prior to the development of the present invention. The ability provided by the present invention to perform many "test/store/analyze/learn/re-design/re-test" cycles during the course of an experiment makes many experiments and applications possible that previously were unfeasible. When cells remain viable and an experiment remains in progress and on-line, correlations between past and future responses to stimuli are maintained on a cell-by-cell basis. Various and repeated computer-generated stimuli can be applied and repeated during a single experiment, using a relatively small sample of cells. This provides a tremendous advantage when searching for and optimizing differences between cell types. The term "stimulus" refers to single, repeated or continuous application of a stimulus, stimuli, or combination of stimuli. Stimuli that generate physiological responses encompass mechanical, physical, chemical, and biological entities. Thus, it is not intended that the present invention be limited to any stimulus or type of stimulus.

Living cells can move or change shape. Therefore, it is important to provide means to analyze the morphometric, texture, and other properties of the cells. Thus, when returning to a given field of view, the software must adjust focus (z-axis control), and must make small horizontal and vertical adjustments to reacquire and re-register the field of view (x,y axis control). In addition, the original contours defining the outline of the individual cells must be modified in order to track changes in cell position and shape. Thus, in one embodiment, the VSOM of the present invention provide means to make decisions regarding control of the instrument based on analysis of image content. Indeed, the present invention provides means for: computer automation of repeated and/or continuous application of stimuli (or a stimulus) to living cells; repeated and/or continuous detection and monitoring of one or more cellular or subcellular physiological responses to the stimuli at the single cell level, using microscopy and digital imaging; rapid observation of a sufficient number of individual cell responses to establish criteria suitable for reliable identification of cell type(s) and/or modification of the stimuli in order to optimize differences between cell types; rapid analysis of current and previously stored (e.g., database information) cell responses so that knowledge-based stimulus control decisions can be made while cells are available for observation and/or stimulation; and monitoring of the correlations between time-dependent events across multiple channels.

The present invention further provides means to define the contours of living cells using transmitted light in addition to fluorescence emission light. This facilitates the tracking of cells that do not contain a fluorescent compound. In addition, this allows the use of smaller amounts of potentially cytotoxic fluorescent labeling compounds and avoids the intense fluorescence excitation illumination required to stimulate fluorescence emission. Thus, cells can be observed for longer periods of time. Furthermore, cells with specific behaviors can be individually retrieved at the end of the experiment for pooling, establishment of cell lines, cloning, propagation towards a given differentiated state, analysis, etc.

In addition to monitoring a larger number of cells, the present invention allows a larger number of physiological responses to be observed during a single experiment because the instrument can observe different physiological responses in different channels essentially simultaneously, by rapidly cycling the imaging from transmitted light to fluorescence emission light of different wavelengths.

On-going fluorescence signals from an entire population of living cells can be detected using a multiwell fluorescence plate reader. However, single cell responses cannot be observed. Nonetheless, one embodiment of the VSOM of the present invention provides for the discovery and optimization of fluorescence assays that are suitable for multiwell plate readers. Furthermore, using common techniques, multi-channel fluorescence signals from individual living cells can be detected at a single instant using flow cytometry. The cells can be sorted according to fluorescence signal and can also be recovered. However, the cells flow rapidly past a detector and a single (perhaps multichannel) measurement is taken. Individual cells are not tracked for any length of time and repeated observations of the same cell, with correlations between past and present responses is not possible. The present invention overcomes these limitations and facilitates the development and optimization of fluorescence assays that are suitable for flow cytometry and activated cell sorting.

The present invention finds use in cell-type specific fluorescence assays that are useful for any types of cells (e.g., animal, plant, microorganisms, etc.). Thus, it is not intended that the present invention be limited to any type of cells or any particular fluorescence or other assay system. While preferred embodiments involve human cells, other embodiments involve cells obtained from other mammals, as well as plants, and other organisms. For example, the present invention provides means for the detection and discrimination between normal, pre-malignant, malignant, and/or multi-drug resistant cancer cells obtained from tissue (e.g., biopsies, surgical removal of tissue, etc.). In addition, the present invention provides means for the design of protocols that selectively label rare cell types (e.g., stem cells or fetal cells in maternal blood). In some embodiments, these protocols are modified for use with radioactive and other label systems. The present invention also facilitates design and application of assays to establish a chemotherapeutic regimen (including a combination of drugs), that is tailored to an individual patient and/or an individual tumor within a patient. In addition, the present invention provides assays useful for screening large numbers of potential drug, insecticide, herbicide, and other compounds for numerous uses in medicine, agriculture, biotechnology, etc. The present invention further provides assays useful for screening large numbers of potential agents for use in cell proliferation, cytotoxicity and/or differentiation.

The present invention further provides means to design in vitro tissue culture conditions that lead to the proliferation of a specific cell type, either by giving a growth advantage to the cell type of interest, or by designing environmental conditions or protocols that are cytotoxic to other cell types present in the culture. Thus, the present invention provides means to cultivate cells that are often difficult to grow in vitro. In addition, the present invention provides means to produce cell culture conditions that are suitable for guiding cells to a specific differentiated end-point. For example, using the present invention, conditions necessary to guide stem cells or embryonic cells to a final desired end point can be developed.

The present invention also finds use in the development and performance of various types of rapid in vitro tests. For example, if several potential tissue or bone marrow donors exist for a particular patient, the various donors' cells are mixed with the patient's immune cells and observations of any immune rejection response are made on the single cell level. Thus, identification of the best donor for that particular patient is facilitated. In addition, these tests are performed in the presence of drugs (or drug candidates) designed to suppress transplant rejection, facilitating the choice of the optimum anti-rejection drug treatment regimen (i.e., single drug or multiple drugs in combination), as well as the best donor for the patient.

The present invention provides methods comprising receiving cellular image data (i.e., information regarding the physiology, morphology, and/or other characteristics of a cell or cells) from a detection device that monitors cells or subcellular components of the cells; analyzing the cellular image data; and automatically actuating a plurality of stimulating devices adapted to stimulate the cells or subcellular components in response to the analyzed cellular image data. In some embodiments, the present invention further comprises automatically and independently actuating the plurality of stimulating devices to stimulate the cells in response to the analyzed cellular image data. In still further embodiments, the analyzing the cellular image data comprises at least one of analyzing the size of the cells, analyzing the color of the cells, and analyzing the motion of the cells. In some preferred embodiments, the detection device comprises a visual servoing optical microscope (VSOM), and wherein the method further comprises monitoring the cells using the VSOM. In alternative embodiments, the stimulating devices are syringes. In still further embodiments, the methods further comprise the step of storing the cellular image data as a function of time. In some particularly preferred embodiments, the cells are living and the subcellular components are in living cells. In additional embodiments, the methods further comprise repeating the above described steps as often as desired and in any order desired.

The present invention also provides methods and systems for analyzing a cell array comprising a cell array, an optical system detecting light from a cell array and providing a first signal corresponding to light produced by a cell array, to a computer receiving the first signal and using the first signal to generate a second signal controlling the delivery of at least one test stimulus to the cell array to produce a stimulated cell array, and a robotic system receiving the second signal and delivering the test stimulus, wherein the optical system further detects light emitted from the stimulated cell array. In some embodiments, the test stimulus is automatically applied to the cell array according to the first signal. In some preferred embodiments, the robotic system delivers the test stimulus to the cell array through at least two microfluidic channels. In still further embodiments, the optical system comprises at least one microscope. In some preferred embodiments, the microscope is a confocal microscope, while in other embodiments, the microscope is a fluorescence microscopes. In some embodiments, the cell array comprises at least two cell types. In additional embodiments, the optical system scans the cell array to detect subcellular components within the cell types contained in the cell array. In some preferred embodiments, the subcellular components are selected from the group consisting of nuclei, nucleoli, mitochondria, lysosomes, phagolysosomes, and storage vesicles. In some particularly preferred embodiments, at least one subcellular component is labelled. In alternative preferred embodiments, the subcellular component is labelled by the test stimulus. In some embodiments, the subcellular component is labelled with at least one compound selected from the group consisting of fluorescent dyes, radioactive compounds, enzymes, and vital dyes. In additional embodiments, the optical system converts the label into digital data. In still further embodiments, the robotic system utilizes the digital data to automatically adjust the delivery of the biologically active ingredient to the cell array. In other embodiments, the present invention provides a means for remote operation of the computer system. In still further embodiments, the present invention provides means to compare cellular information (e.g., in a profile of results) with a reference database comprising previously obtained cellular information and data.

The present invention also provides a computer readable medium comprising: code for receiving cellular image data from a detection device that monitors cells or subcellular components; code for analyzing the cellular image data; and code for automatically adjusting a plurality of stimulating devices adapted to stimulate the cells or subcellular components in response to the analyzed cellular image data. In some preferred embodiments, the computer readable medium further comprises code for controlling a visual servoing optical microscope (VSOM) monitoring the cells. In still further embodiments, the computer readable medium further comprises at least one of code for analyzing the size of the cells, code for analyzing the color of the cells, and code for analyzing the motion of the cells. In yet additional embodiments, the computer readable medium further comprises code for automatically and independently actuating the plurality of stimulating devices to stimulate the cells in response to the analyzed cellular image data. In additional embodiments, the stimulating devices are syringes. In some preferred embodiments, the computer readable medium further comprises code for storing the cellular image data as a function of time. In additional preferred embodiments, the cells are living and the subcellular components are in living cells.

GENERAL DESCRIPTION OF THE INVENTION

Figure 1:
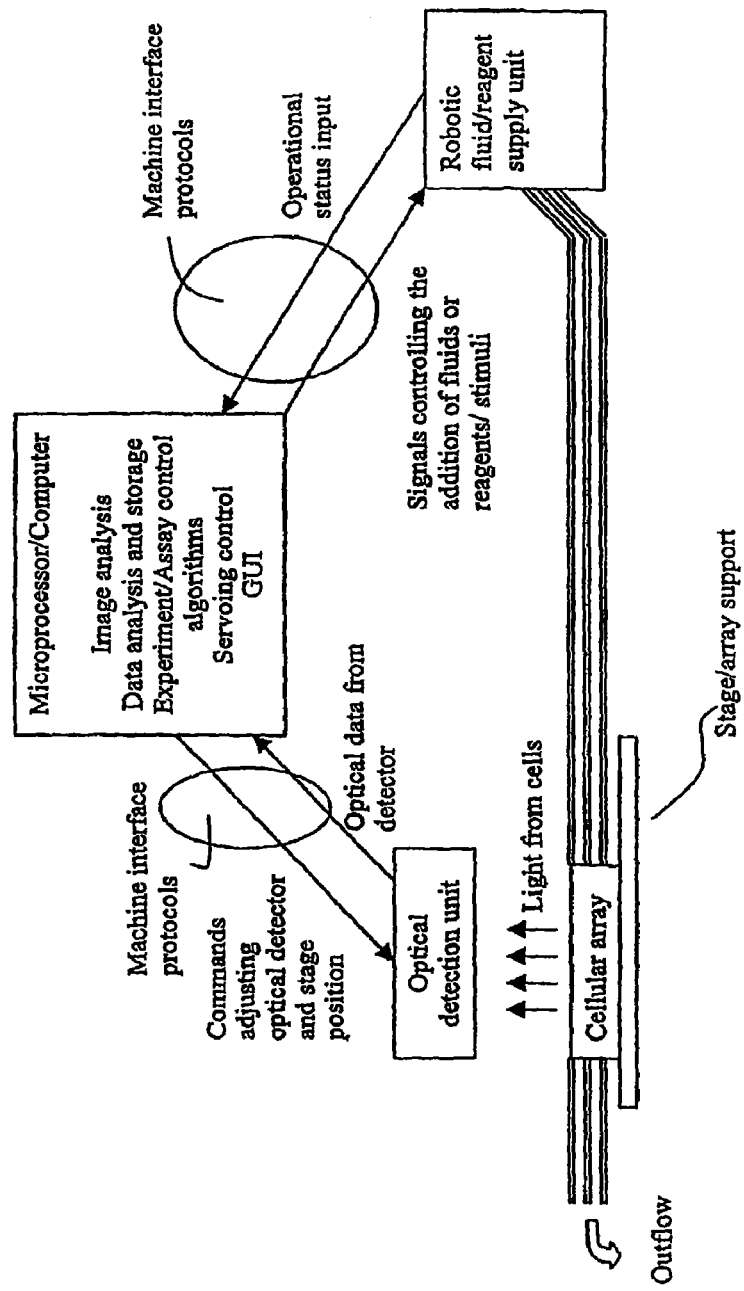
FIG. 1 provides a schematic showing the relationship between the microprocessor/computer, robotics, and optical system of the present invention, as well as other components of the system.

The present invention provides means to couple the processing, storage, and analysis power of the most modern, networked computers with the complex, interacting biological and biochemical pathways or "circuitry" of a single living cell. Moreover, this process can take place repeatedly on hundreds or thousands of cells, and human beings are not part of this coupled and automated system. A communication, or feedback loop, is established as living cells, interrogated via computer applied stimulations and perturbations, "respond" in a manner that can be detected and analyzed by the computer. These complex, computer applied stimulations and perturbations can be applied repeatedly and can be adaptively altered based on the complex "responses" received from the cells.

Some embodiments of the present invention find use in the rapid discovery of subtle differences in the net physiological responses of different cell "types," and/or between cells of the same "type" that are in different physiological states. The present invention provides means to rapidly, automatically, and efficiently refine or optimize the net differential responses of different cell types by applying a series of additional tests, or stimulations that are designed to isolate or localize observed differences to particular biochemical pathways or to the expression of a particular gene or set of genes, or to other specific differences. In this manner, subtle differences between the biological responses of two or more distinct populations of complex, living systems (individual cells) can be amplified as the particular difference is identified and targeted in an increasingly precise manner.

The present invention provides methods and devices for the knowledge-based discovery and optimization of differences between cell types. In particular, the present invention provides visual servoing optical microscopy (VSOM) and analysis methods for the automated generation of, and the subsequent automated analysis of, large defined arrays of living cells. The present invention further provides means to search for, quantify, and optimize, differential responses of cells to applied stimuli or combinations of stimuli. The present invention can, in an automated fashion, exploit previously known differences in cell responses, and/or search for and discover new differences in cell responses in order to achieve a variety of objectives. Thus, the present invention provides for both the discovery of, and the application of stimuli, or combinations of stimuli, that produce a desired differential cell response.

The present invention further provides for identification of individual cell type and individual cell physiological status for large numbers of individual cells attached to or firmly sitting on a surface. Concomitant with this individual cell identification is the specification of cell position relative to a large number of neighboring cells. In this manner, a large array of living cells that have been arbitrarily deposited on a surface are, in an automated fashion, transformed into a large array of identified cells at defined x,y,z locations. Such arrays are then monitored and tracked during subsequent VSOM stimulation, perturbation, and interrogation experiments. VSOM stimulations, perturbations, and interrogations include the application of fluorescent probes, the application of chemical and biological agents, and the application of physical stimuli. These that are applied alone or in combination at doses, at intervals, and in sequences that are automatically recorded, analyzed, and optimized. Such stimulations, perturbations, and interrogations may be benign, they may result in the application of lethal stresses on the cells, or they may have some intermediate effect on the cells. The present invention allows the biological consequences of physiological responses to automatically applied stimulations, perturbations, and interrogations to be quantified, monitored, stored, and correlated with other responses, during the course of one experiment, for long periods of time on a cell by cell basis, and on an organelle by organelle basis.

A history of the applied stimuli, perturbations, and interrogations and a history of the multiple, correlated individual cell responses of hundreds or thousands of cells observed simultaneously in multiple channels is stored in a remote or local database. In addition, the ultimate biological consequence of such stimulations are collected for future VSOM experiments. As this database grows, VSOM assays and protocols gain greater predictive power and become more useful for instrument and process control and optimization.

The present invention provides for real-time, local or remote access to a database during the course of VSOM experiments so that stimuli, searches, optimizations, and VSOM instrument control can be based on knowledge of previous cell responses to applied probes, stimuli, perturbations, and interrogations. The present invention provides for the development of a variety of in vitro and in vivo assays that are specific for cell-type and/or cell-physiological status. The development of assays based on the methods and system of the present invention and the accumulation of stored knowledge allows for more rapid, benign, and specific assays that can be used for the automated generation of large, well-characterized living cell arrays. This provides for a virtuous cycle whereby minimally stimulated or perturbed living cell arrays can be rapidly and automatically generated and subsequently used during VSOM searches for new or improved recipes and protocols that exploit differences between cell types. This process and instrument control knowledge, and the resulting recipes and protocols that produce cell-type specific physiological responses and cell-type specific biological consequences can then be used in both VSOM and non-VSOM situations in order to achieve a variety of objectives.

These objectives include, but are not limited to (i) the rapid, automated optimization of in vitro culture conditions and protocols favorable only to specific subpopulations of cells, (ii) the development of cell-type specific assays, protocols, and diagnostic kits suitable for non-VSOM instruments or situations, (iii) the development of cell-type specific assays suitable only for VSOM instruments, (iv) the discovery of specific differences between cell types that result in targets for drug development, (v) the discovery of in vitro conditions and protocols that result in production of cells in a desired differentiated state, as in the production of different, specific types of cells from stem cells, (vi) the discovery of the function of a specific gene or set of genes within the complex, interacting biochemical networks of a living cell, (vii) the discovery of the relationship between the expression or non-expression of a gene or set of genes, and the resulting cellular phenotype, (viii) the discovery of the effect or effects of drugs or other agents within the complex, interacting biochemical networks of individual living cells, (ix) the discovery of agents and protocols suitable for cell specific delivery of drugs or probes, (x) the discovery of chemotherapeutic regimes designed for an individual patient tumors, especially those which may exhibit multidrug resistance, (xi) the discovery of the relative chemosensitivities or toxicity of agents toward specific individuals, (xii) the discovery of the suitability of a specific organ donor for a specific individual, and (xiii) the development in vivo assays such as those utilizing radiolabeled probes suitable for the 3D imaging of specific gene expression within living humans. In addition, the present invention provides means to repeatedly analyze cells over time by providing means to specifically locate a particular cell present in a culture multiple times, even when incubation periods (i.e., the culture is placed in a cell culture incubator) are involved between each analysis.

In one embodiment of the VSOM approach a solution containing individual, dispersed, living cells (or very small clumps of cells or tissue fragments) is placed in a sterile vessel (i.e., in vitro). Unless there are means to attach the cells to the walls of the vessel, the cells settle to the bottom of the vessel, and then (if the conditions are correct) begin to attach to the bottom of the vessel. During this process, they flatten out and then (if the conditions are correct) begin to grow, divide, and proliferate. In some cases, the bottom surface of the vessel must be treated so that round cells, for example, which never tend to flatten out and attach to surfaces, will stick to the bottom surface of the vessel and not be washed away by the exchange of fluids.

In some preferred embodiments, the present invention utilizes a microscope, typically an inverted microscope, where the microscope's magnifying lens (i.e., the objective) is located beneath the vessel containing the solution of cells. A digital camera is mounted on the microscope so that digital pictures can be automatically acquired, and the cells are (in some cases) illuminated using standard white light from a standard halogen bulb. Standard transmitted light techniques (phase contrast, differential interference contrast, bright field, dark field, etc.) are then used to form an image of the cells suitable for imaging with the digital camera. In some cases, additional images are also rapidly acquired, in sequence, using very bright illumination, such as from a mercury or xenon arc lamp. This illumination light is passed through one or more optical filters that are contained in a computer controlled, rotating optical filter wheel, and a succession of digital images are acquired, in sequence, where the cells are illuminated with violet, blue, or yellow, filtered illumination light. On a microscope properly equipped for epifluoresence microscopy, cells containing one or more fluorescent probes will emit fluorescence light of a specific color when illuminated with fluorescence excitation light of the proper color. Thus, sequential digital images taken with the optical filter wheel in different positions will yield images where the blue, green, and red fluorescence being emitted from the cells appears in separate, sequential digital images, or separate "channels." In this manner, the amount and relative distribution of blue, green, or red (for example) fluorescent probes within the cell can be monitored in the digital images of blue, green or red fluorescence emission (the blue, green, and red channels), while the overall shape and texture of the cell can be observed in the transmitted light digital image (the transmitted light channel).

The relative intensity and color of fluorescence light seen within different intracellular compartments can represent the rate of uptake and retention of different fluorescent probes, and the way this fluorescence intensity partitions and redistributes within the cell gives important physiological, anatomical, and morphological information about the cell. Morphological information is also found in the transmitted light digital images. Changes in any or all of these parameters, as a function of time or applied stimulations, can be interpreted as a "response" of the cell to the applied fluorescent probes, and to the application of other stimulations or perturbations of the cell or its environment. Further, separate responses can be monitored and tracked in multiple, separate digital channels so that one response is seen in the red channel, one in the green, one in the blue, and one in the transmitted light channel. In this manner, the physiological responses to computer applied stimuli, perturbations, and interrogations become encoded in a series of digital images. As the digital images are passed to the computer, these responses are decoded by algorithms that extract the information contained in each digital image and detect the cellular responses that are, in a sense, a "reply" to computer applied stimuli.

In one particularly preferred embodiment of the present invention, cellular responses, or "replies," to computer applied interrogations (or "questions") that take the form of applied stress, stimulations, inhibitions, or perturbations, are rapidly decoded and interpreted during the course of the experiment (i.e., in "real-time"). Thus, additional "questions" can be asked, based on interpretation of previous "replies," or cellular responses. This process constitutes a communication loop between the cells and the computer, and it represents a means of "reading-out" information regarding the current biological state and current biological "circuitry" (e.g., current biological and biochemical processes) of individual living cells.

One means of applying computer-controlled stimulations, perturbations and interrogations is via computer-controlled syringe pumps. In this manner, various fluorescent probes, and solutions of chemical and biological agents, can be made to flow past attached living cells, and the responses of the cells to these agents can be monitored as the agents and probes are added or washed out of the cell specimen vessel. Such a process may be described as a modulation, or perturbation of the cell's microenvironment. Other, physical, means of perturbing the cells environment exist, such as altering the temperature of the cell vessel, or shining intense UV light on the cells, or applying an electric field to the cells in the vessel. Such physical modulations of the environment can be computer-controlled and do not require syringe pumps. In some particularly preferred embodiments, the user takes advantage of the computer's ability to keep track of vast numbers of previous combinations of such stimuli and how they were applied and what the cell responses were. This can be done not only by monitoring the current experiment, but also by referring back to a very large on-line computer database of previous cell stimulations and responses. The ability to access such a large database during the course of real-time experiments on living cells is a tremendous advantage over commonly used methods.

In addition, a specifically modulated (generated in a computer-controlled fashion), time-varying dynamic physiological response that is cell-type specific provides a means of identifying, discriminating and classifying different types of living cells. The current invention provides a means of discovering and refining such distinctive, cell-type specific "physiological fingerprints," to the point where they are minimally invasive and are relatively benign to living cells. The use of morphometric parameters (obtained on the transmitted light channel in the absence of any fluorescent probes) to quantify responses to benign perturbations of the environment, represents one example of a highly refined identification assay.

One challenge overcome during the development of the present invention is that standard digital image analysis techniques for delineating the outlines (contours) of living cells and their respective intracellular compartments are often inadequate for studies of living cells. These algorithms often require cells that are physically separated (i.e., the cells do not touch or overlap) and they also require cells that are very uniformly labeled with a relatively bright fluorescent stain. If the staining is non-uniform (i.e., some cells are brighter than others), or if the illumination pattern is not uniform, these algorithms will fail. In many cases, the long fluorescence light exposure times required for the successful use of these algorithms is toxic to living cells.

Once individual cells (and ideally, specific intracellular compartments) in the digital images are successfully detected and delineated by the proper computer algorithms, the changes in the amounts of fluorescent probes (i.e., in the case of fluorescence microscopy), or the changes in morphology that occur in response to computer applied stimulations can be quantified, recorded, and analyzed by a computer. The computer can then make decisions based on these analyses and can issue commands to the syringe pumps or other computer-controlled microscope peripherals in an effort to extract additional information from the living cells. This additional information, and all subsequent information from later cycles, is useful for optimizing and amplifying the small differences between cell types that are initially observed after a single stimulation.

Due to the normal heterogeneity and variation found between individual living cells (even those of the same type) it is often difficult or impossible to interpret the responses of living cells unless large numbers of cells are simultaneously observed. The need to observe large numbers of living cells and the concomitant need to rapidly process vast amounts of digital data is also addressed by the present invention. Such computing capabilities do not always reside on a local computer, and if they do this greatly increases the expense of the instrument. Thus, control of the instrument by a more powerful, remote computer is provided for in some embodiments of the present invention. Additionally, the requisite number of individual cells is not always visible in a single digital image, or in a single microscopic field of view. Thus, the ability to observe more cells by acquiring additional digital images in the immediate vicinity is provided for in alternative embodiments of the present invention.

The present invention further provides for observing high numbers of cells in the following manner. Biological responses and the biological consequences of applied stimuli are not always rapid, and are often relatively slow. This is especially true when the stimuli are applied in a slow, controlled fashion. Thus, the present invention allows for different groups of cells to be brought into the view of the digital camera in a sequential fashion. If five groups of cells are being monitored, the computer-controlled microscope stage repeatedly moves between five different areas of the specimen vessel in a continuous fashion, always returning to the same five population of cells at specified intervals, throughout the experiment. This precision is provided for not by an exceptionally precise xy stage, but by the ability of computer algorithms to redetect the cell contours and reacquire the same random distribution pattern representing a specific population of attached cells, and make small adjustments, as necessary, to the xy stage, until the same specific group of cells is again properly positioned for digital imaging.

Figure 4A:
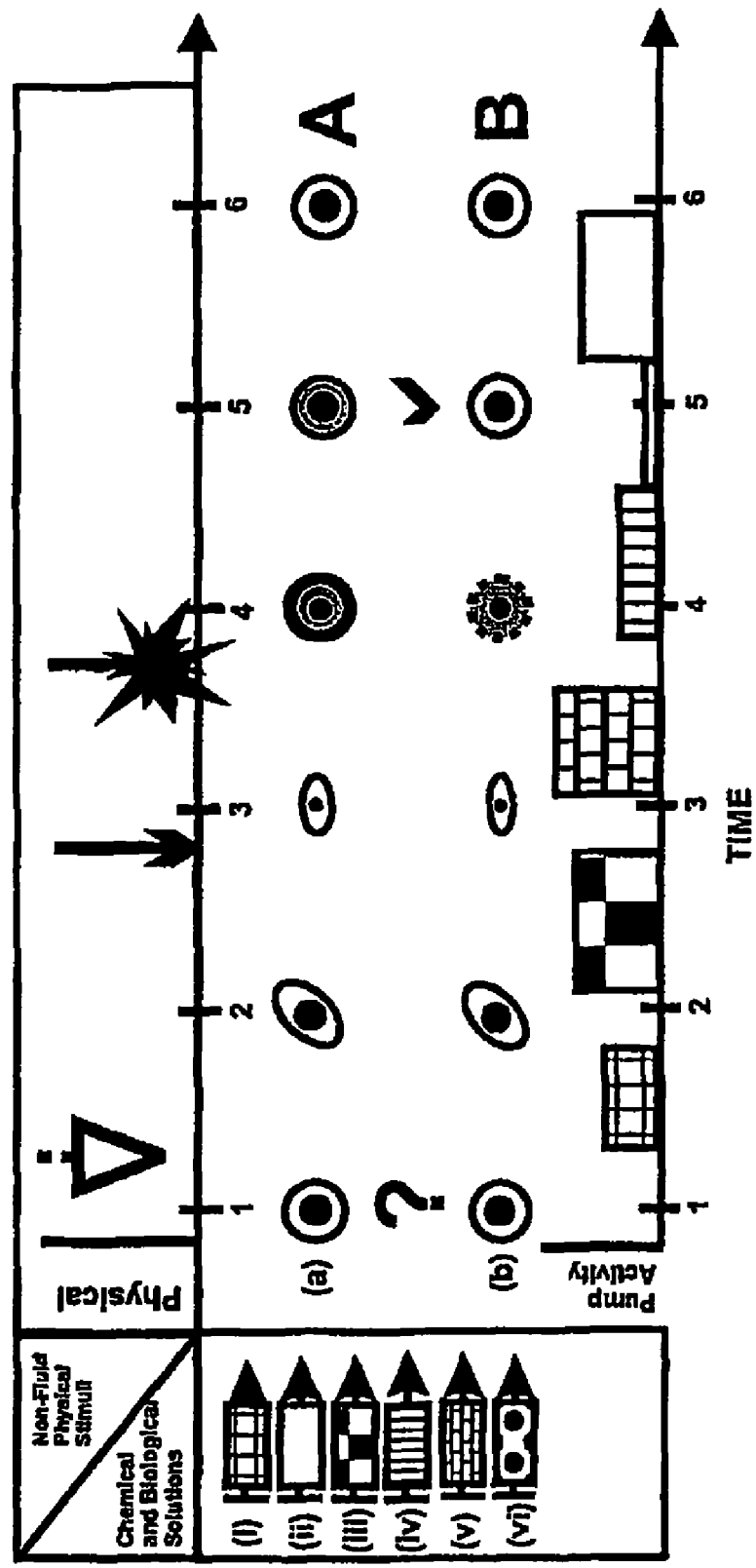
FIG. 4 provides a schematic diagram depicting one embodiment of a VSOM experiment.
Figure 4B:
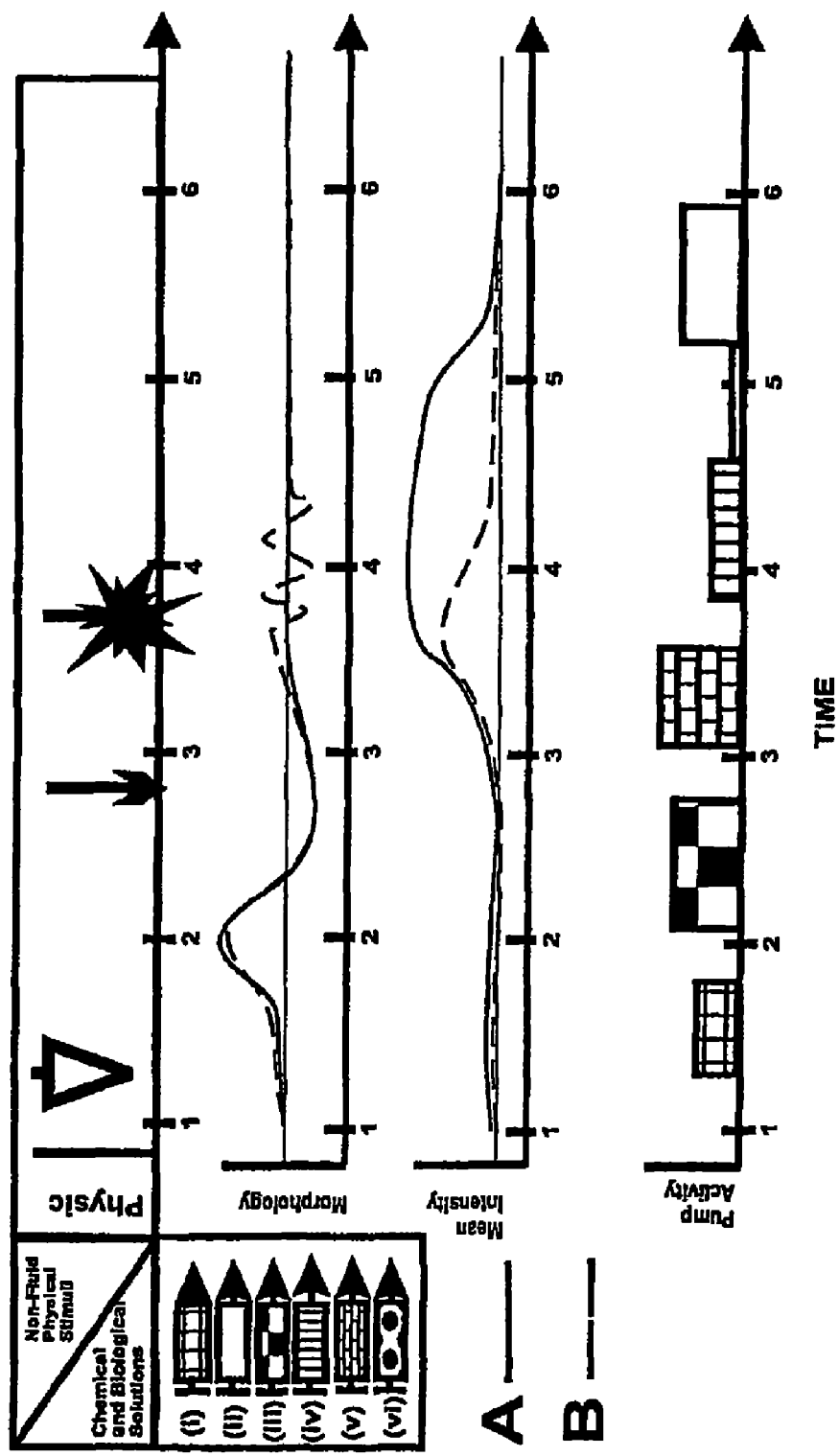
Figure 5:
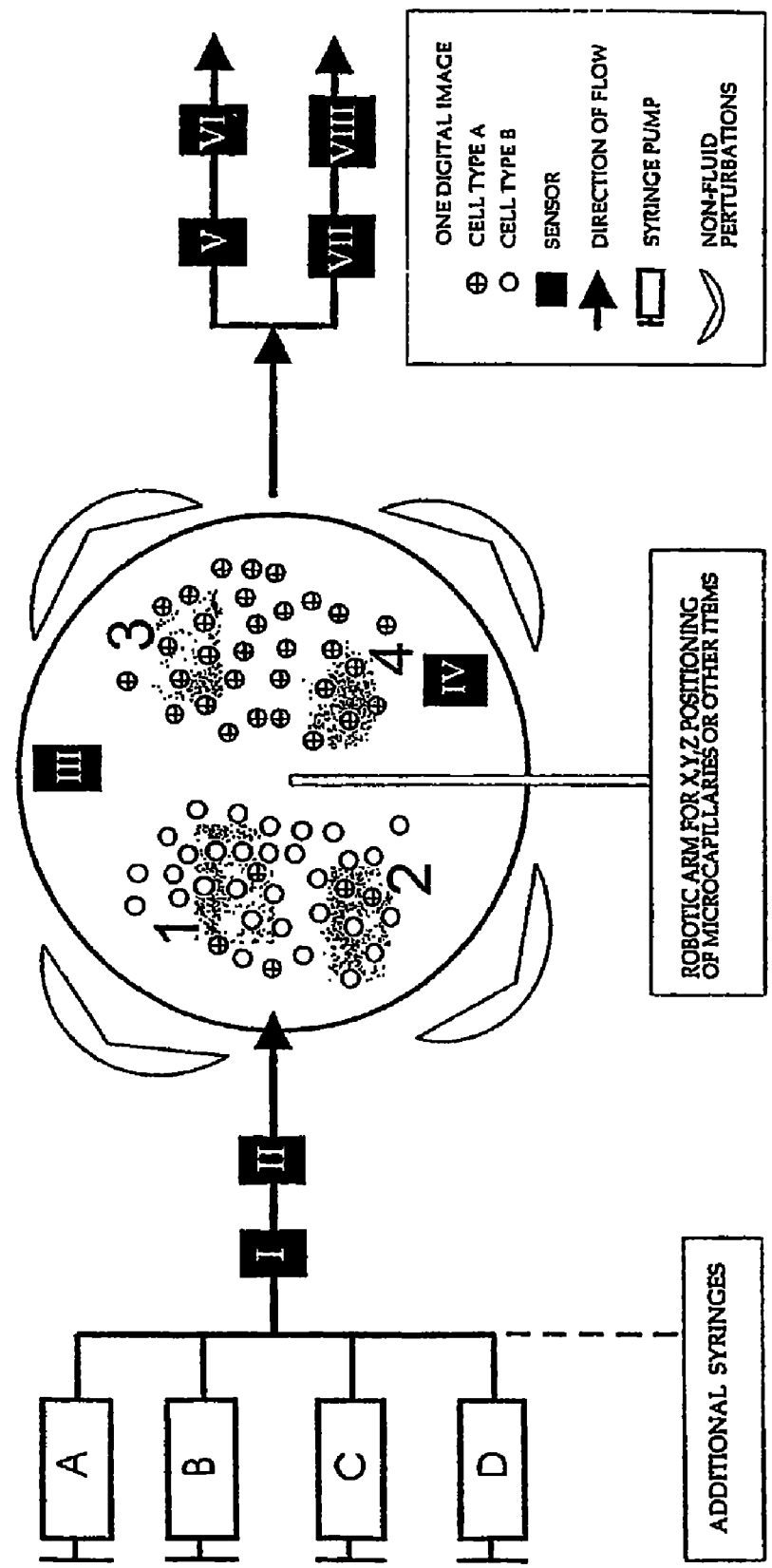
FIG. 5 provides a schematic diagram depicting one embodiment of a multi-field (MF) VSOM experiment.

Several examples of the concepts discussed above are schematically represented in various Figures (See e.g., FIGS. 4 and 5). The equipment required and example protocols are also discussed in greater detail herein.

As shown schematically in FIG. 5, one embodiment of a multi-field (MF) VSOM experiment can demonstrate many aspects of the present application. Four computer-controlled syringe pumps (A, B, C, D) infuse various solutions into a round micro-environmental chamber containing living cells and one or more environmental sensors. Solutions enter the cell chamber where two physically separated patches of cells have been deposited. In-line flow sensors I and II monitor the composition of infused solutions, while sensors III and IV monitor environmental conditions within the chamber. In this schematic, the cells on the left side represent a heterogeneous mixture of normal (hatched circles) and cancer cells (open circles) as would be expected (in this simplified model) from a breast tumor biopsy specimen. The cells on the right (hatched circles) represent a biopsy specimen taken from normal tissue (for example, from the opposite breast). A VSOM-controlled xy stage repeatedly repositions the cell chamber over the microscope objective (located beneath the chamber) so that the same sets of cells (1, 2, 3 and 4) are repeatedly imaged. The responses of these living cells are continuously quantified as various perturbations, are applied. These perturbations include the infusion of solutions of various compositions, and the control of other perturbations that cannot be administered as solutions. These perturbations could include gases, variations in temperature, irradiation, electric or magnetic fields or other physical perturbations applied by VSOM algorithms or recipes. In this diagram, the efflux from the environmental chamber also is monitored by in-line flow sensors V, VI, VII, and VIII. The responses of the cells are analyzed in real time using both fluorescence emission and transmitted light modalities. On the basis of ongoing VSOM analysis of individual responses to perturbations and changes in environment, the appropriate syringes and the appropriate environmental conditions are controlled by VSOM, in order to achieve specified experimental goals. In the case shown here, it is also possible to position a microcapillary near, or into specific cells.

A schematic diagram depicting one embodiment of a VSOM experiment is presented in FIG. 4. At the beginning of an experiment (time point 1), cell types A and B are randomly deposited onto a surface and exist as unidentified cells in a non-uniform array. The cells are denoted "a", "b", and "?" because they are indistinguishable at this initial time point. The VSOM system applies a series of solutions (from syringes i-v) and a series of physical stimuli as it searches for the protocol that will selectively label cell type A with a fluorescent dye (shown here as occurring at time point 5). At this point (indicated by a checkmark) the two cell types have been identified and the successful protocol and cell responses have been logged in a database. In some cases, the experiment ends at time point 5 with the successful discovery of a new protocol for selectively labeling cells of type A in the presence of cells of type B. The successful protocol is then further identified as the steps that took place between time points 3 and 5.

In subsequent experiments, only the steps between time points 3 and 6 are applied to cells, perhaps in an optimized manner, and the fluorescent dye is washed out, so that at time point 6, all cells of type A and type B have been identified and their respective positions in the array have been recorded. In this manner, one obtains an array of identified cells that have been (perhaps after further refinements of the labeling protocol) minimally perturbed, and that contain no foreign chemicals or markers. One may then begin a subsequent VSOM experiment using this VSOM generated array of identified living cells.

The sequence of events shown in FIG. 4, Panel A contain a great deal of experimental information and results which can be described in even greater detail. For example, between time points 1 and 2, cells are subjected to a physical perturbation (such as a decrease in temperature—indicated by the open headed arrow on the upper time line labeled "Physical Stimulation") followed by an infusion of the solution in syringe (i), where the graph labeled "Pump Activity" indicates that pump (i) operated for a certain duration (indicated by the width of the hatched rectangle on the time line) at a certain flow rate (height of hatched rectangle). At time point 2, a morphological change has occurred which has been continuously quantified for each cell using image analysis techniques. However, this cellular response is the same in both cell types. Thus, no distinction has been made between cell types and the automated search is continued. Between time points 2 and 3, an infusion of the solution in syringe (iii) is performed, followed by a physical stimulation (such as irradiation with UV light). At time point 3 both cell types are still behaving in a similar manner, so the experiment continues. Between time points 3 and 4 an infusion of solution from syringe (v) is performed which results in both cell types being labeled with a fluorescent dye (indicated by gray shading), and this is followed by the application of a physical stimulation (such as the application of an electric field) as solutions from syringes (iv and ii) are applied (approximately) between time points 4 and 5. This results in cells of type B losing fluorescent dye more quickly than cells of type A, with the result that only cells of type A are labeled at time point 5. Between time points 5 and 6 solution from syringe (ii) is applied at a higher flow rate until no cells contain any fluorescent dye (time point 6). In this manner, an entire array of living cells has been identified, and none of the cells contain a foreign compound or fluorescent probe. The cells do have a history of exposures and stimulations which can be minimized in future identification assays.

The time dependent responses of cell types A and B as detected by the computer via digital image segmentation and analysis might then appear as shown in FIG. 4, Panel B. In this Figure, the schematic drawings of cells have been replaced by the quantified responses detected by the computer on both a transmitted light channel (where the y-axis represents morphometric measurements representative of cell shape or texture), and a fluorescence light channel of a single color (where the y-axis represents a mean cellular fluorescence intensity). The responses of cell type A are shown as a solid line, while the responses of cell type B are shown as a dotted line. FIG. 4, Panel B illustrates one important concept of the present invention, namely the fact that the computer is able to make correlations across separate channels of response information. Such an instance is shown near time point 4 of FIG. 4, Panel B, where a change in cell membrane texture, for example, may give a morphometric response that can be correlated with the loss of fluorescence dye from the cell. After this phenomenon is verified, subsequent assays would not require the presence of a fluorescence dye to detect the cellular response. It would be identifiable in the morphometric response profile of the cell.

Thus, the present invention provides methods and devices for the knowledge-based discovery and optimization of differences between cell types. In particular, the present invention provides visual servoing optical microscopy as described above, as well as analysis methods. The present invention provides means for the close monitoring of hundreds of individual, living cells over time; quantification of dynamic physiological responses in multiple channels; real-time digital image segmentation and analysis; intelligent, repetitive computer-applied cell stress and cell stimulation; and the ability to return to the same field of cells for long-term studies and observation. The present invention further provides means to optimize culture conditions for specific subpopulations of cells.

Prior to the development of the present invention, it was technically difficult to digitally image large numbers of single living cells under a microscope. It was also difficult to simultaneously monitor multiple physiological responses in large numbers of single, living cells for an extended period of time without harming the cells. The first limitation existed largely because of the limited field of view at any given magnification. The field of view was further restricted by the limited size and resolution of the solid-state digital imaging device (i.e., charge-coupled device; CCD) inside the digital camera used. The present invention overcomes these limitations by facilitating the rapid, automatic, and repetitive monitoring of multiple fields of view (i.e., larger numbers of cells) by software control of an x,y,z microscope stage. The present invention also facilitates the simultaneous remote control of multiple microscopes from a central computer. Indeed, the present invention overcomes the memory, software, and processing resource limitations associated with presently used computers (i.e., clients) that control local microscope peripherals (e.g., scanning stages, filter wheels, perfusion pumps, robotic arms, shutters, cameras, etc.). The present invention allows VSOM to be performed by remote control using the internet, and a more powerful central computer (the server) located at a geographical location distant from the remote user(s). The server performs or distributes the more processing intensive tasks and serves as a central location for a very large database of current and previous cellular responses. Thus, the VSOM of the present invention takes advantage of the benefits derived from network access to a powerful central server and a large central database of previously observed single cell responses with previously observed correlations across multiple channels of information. In particularly preferred embodiments, the VSOM system repeatedly detects cells, logs and analyzes all of the observed cell responses across all channels, compares current cell responses, makes correlations across current channels of information, and consults a database of previously observed cell responses and previously observed correlations across different channels of information. Then, during the course of a single experiment, the system makes a series of knowledge-based decisions on how to adjust experimental parameters, in order to achieve the objective of the current experiment.

Thus, the present invention allows multiple, complete experimental cycles during the course of a single relatively short experiment. This greatly accelerates the process of searching for, discovering, and optimizing differences between different cell types. Relatively low numbers of cells are required, and because individual cell responses are monitored, specimens submitted for analysis may contain different types of cells. "Cell type" is a classification achieved by any observation that can separate a group of cells into multiple groups of cells, where each cell within a group has similar properties that distinguish it from cells in another group. This classification is typically based on repeated observation of relatively rapid physiological responses at the individual, single-cell level (e.g., observations of subcellular components, changes in morphology, cell division, cell death, detachment, etc.). However, the term also encompasses various cell types differentiated based on traditional histological criteria (e.g., epithelial cells, tumor cells, myocytes, adipocytes, nerve cells, etc.).

For large numbers of cells, the ability to rapidly make automated, knowledge-based decisions on how to alter experimental parameters during the course of an experiment was not available prior to the development of the present invention. The ability provided by the present invention to perform many "test/store/analyze/learn/re-design/re-test" cycles during the course of an experiment makes many experiments and applications possible that previously were unfeasible. When cells remain viable and an experiment remains in progress and on-line, correlations between past and future responses to stimuli are maintained on a cell-by-cell basis. Various and repeated computer-generated stimuli can be applied and repeated during a single experiment, using a relatively small sample of cells. This provides a tremendous advantage when searching for and optimizing differences between cell types. The term "stimulus" refers to single, repeated or continuous application of a stimulus, stimuli, or combination of stimuli. Stimuli that generate physiological responses encompass mechanical, physical, chemical, and biological entities. Thus, it is not intended that the present invention be limited to any stimulus or type of stimulus.

Living cells can move or change shape. Thus, when returning to a given field of view, the software must adjust focus (z-axis control), and must make small horizontal and vertical adjustments to reacquire and re-register the field of view (x,y axis control). In addition, the original contours defining the outline of the individual cells must be modified in order to track changes in cell position and shape. Thus, in one embodiment, the VSOM of the present invention provide means to make decisions regarding control of the instrument based on analysis of image content. Indeed, the present invention provides means for: computer automation of repeated and/or continuous application of stimuli (or a stimulus) to living cells; repeated and/or continuous detection and monitoring of one or more cellular or subcellular physiological responses to the stimuli at the single cell level, using microscopy and digital imaging; rapid observation of a sufficient number of individual cell responses to establish criteria suitable for reliable identification of cell type(s) and/or modification of the stimuli in order to optimize differences between cell types; rapid analysis of current and previously stored (e.g., database information) cell responses so that knowledge-based stimulus control decisions can be made while cells are available for observation and/or stimulation; and monitoring of the correlations between time-dependent events across multiple channels.

The present invention further provides means to define the contours of living cells using transmitted light in addition to fluorescence emission light. This facilitates the tracking of cells that do not contain a fluorescent compound. In addition, this allows the use of smaller amounts of potentially cytotoxic fluorescent labeling compounds and avoids the intense fluorescence excitation illumination required to stimulate fluorescence emission. Thus, cells can be observed for longer periods of time. Furthermore, cells with specific behaviors can be individually retrieved at the end of the experiment for pooling, establishment of cell lines, cloning, propagation towards a given differentiated state, analysis, etc.

In addition to monitoring a larger number of cells, the present invention allows a larger number of physiological responses to be observed during a single experiment because the instrument can observe different physiological responses in different channels essentially simultaneously, by rapidly cycling the imaging from transmitted light to fluorescence emission light of different wavelengths.

On-going fluorescence signals from an entire population of living cells can be detected using a multiwell fluorescence plate reader. However, single cell responses cannot be observed. Nonetheless, one embodiment of the VSOM of the present invention provides for the discovery and optimization of fluorescence assays that are suitable for multiwell plate readers. Furthermore, using common techniques, multi-channel fluorescence signals from individual living cells can be detected at a single instant using flow cytometry. The cells can be sorted according to fluorescence signal and can also be recovered. However, the cells flow rapidly past a detector and a single (perhaps multichannel) measurement is taken. Individual cells are not tracked for any length of time and repeated observations of the same cell, with correlations between past and present responses is not possible. The present invention overcomes these limitations and facilitates the development and optimization of fluorescence assays that are suitable for flow cytometry and activated cell sorting.

The present invention finds use in cell-type specific fluorescence assays that are useful for any types of cells (e.g., animal, plant, microorganisms, etc.). Thus, it is not intended that the present invention be limited to any type of cells or any particular fluorescence or other assay system. While preferred embodiments involve human cells, other embodiments involve cells obtained from other mammals, as well as plants, and other organisms. For example, the present invention provides means for the detection and discrimination between normal, pre-malignant, malignant, and/or multi-drug resistant cancer cells obtained from tissue (e.g., biopsies, surgical removal of tissue, etc.). In addition, the present invention provides means for the design of protocols that selectively label rare cell types (e.g., stem cells or fetal cells in maternal blood). In some embodiments, these protocols are modified for use with radioactive and other label systems. The present invention also facilitates design and application of assays to establish a chemotherapeutic regimen (including a combination of drugs), that is tailored to an individual patient and/or an individual tumor within a patient. In addition, the present invention provides assays useful for screening large numbers of potential drug, insecticide, herbicide, and other compounds for numerous uses in medicine, agriculture, biotechnology, etc. The present invention further provides assays useful for screening large numbers of potential agents for use in cell proliferation, cytotoxicity and/or differentiation.

The present invention further provides means to design in vitro tissue culture conditions that lead to the proliferation of a specific cell type, either by giving a growth advantage to the cell type of interest, or by designing environmental conditions or protocols that are cytotoxic to other cell types present in the culture. Thus, the present invention provides means to cultivate cells that are often difficult to grow in vitro. In addition, the present invention provides means to produce cell culture conditions that are suitable for guiding cells to a specific differentiated end-point. For example, using the present invention, conditions necessary to guide stem cells or embryonic cells to a final desired end point can be developed.

The present invention also finds use in the development and performance of various types of rapid in vitro tests. For example, if several potential tissue or bone marrow donors exist for a particular patient, the various donors' cells are mixed with the patient's immune cells and observations of any immune rejection response are made on the single cell level. Thus, identification of the best donor for that particular patient is facilitated. In addition, these tests are performed in the presence of drugs (or drug candidates) designed to suppress transplant rejection, facilitating the choice of the optimum anti-rejection drug treatment regimen (i.e., single drug or multiple drugs in combination), as well as the best donor for the patient.

DETAILED DESCRIPTION OF THE INVENTION

The present invention provides methods and devices for the knowledge-based discovery and optimization of differences between cell types. In particular, the present invention provides visual servoing optical microscopy (VSOM), as well as analysis methods. The present invention provides means for the close monitoring of hundreds of individual, living cells over time; quantification of dynamic physiological responses in multiple channels; real-time digital image segmentation and analysis; intelligent, repetitive computer-applied cell stress and cell stimulation; and the ability to return to the same field of cells for long-term studies and observation.

Figure 2:
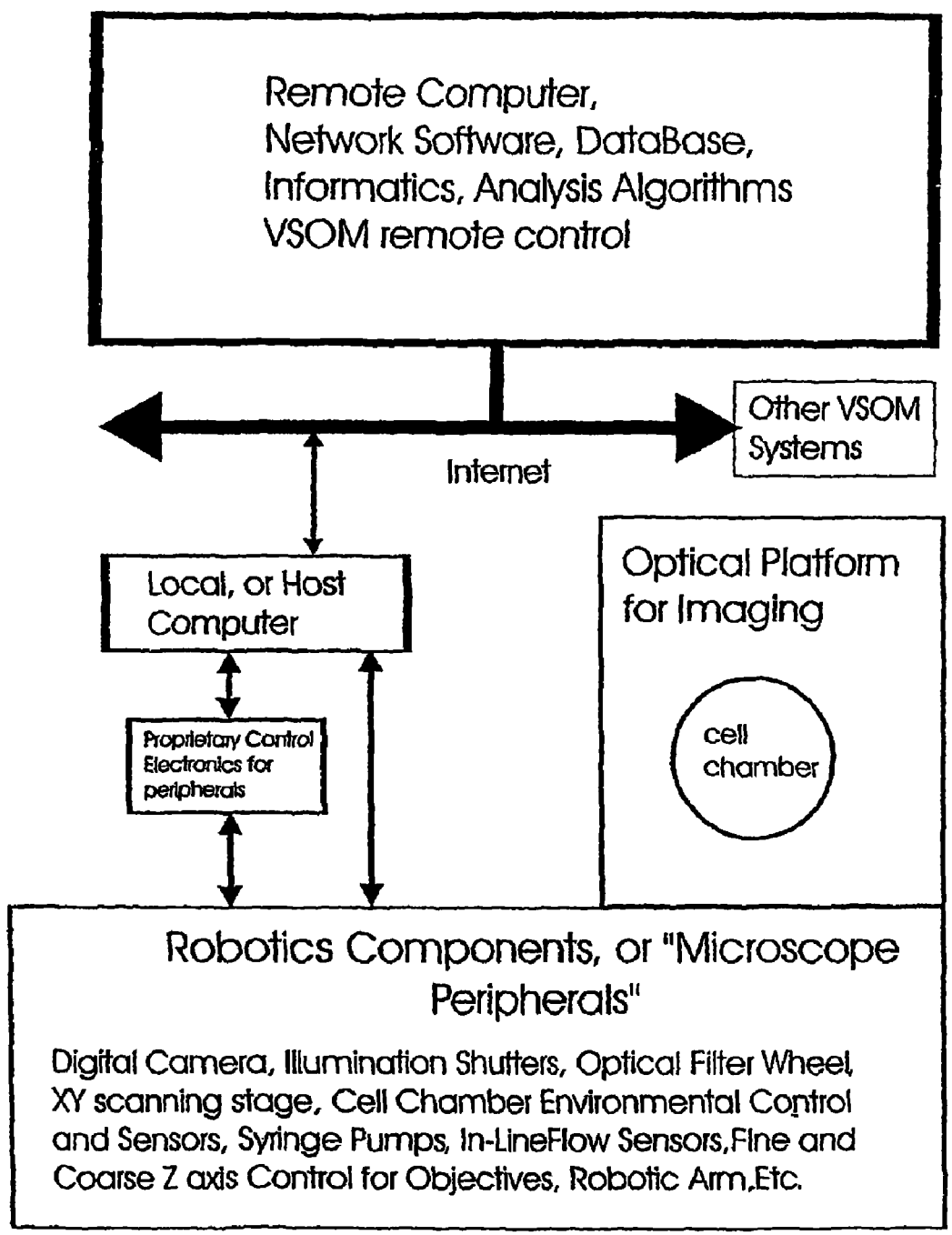
FIG. 2 provides a further schematic showing alternative embodiments of the present invention.
Figure 3:
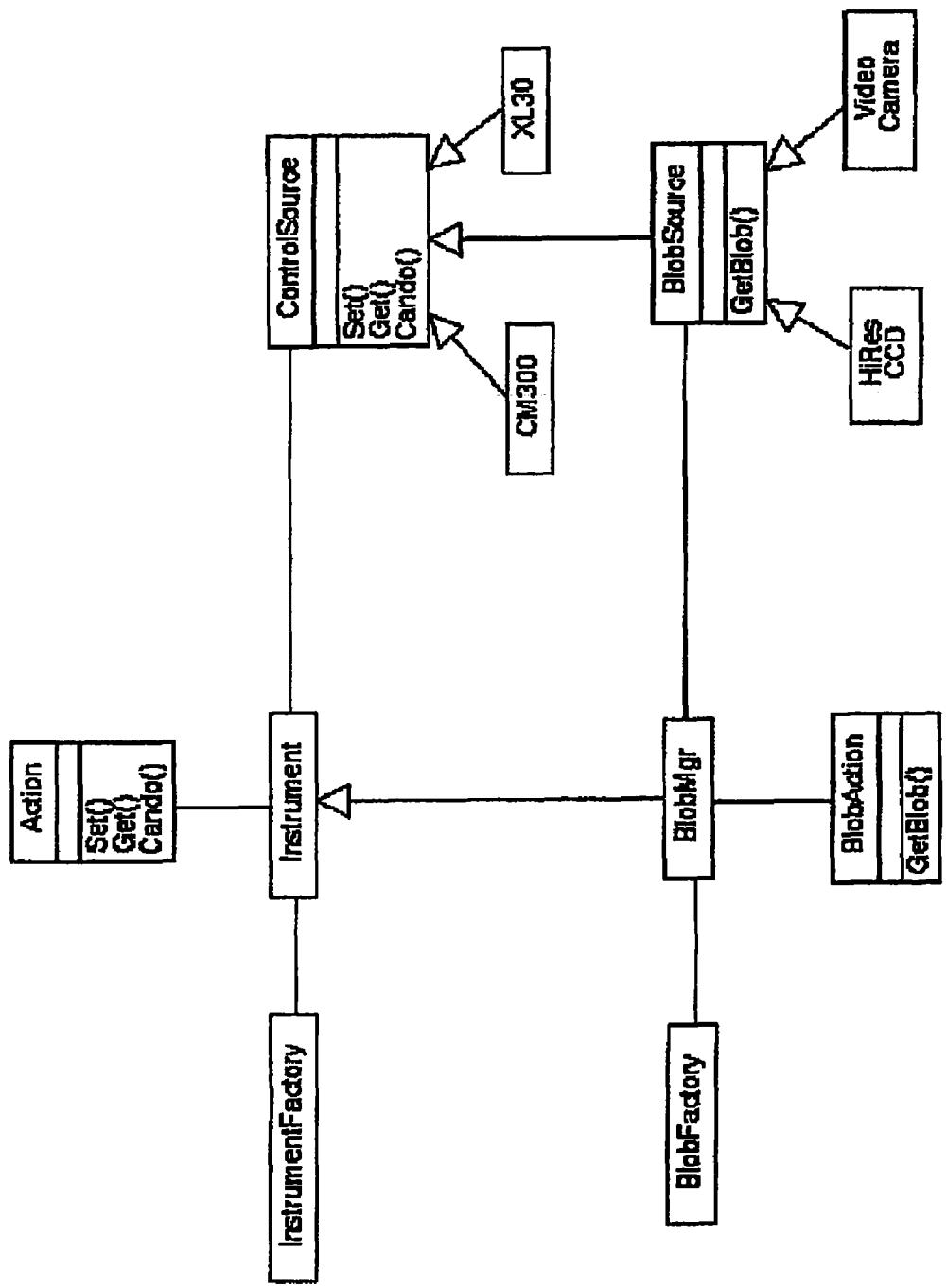
FIG. 3 provides a schematic showing the relationship of key objects for Blob Manager and Instrument Manager. Each additional instrument requires a plug in for ControlSource and BlobSource. The details of ControlSource and BlobSource are hidden at the IDL level.

FIGS. 1 and 2 provide schematics of the three main components of preferred embodiments of the present invention. These consist of (i) the optical platform for digital imaging of living cells in a cell chamber, (ii) a variety of computer controlled peripherals, referred to as "robotic components" which are often physically mounted on or near the optical platform, (iii) a local host computer (a "client") used for local command of the robotic peripherals. In additional embodiments, the present invention further provides a remote computer (i.e., the "server") containing software for remote control of VSOM instruments and processes over the Internet (See, FIG. 2).

A. Optical Platform, Robotic Components, and Control Electronics

In one embodiment of the present invention, the VSOM optical platform is an inverted optical microscope that is configured for both transmitted light illumination and epifluorescence illumination of a specimen that is mounted in the center of the microscope stage. Several microscope objectives are mounted beneath the microscope stage for image formation and magnification. In one embodiment, four robotic components (i.e., computer controlled microscope peripherals) are also positioned near the microscope stage. In particularly preferred embodiments, a digital camera containing an internal camera shutter is mounted on one of the microscope's upper camera ports. The microscope stage is a computerized XY scanning stage, and the location of two computer controlled shutters are included, where an upper shutter controls transmitted light illumination, and an internal rear shutter controls epifluorescence illumination. In addition to an internal shutter contains a computer controlled, six-position rotating optical filter wheel that allows illumination and fluorescence excitation of the specimen with light of a defined spectral composition.

In alternative embodiments, a second camera (e.g., mounted on the base camera port) is used. However, two cameras are not necessary for a VSOM. In addition to the xy scanning stage adjustment, there is a housing for a stepping motor used for coarse z-axis positioning (focus control) of microscope objectives, and a computer-controlled XYZ microcapillary positioner or "robotic arm." In most embodiments, the microscope objective is positioned directly beneath the microscope "stage plate" (or specimen holder). Various removable stage plates can be inserted into the xy scanning stage, depending on the chamber or vessel to be used in an experiment. Numerous specimen holders, or "stage plates" find use with the present invention. In some embodiments, non-environmentally controlled specimen vessels are used. Stage plates for chambered coverglass, tissue culture flasks, cell culture dishes, and multiwell plates also find use with the present invention. In some embodiments of the present invention, it is possible to simply remove various sterile specimen vessels from a cell incubator, place them on the microscope using the appropriate stage plate, and have the VSOM system scan and count the number of cells in the vessel, using only transmitted light illumination. Since morphological measurements can also be made under these circumstances on a cell by cell basis, where individual cells have been detected and segmented in digital images, it is also be possible to monitor features of cell morphology, such as shape, area, and texture, and nuclear to cytoplasmic ratio.

In some cases, microenvironmentally controlled cell chambers are physically coupled to the stage or are connected via a stage plate. Indeed, any appropriate cell chamber (i.e., receptacle to contain cells to be analyzed and/or observed). Various types of commercially available, environmentally controlled cell chambers are available and are suitable for use with the xy scanning stage. In some embodiments, a peristaltic pump or some other pump removes excess liquid from the specimen vessel. In other embodiments, the temperature of the cell chamber (or specimen vessel) is monitored. In these embodiments, the temperature probe typically leads to a controller that regulates the temperature of the liquid in the chamber or the temperature of the chamber itself. This particular independent, non-computer controlled temperature control unit is replaced in preferred embodiments with a computer controllable unit.

An addition feature of the cell chamber is its ability to layer a flow of gas of a defined oxygen composition over the specimen vessel sitting within the cell chamber. In this manner, it is possible to create conditions of known oxygen tension within the specimen vessel and solution, or to control the pH of solutions containing bicarbonate buffers by altering the amount of $CO_2$ in the gas flowing over the specimen vessel.

In some embodiments, two computer-controlled pumps with four independently controllable syringes are shown adjacent to the optical platform. Electronic controllers are built into each of the two pump units, which are daisy-chained together. Up to approximately 99 pump units can be connected in this fashion, and each of two syringes on a pump is independently controllable.

As indicated in FIGS. 1 and 2, many of the peripherals are provided with control units that serve as an interface between the host computer and the robotic peripheral itself. Elementary software commands are provided by the manufacturer of these peripherals, so that control of the microscope peripheral can be built into custom software that runs on the host computer. The host computer can, in turn, be controlled software that runs on the remote computer. For example, the coarse z-axis focusing motor, the xy scanning stage, the two illumination shutters, digital camera (and its internal shutter), and the optical filter wheel, can all be controlled using this software. In some embodiments, fine focus control of the microscope is provided by a piezoelectric positioner that screws into the objective turret of the microscope. The microscope objective, in turn, screws into the piezoelectric positioner.

1. Microarray Formats

The present invention provides the capability of rapidly screening a large number of compounds (e.g., drugs or other compounds suspected of a having a biological activity of interest) over a succession of treatments for a variety of cell types, via a high throughput screen, to more completely assess the physiological responsiveness of the cells/individual cell types to a particular agent, treatment, or set of treatments. Manipulation and analysis of drug-cell interactions using current methods does not allow for both high throughput and high biological content screening, due to the small number of bioassays that can be analyzed in a given period of time, the cumbersome methods required for compound delivery, and the often large volumes of compounds required for testing. Therefore, a preferred embodiment of the present invention provides for high throughput screening in a microarray format.

In a preferred embodiment, the present invention detects and process optical image signals from individual cells according to cell type. A non-uniform microarray can therefore be made by placing a plurality of cell types onto a support or plate, identifying the individual cell types according to their optical image, and tracking the responsiveness of the individual cell or cell types to an applied environmental stimulus. Such cell types may be fixed at suitably low cell densities to allow detection and analysis of the light from a single cell upon either a uniform or non-uniform microarray as described above. In other embodiments, the invention detects and measures the collective light signal from a plurality of cells undergoing the same treatment.

In a preferred embodiment, the cells are fixedly attached to the support. Suitable methods for attaching cells in micropatterned arrays are known, including for example photochemical resist-photolithograpy (Mrksich and Whitesides, Ann. Rev. Biophys. Biomol. Struct. 25:55-78, 1996). According to this photoresist method, a glass plate is uniformly coated with a photoresist and a photo mask is placed over the photoresist coating to define the "array" or pattern desired. Upon exposure to light, the photoresist in the unmasked areas is removed. The entire photolithographically defined surface is uniformly coated with a hydrophobic substance such as an organosilane that binds both to the areas of exposed glass and the areas covered with the photoresist. The photoresist is then stripped from the glass surface, exposing an array of spots of exposed glass. The glass plate then is washed with an organosilane having terminal hydrophilic groups or chemically reactable groups such as amino groups. The hydrophobic organosilane binds to the spots of exposed glass with the resulting glass plate having an array of hydrophilic or reactable spots (located in the areas of the original photoresist) across a hydrophobic surface. The array of spots of hydrophilic groups provides a substrate for non-specific and non-covalent binding of certain cells, including those of neuronal origin (Kleinfeld et al., J. Neurosci. 8:4098-4120, 1988). Reactive ion etching has been similarly used on the surface of silicon wafers to produce surfaces patterned with two different types of texture (Craighead et al., Appl. Phys. Lett. 37:653, 1980; Craighead et al., J. Vac. Sci. Technol. 20:316, 1982; and Suh et al. Proc. SPIE 382:199, 1983).

Another method for making a uniform microarray of cells is based on specific yet non-covalent interactions, photoresist stamping is used to produce a gold surface coated with protein adsorptive alkanethiol. (Singhvi et al, Science 264:696-698, 1994). The bare gold surface is then coated with polyethylene-terminated alkanethiols that resist protein adsorption. After exposure of the entire surface to laminin, a cell-binding protein found in the extracellular matrix, living hepatocytes attach uniformly to, and grow upon, the laminin coated islands (Singhvi et al. 1994). An elaboration involving strong, but non-covalent, metal chelation has been used to coat gold surfaces with patterns of specific proteins (Sigal et al., Anal. Chem. 68:490-497, 1996). In this case, the gold surface is patterned with alkanethiols terminated with nitriloacetic acid. Bare regions of gold are coated with tri(ethyleneglycol) to reduce protein adsorption. After adding $Ni^{2+}$, the specific adsorption of five histidine-tagged proteins is found to be kinetically stable.

More specific uniform cell-binding can be achieved by chemically crosslinking specific molecules, such as proteins, to reactable sites on the patterned substrate. (Aplin and Hughes, Analyt. Biochem. 113:144-148, 1981). Another elaboration of substrate patterning optically creates an array of reactable spots. A glass plate is washed with an organosilane that chemisorbs to the glass to coat the glass. The organosilane coating is irradiated by deep UV light through an optical mask that defines a pattern of an array. The irradiation cleaves the Si—C bond to form a reactive Si radical. Reaction with water causes the Si radicals to form polar silanol groups. The polar silanol groups constitute spots on the array and are further modified to couple other reactable molecules to the spots, as disclosed in U.S. Pat. No. 5,324,591, incorporated by reference herein. For example, a silane containing a biologically functional group such as a free amino moiety can be reacted with the silanol groups. The free amino groups can then be used as sites of covalent attachment for biomolecules such as proteins, nucleic acids, carbohydrates, and lipids. The non-patterned covalent attachment of a lectin, known to interact with the surface of cells, to a glass substrate through reactive amino groups has been demonstrated (Aplin & Hughes, 1981). The optical method of forming a uniform array of cells on a support requires fewer steps and is faster than the photoresist method, (i.e., only two steps), but it requires the use of high intensity ultraviolet light from an expensive light source.

In another embodiment, the cell array and addition of test stimuli are according to methods and compositions taught in U.S. Pat. No. 6,103,479, incorporated by reference in its entirety herein. The '479 patent discloses a preferred means of providing a miniaturized cellular array which allows for the delivery of compounds of interest (e.g., drugs and other biologically active compounds). The '479 patent discloses means and methods for performing high throughput and high content screening of the physiological response of cells to biologically active compounds. A non-uniform micro-patterned array of cells refers to an array of cells on a base that are not distributed in a single uniform coating on the support surface, but rather in a non-uniform fashion such that each "well" or groups of wells on the support may be unique in its cell binding selectivity. Any cell type can be arrayed on the non-uniform micro-patterned array of cells, providing that a molecule capable of specifically binding that cell type is present in the micro-patterned chemical array. Preferred cell types for the non-uniform micro-patterned array of cells include lymphocytes, cancer cells, neurons, fungi, bacteria and other prokaryotic and eukaryotic organisms.

The method of making the '479 patent non-uniform micro-patterned array of cells comprises preparing a micro-patterned chemical array, chemically modifying the micro-patterned chemical array non-uniformly, and binding cells to the non-uniform modified micro-chemical array on the base. The base can be a glass, plastic, or silicon wafer, such as a conventional light microscope coverslip, but can also be made of any other suitable material to provide a base. As indicated herein, the term "wells" is used to describe a specific spot on the base, and does not require any particular depth. The methods of making such an array are taught in the '479 patent. In a preferred embodiment, as disclosed therein, a modified micro-patterned chemical array is produced in combinatorial fashion. The resulting wells are non-uniform (i.e., each well or group of wells may be unique in its cell binding selectivity). By the term combinatorial, it is meant that the wells are variably treated.

2. Microfluidics Format

Efficient delivery of solutions to a microarray of cells attached to a solid substrate, is facilitated by a system of microfluidics. Methods and apparatus have been described for the precise handling of small liquid samples for ink delivery (U.S. Pat. Nos. 5,233,369; 5,486,855; 5,502,467; all of which are incorporated by reference herein), biosample aspiration (U.S. Pat. No. 4,982,739, incorporated by reference herein), reagent storage and delivery (U.S. Pat. No. 5,031,797 incorporated by reference herein), and partitioned microelectronic and fluidic device array for clinical diagnostics and chemical synthesis (U.S. Pat. No. 5,585,069 incorporated by reference herein). In addition, methods and apparatus have been described for the formation of microchannels in solid substrates that can be used to direct small liquid samples along the surface (U.S. Pat. Nos. 5,571,410; 5,500,071; 4,344,816, all of which are incorporated by reference herein). Methods for delivering solutions to living cells micro-patterned into non-uniform arrays on solid substrates in a closed optical chamber are disclosed in U.S. Pat. No. 6,103,479, also incorporated by reference herein.

Preferred embodiments of the non-uniform micro-patterned array of cells are disclosed above. In a preferred embodiment of the fluid delivery system, a chamber, mates with the base containing the non-uniform micro-patterned array of cells. The chamber is preferably made of glass, plastic or silicon, but any other material that can provide a base is suitable. One embodiment of the chamber has an array of etched domains matching the wells in the non-uniform micro-patterned array of cells. In addition, microfluidic channels are etched to supply fluid to the etched domains. A series of "waste" channels, to remove excess fluid from the etched domains, can also be connected to the wells. The chamber and micro-patterned array of cells together constitute a cassette.

"Fluids" include, but are not limited to a solution of a particular drug, protein, ligand, or other substance which binds with surface expressed moieties of cells or that are taken up by the cells. The fluid to interact with the non-uniform micro-patterned array of cells can also include liposomes encapsulating a drug. In one embodiment, such a liposome is formed from a photochromic material, which releases the drug upon exposure to light, such as photoresponsive synthetic polymers. (Reviewed in Willner and Rubin, Chem. Int. Ed. Engl. 35:367-385, 1996). The drug can be released from the liposomes in all channels 14 simultaneously, or individual channels or separate rows of channels may be illuminated to release the drug sequentially. Such controlled release of the drug may be used in kinetic studies and live cell studies. Control of fluid delivery can be accomplished by a combination of micro-valves and micro-pumps that are well known in the capillary action art. (U.S. Pat. Nos. 5,567,294; 5,527,673; and 5,585,069, all of which are herein incorporated by reference.)

In preferred embodiments, delivery of drugs or other substances is accomplished as follows. A solution of the agent to be tested for interaction with cells of the array can be loaded from a 96 well microtiter plate into an array of microcapillary tubes. The array of microcapillary tubes corresponds one-to-one with the microfluidic channels of the chamber allowing solution to flow or be pumped out of the microcapillary tubes into the channels. The non-uniform micro-patterned array of cells is inverted so that the wells become submerged in the etched domain filled with the fluid. Once the interaction between the fluid and non-uniform micro-patterned array of cells occurs, light emanating from the non-uniform micro-patterned array of cells can be measured directly and converted to optical input to guide the placement, removal and treatment of the array of cells automatically via robotics.

3. Fluorescence Format

As indicated herein, a particularly preferred embodiment involves fluorescence imaging of cells. A variety of methods have been developed to image fluorescent cells with a microscope and extract information about the spatial distribution and temporal changes occurring in these cells. Many of these methods and their applications have been recently described (Taylor et al., Am. Scientist 80:322-335, 1992; See also, U.S. Pat. No. 6,103,479). These methods have been designed and optimized for the preparation of small numbers of specimens for high spatial and temporal resolution imaging measurements of distribution, amount and biochemical environment of the fluorescent reporter molecules in the cells.

Treating cells with dyes and fluorescent reagents and imaging the cells (Wang et al., In Methods in Cell Biology, New York, Alan R. Liss, 29:1-12, 1989), and genetic engineering of cells to produce fluorescent proteins, such as modified green fluorescent protein (GFP) as a reporter molecule are useful detection methods. The green fluorescent protein (GFP) of the jellyfish *Aequorea victoria* has an excitation maximum at 395 nm, an emission maximum at 510 nm and does not require an exogenous factor. Uses of GFP for the study of gene expression and protein localization are discussed in Chalfie et al., Science 263:802-805, 1994. Some properties of wild-type GFP are disclosed by Morise et al. (Biochemistry 13:2656-2662, 1974), and Ward et al. (Photochem. Photobiol. 31:611-615, 1980). An article by Rizzuto et al. (Nature 358:325-327, 1992) discusses the use of wild-type GFP as a tool for visualizing subcellular organelles in cells. Kaether and Gerdes (FEBS Letters 369:267-271, 1995) report the visualization of protein transport along the secretory pathway using wild-type GFP. The expression of GFP in plant cells is discussed by Hu and Cheng (FEBS Letters 369:331-334, 1995), while GFP expression in Drosophila embryos is described by Davis et al. (Dev. Biology 170:726-729, 1995). U.S. Pat. No. 5,491,084, incorporated by reference herein, discloses expression of GFP from Aequorea Victoria in cells as a reporter molecule fused to another protein of interest. PCT/DK96/00052, incorporated by reference herein, relates to methods of detecting biologically active substances affecting intracellular processes by utilizing a GFP construct having a protein kinase activation site. Numerous references are related to GFP proteins in biological systems. For example, PCT/US95/10165 incorporated by reference herein, describes a system for isolating cells of interest utilizing the expression of a GFP like protein. PCT/GB96/00481 incorporated by reference herein, describes the expression of GFP in plants. PCT/US95/01425 incorporated by reference herein, describes modified GFP protein expressed in transformed organisms to detect mutagenesis. Mutants of GFP have been prepared and used in several biological systems. (Hasselhoff et al., Proc. Natl. Acad. Sci. 94:2122-2127, 1997; Brejc et al., Proc. Natl. Acad. Sci. 94:2306-2311, 1997; Cheng et al., Nature Biotech. 14:606-609, 1996; Heim and Tsien, Curr. Biol. 6:178-192, 1996; and Ehrig et al., FEBS Letters 367:163-166, 1995). Methods describing assays and compositions for detecting and evaluating the intracellular transduction of an extracellular signal using recombinant cells that express cell surface receptors and contain reporter gene constructs that include transcriptional regulatory elements that are responsive to the activity of cell surface receptors are disclosed in U.S. Pat. Nos. 5,436,128 and 5,401,629, both of which are incorporated by reference herein.

The ArrayScan™ System, as developed by BioDx, Inc. (U.S. patent application Ser. No. 08/810,983) is an optical system for determining the distribution, environment, or activity of luminescently labeled reporter molecules in cells for the purpose of screening large numbers of compounds for specific biological activity. The ArrayScan™. System involves providing cells containing luminescent reporter molecules in a uniform array of locations and scanning numerous cells in each location with a fluorescence microscope, converting the optical information into digital data, and utilizing the digital data to determine the distribution, environment or activity of the luminescently labeled reporter molecules in the cells. The uniform array of locations used presently are the industry standard 96 well or 384 well microtiter plates. The ArrayScan™. System includes apparatus and computerized method for processing, displaying and storing the data, thus augmenting drug discovery by providing high content cell-based screening in a large microtiter plate format.

The above embodiments can be combined to provide for methods and apparatus so as to provide multicolor luminescence reading, microfluidic delivery, and automatic environmental control of living cells in uniform or non-uniform micro-patterned arrays.

In one embodiment, the present invention encompasses a non-uniform micro-patterned array of cells and methods for making same. The arrays can comprise identical cell types that can be treated with a combinatorial of distinct compounds, or a combinatorial of cell types that can be treated with one or more compounds. By the term combinatorial, it is meant that the wells or groups of wells are variably treated. A further aspect of the present invention comprises a method for analyzing cells, by using the non-uniform micro-patterned cell array where the cells contain at least one luminescent reporter molecule in combination with a fluid delivery system to deliver a combinatorial of reagents to the micro-patterned array of cells, and means to detect, record and analyze the luminescence signals from the luminescent reporter molecules. In another aspect of the present invention, a cell screening system is disclosed, comprising a luminescence reader instrument for detecting luminescence signals from the luminescent reporter molecules in the non-uniform micro-patterned array of cells, a digital detector for receiving data from the luminescence reader instrument, and a computer means for receiving and processing digital data from the light detector.

In another embodiment, the cells can be modified with luminescent indicators of cell chemical or molecular properties, seeded onto the non-uniform micro-patterned chemical array and analyzed in the living state. Examples of such indicators are provided in Giuilano et al., Ann. Rev. Biophys. Biomol. Struct. 24:405-434, 1995; Harootunian et al., Mol. Biol. Cell 4:993-1002, 1993; Post et al., Mol. Biol. Cell 6:1755-1768, 1995; Gonzalez and Tsien, Biophys. J. 69:1272-1280, 1995; Swaminathan et al., Biophys. J. 72:1900-1907, 1997 and Chalfie et al., Science 263:802-805, 1994. The indicators can be introduced into the cells before or after they are seeded onto the array by any one or a combination of variety of physical methods, such as, but not limited to diffusion across the cell membrane (reviewed in Haugland, Handbook of fluorescent probes and research chemicals, 6, sup, ed. Molecular Probes, Inc., Eugene, 1996), mechanical perturbation of the cell membrane (McNeil et al., J. Cell Biology 98:1556-1564, 1984; Clarke and McNeil, J. Cell Science 102:533-541, 1992; Clarke et al., BioTechniques 17:1118-1125, 1994), or genetic engineering so that they are expressed in cells under prescribed conditions. (Chalfie et al., 1994). In a preferred embodiment, the cells contain luminescent reporter genes, although other types of reporter genes, including those encoding chemiluminescent proteins, are also suitable. Live cell studies permit analysis of the physiological state of the cell as reported by luminescence during its life cycle or when contacted with a drug or other reactive substance.

In another aspect of the invention, a method for analyzing individual cells is provided, comprising preparing a non-uniform micro-patterned array of cells wherein the cells contain at least one luminescent reporter molecule, contacting the non-uniform micro-patterned array of cells to a fluid delivery system to enable reagent delivery to the non-uniform micro-patterned array of cells, conducting high-throughput screening by acquiring luminescence images of the individual cells at appropriate magnification so as to capture their individual images. This is followed by high-content detection within the responding wells using a set of luminescent reagents with different physiological and spectral properties, scanning the array of individual cells to obtain luminescence signals from the luminescent reporter molecules in the cells, converting the luminescence signals into digital data and utilizing the digital data to determine the distribution, environment or activity of the luminescent reporter molecules within the individual cells.

The cassette, which comprises of the non-uniform micro-patterned array of the individual cells and the chamber is inserted into a VSOM optical reader instrument. The optical reader instrument is an optical-mechanical device that handles the cassette, controls the environment (e.g., the temperature, which is important for live cells), controls delivery of solutions to wells, and analyzes the luminescence emitted from the array of cells, one or more cells at a time. The instrument controls the addition of the solutions automatically according to the optical signal(s) from the individual cells and an algorithm. In a preferred embodiment, the optical reader instrument comprises an integrated circuit inspection station using a fluorescence microscope as the reader and microrobotics to manipulate the cassettes. A storage compartment holds the cassettes, from where they are retrieved by a robotic arm that is controlled by computer. The robotic arm inserts the cassette into the luminescence reader. The cassette is removed from the luminescence reader instrument by another robotic arm, which places the cassette into a second storage compartment.

Systems integrating environmental control, micro-robotics and optical readers are produced by companies such as Carl Zeiss [Jena, GmbH]. In addition to facilitating robotic handling, fluid delivery, and fast and precise scanning, two reading modes, high content and high throughput are supported. High-content readout is essentially the same as that performed by the ArrayScan reader (U.S. application Ser. No. 08/810,983, now U.S. Pat. No. 5,989,835). In the high content mode, each location on the non-uniform micro-patterned array of cells is imaged at magnifications of 540× or more, recording a sufficient number of fields to achieve the desired statistical resolution of the measurement(s).

In one embodiment, the optical reader instrument comprises an optical-mechanical design that is either an upright or inverted fluorescence microscope which comprises a computer-controlled x,y,z-stage, a computer-controlled rotating nosepiece holding a low magnification objective (e.g., 0.5×) and one or more higher magnification objectives, a white light source lamp with excitation filter wheel, a dichroic filter system with emission filters, and a detector (e.g., cooled charge-coupled device). In an alternate embodiment, the optical reader instrument can utilize a scanned laser beam in either confocal or standard illumination mode. Spectral selection is based on multiple laser lines or a group of separate laser diodes, as manufactured by Carl Zeiss (Jena, GmbH, Germany) or as discussed in Denk, et al. (Science 248:73, 1990). Another embodiment of the high throughput screening mode involves the use of a low-resolution system consisting of an array (1×8, 1×12, etc.) of luminescence exciters and luminescence emission detectors that scans subsets of the wells on a non-uniform micro-patterned array of cells. In a preferred embodiment, this system consists of bundled optical fibers, but any system that directs luminescence excitation light and collects luminescence emission light from the same well will suffice.

B. Local, Host Computer (or Client)

The computer-controlled peripherals can be independently controlled by the local computer, or the local computer can serve as a conduit for instructions issued by a remote computer. Remote control of generic "instruments" or microscopes or VSOM systems over the Internet has several advantages as discussed below. For instance, a central computer can have greater processing power, archival capacity, and more sophisticated database and other software packages, which do not then need to be duplicated, at great expense on a much greater number of local computers located near individual optical platforms.

C. Remote Computer, Network Software, Database, Informatics, and Analysis Algorithms for VSOM Control From a computer science perspective, various components were needed to produce the present invention. In particularly preferred embodiments, the following components were involved: (1) computer control of the microscope peripherals; (2) segmentation of cells imaged on single or multiple channels; (3) annotation of the recipe used in a particular experiment; (4) automated analysis of cell responses as a function of applied stimuli; (5) offline correlation, clustering and learning techniques that compare the differences between two cell types as a function of an assay; and (6) on-line learning techniques for dynamic control and estimation of a policy (i.e., a protocol or recipe) to elicit direct responses from two or more different cell types. The interaction between various system components is shown in FIGS. 1 and 2. In particularly preferred embodiments, complete integration of all system components included a specifically-designed graphical user interface (GUI), on-line image analysis software, database integration for off-line analysis, effective visualization of cell responses in the model system, and off-line and on-line learning techniques (e.g., algorithms).

In addition, in alternative embodiments, the present invention provides an imaging bioinformatic system for visual servoing optical microscopy (i.e., "BioSig"). These embodiments of the present invention provide the foundation of cataloging cellular responses as a function of specific conditions and stimulations for VSOM experiments. The present invention provides the system architecture, functional data models for representing experimental protocols, novel algorithms for image analysis, and statistical analysis. The architecture provides remove shared operation of at least one VSOM instrument, and couples instrument operation with image acquisition and annotation. In preferred embodiments, the information is stored in an object-oriented database that allows persistent storage of objects and their relationships. In particularly preferred embodiments, the algorithms extract physiological information from individual cells at a subcellular level and map it to cell responses and eventual biological consequences.

The VSOM system in some preferred embodiments, uses a workflow model to periodically capture images, segment those images, measure cellular responses for a field of several hundred cells, and log those responses into an archival system. These responses allow directed measurement and tracking of individual cell responses. The archival system can then be browsed and queried through a web-based interface. Examples include browsing raw data, segmentation results, and corresponding metadata (e.g., computed responses over a 2.5 hour period).

A significant hurdle overcome by the present invention involves the fact that biological experiments require large population studies and correlation of distant features with annotation data. The present invention provides an imaging bioinformatics system for integrated image acquisition, annotation, and hierarchical image abstraction, to create databases that register location and expression information about multiple targets, along with positional references and morphological features. Statistical and visualization tools are integrated to allow hypothesis testing and data mining. This is achieved by leveraging and extending an infrastructure developed for telemicroscopy (See e.g., Parvin et al., "DeepView: A Channel for Distributed Microscopy and Informatics,"

IEEE Conf. on High Performance Computing and Networking [1999], and Parvin et al "Declarative Flow Control for Distributed Instrumentation," IEEE Int. Symposium on the Grid and Cluster Computing, May 2001). The present invention provides various novel components, including but not limited to a distributed architecture for imaging, novel algorithms for characterizing structure and functions at sub-cellular levels, archiving the response of each cell to a particular stimulation and using computed responses to drive the instrument into a specific state.

D. Informatics

In particularly preferred embodiments, the informatic system comprises a data model, presentation manager, and a query manager. These subsystems are decoupled for ease of development, testing, and maintenance. The purpose of the data model component is to capture required annotation data and couple them to computed representation of images for hypothesizing signalling and response pathways. The model is object-oriented and allows bidirectional tracking of annotation and measured feature data. The presentation manager provides at least two distinct features, including mapping between the data model and the user interface, so that hard-wiring the user interface is avoided and facilitating a more flexible interface that is constructed at run time, regardless of changes in the underlying data model. In addition, display functionality of a particular query in either text or graphics is provided. The query manager maps high level user queries to the Java objects that implement the data model. Thus, in preferred embodiments, the present invention simplifies and hides detailed manipulation of the database from the end users.

1. Data Model

Figure 6:
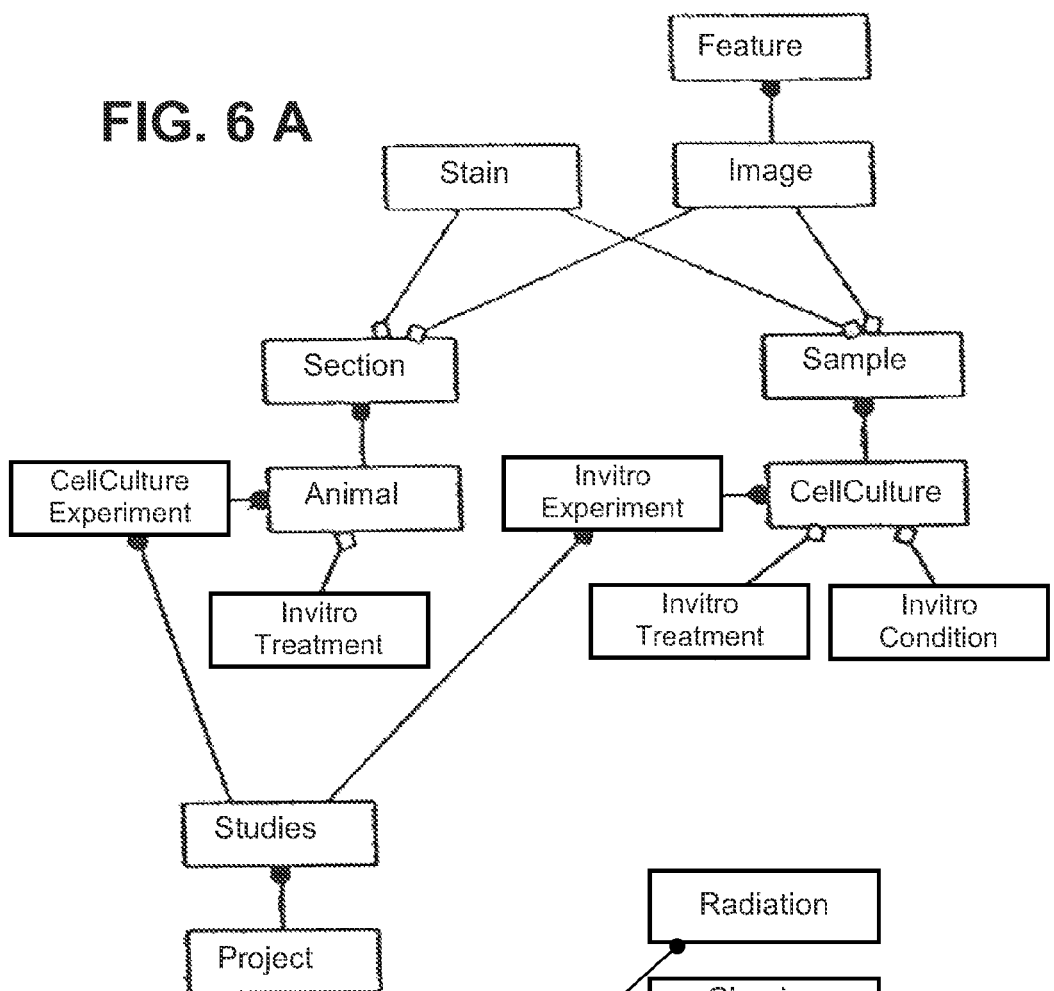
FIG. 6 provides two data models. Panel A provides a complete data model for the bioinformatic system, while Panel B provides a detailed breakdown for in vivo treatment.
Figure 6:
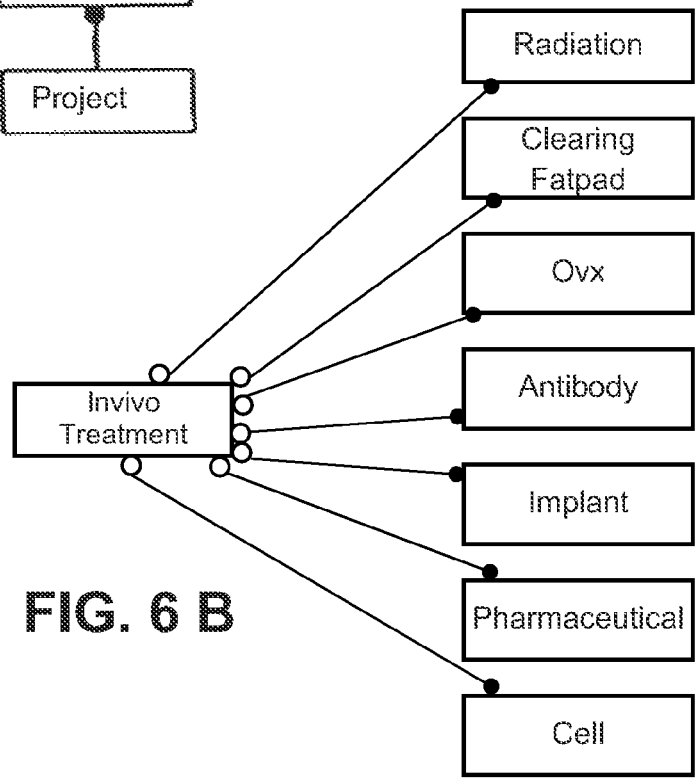

The data model shown in the embodiment presented in FIG. 6, Panel A is object-oriented and links a particular project to computed features from a collection of images. This link is bidirectional to allow tracking of information from any end point. Each project has its own database, which is linked to studies.

2. Presentation Manager

The presentation manager has two major features, namely browsing the database and visualizing the result of a query function. Browsing the database is performed against a predefined schema that captures annotation data, images, and corresponding features. The data model, shown in Panel A of FIG. 6, is represented in XSD (XML scheme) and the presentation manager constructs a view into the database using this representation and the corresponding style sheets (XSL) for browsing and updating. In this embodiment, hardwiring of a GUI is bypassed in favor of a more flexible and dynamically generated user interface. In general, such a mapping could create a complex implementation issue. However, the present invention simplifies the presentation system to allow browsing and updating one layer at a time. A "layer" refers to navigation between an object and other objects that are linked through association, aggregation, and inheritance.

In one embodiment, each scientific experiment may include up to many images that correspond to a population of cells at a specific point in time. It is often necessary to visualize a collection of images, at each time point, with a few images (2-3) that characterize the average behavior of that set. The average behavior is often expressed in terms of a particular feature. The present invention allows construction of a sequence of images, where each image corresponds to a representative of a collection of images at a given time point. Additionally, the presentation manager can display the result of a query function in either text or graphics. The graphics include dose-response plots and scatter diagrams of computed features as a function of independent variables.

3. Query Manager

The query manager provides a set of predefined operators to assist in visualization and hypothesis testing. These operators aid in the drawing of contrast between computed features and their corresponding annotation data, and perform a variety of statistical measures, such as analysis of variance and principal component analysis. In some embodiments, these operators allow cell responses to be deciphered for an eventual model reconstruction. The object-oriented database simplifies measurements such as analysis of variance, since each computed feature has to be mapped to its source (e.g., cell culture or animal). An example of such a high level operator includes correlation of a particular computed feature(s) with respect to independent variable(s). The present invention provides a visual query interface for mapping user queries to a set of database operations, computing the result, and transmitting them to a display manager. In some embodiments, the actual computation includes analysis of variance (e.g., for relating a particular measurement against a number of independent samples) or principal component analysis (PCA) (e.g., for reducing the dimensionality of a computed feature vector) for display purposes.

4. Extraction of Nuclei

Figure 7:
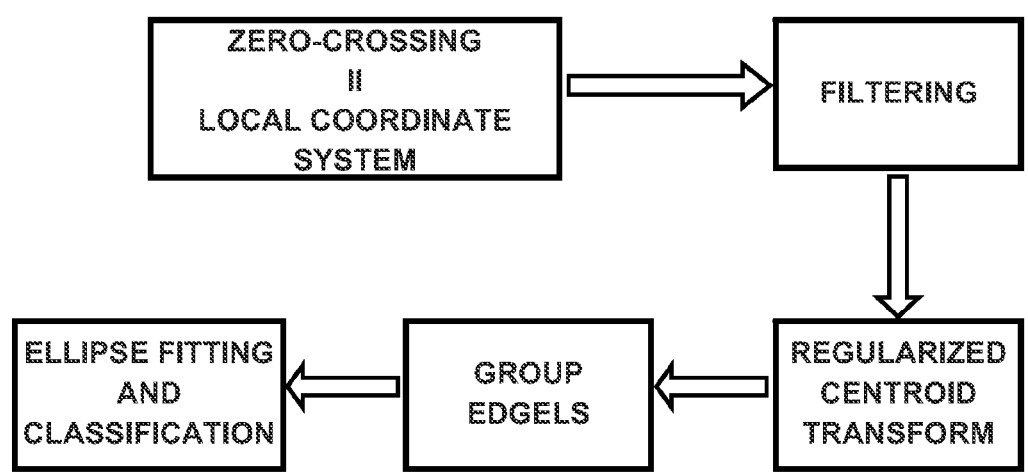
FIG. 7 illustrates the segmentation process. Panel A provides a protocol for extracting an individual nucleus from tissue and cell culture. Panel B provides a demonstration of centroid transform with two adjacent nuclei.
Figure 7:
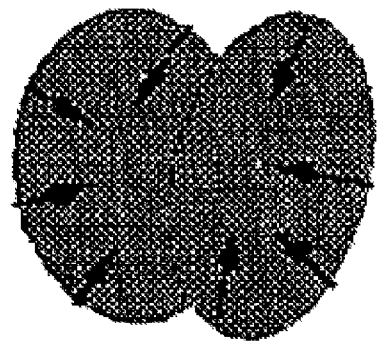

Automatic delineation of subcompartments of cells is an important step in monitoring the responses of cells to applied stimuli. In some cases, cells of interest may overlap or touch each other; thus, making segmentation difficult. Prior approaches utilized in the development of the present invention (See e.g., Cong and Parvin, Patt. Recog., 33:1383-1393 [2000]; and Parvin et al., "Biosig: A Bioinformatic System for Studying the Mechanism of Inter-Cell Signalling," IEEE Inter. Sympos. Bio-Informatics Biomed. Engineer., pages 281-288 [2000]) used both step and roof edges to partition a clump of nuclei in a way that is globally consistent. Step edges correspond to the boundaries between nuclei and background, while roof edges correspond to the boundary between neighboring nuclei. A unique feature of this system was in hyperquadric representation of each hypothesis and the use of this representation for global consistency. Global consistency was obtained through a cost function that was minimized with dynamic programming. The present invention provides approaches that are simpler, as well as more robust. The main difficulty with the earlier approach was that detection and grouping of crease boundaries increased system complexities, resulting in a reduction in reliability. The present invention is also model-based in that the projection of each nucleus is assumed to be quadratic in the image space. However, instead of grouping step and roof edges, some preferred embodiments of the present invention initiate from a representation that corresponds to the zero crossing of the image. The zero crossing image is then filtered with geometrical and illumination constraints to form a binarized clump of nuclei. Each clump is then partitioned into several nuclei through a process referred to as "centroid transform." The steps in the computational protocol are shown in FIG. 7, Panel A. The centroid transform essentially projects each point along the contour into a localized center of mass. The solution is regularized to eliminate noise and other artifacts along the contour, as shown in FIG. 7, Panel B.

a. Edge Detection

The basis for localizing edges is the zero crossing in the local coordinate system. As discussed in greater detail below, these edges correspond to the minimization of supremum.

Most regularization techniques for smoothing are based on minimizing an integral such as $\int_R |\nabla f|^2$. However, this formulation has no control in the local property of $f$. In other words, the global average of $|\nabla f|$ may be small, but locally f may change sharply. A way to overcome this issue to minimize $|\nabla f|$ at every point, which leads to minimization of the supremum of $|\nabla f|$. Thus, the functional $H(f)=\sup_R |\nabla f|$ is considered to be a "limit" of the sequence of functionals (Equation 1):

$$H_N(f) = \left( \int_R |\nabla f|^{2N} dx \right)^{\frac{1}{2N}}, N = 1, 2, 3, \ldots$$

The Euler equation for the minimization of the functional $H_N(f)$ can be expressed as (Equation 2):

$$|\nabla f|^{2(N-2)} \left\{ \frac{1}{2(N-1)} |\nabla f|^2 \nabla f + f_x^2 f_{xx} + 2 f_x f_y f_{xy} + f_y^2 f_{yy} \right\} = 0$$

where a subscript indicates a derivative, such as:

$$f_x = \frac{\partial f}{\partial x}, f_{xy} = \frac{\partial^2 f}{\partial x \partial y}$$

By removing the first coefficient and letting $N \to \infty$, we have Equation 3:

$$f_x^2 f_{xx} + 2 f_x f_y f_{xy} + f_y^2 f_{yy} = 0$$

Equation (3) is called the Infinite Laplacian Equation (ILE), which has been studied widely (See e.g., Aronsson, Arikv. Matematik, 6:551-561 [1966]; Aronsson, Arikv. Matematik, 7:133-151 [1967]; Aronsson, Manuscripta Math., 41:133-151 [1981]; and Evans, Electron. J. Different. Equat., [http://, followed by, ejde.math.swt.edu/Volumes/1993/03-Evans/abstr, followed by, .html] 3:1-9 [1993]). Some important properties of Equation (2) are that there is at most one solution, and if the "solution" is redefined in a suitable weak sense, then a continuous solution to $C^1$ does exist. Also, the trajectory of the gradient of $f$ is either a convex curve or a straight line, and there are no stationary points $|\nabla f|=0$ in R. It is interesting to note that Equation (3) is equivalent to the zero-crossing ($f_{xx}+f_{yy}=0$) in the local coordinate system, where the local coordinate system is defined by $\nabla f$.

Application of Equation (3) to the raw data produces a zero crossing map that is more stable than the laplacian form (i.e., there is no leakage between foreground and background). This zero crossing map has closed contours with false regions that can easily be filtered with intensity and size constraints. The filtered segmented image is then used for centroid transform.

b. Tensor-Based Feature Analysis

Vector field analysis is a well-studied technique in computer vision and pattern recognition, as well as other classic fields such as mathematics and physics. Many concepts and tools have been developed for motion-based applications. The present invention extends the current state of the art to segmentation and interpretation of scientific images. Given an intensity image $f_0(x, y)$, there exists a natural vector field derived from the intensity image, which corresponds to the gradient field rotated by $\pi/2$:

$$v = (-\partial f_0/\partial y, \partial f_0/\partial x)$$

The problem here is that the vector field "v" is noisy, and some type of regularization needs to be introduced. This can be expressed as:

$$\min_u \iint \|u-v\|^2 + \alpha^2 \|\nabla u\|^2 dx dy,$$

where u is the regularized vector field. An elliptic PDE (partial differential equation) can then be solved iteratively. A first order approximation can be computed by a simple linear (Gaussian) scale space model (Lindeberg, J. Appl. Stat., pages 225-270 [1994]):

$$f(\bullet; t) = g(\bullet; t) * f_0(\bullet),$$

where $$g(x,y;t) = (1/2\pi t) e^{-x^2+y^2/4t}$$

is the Gaussian kernel with standard deviation $\sigma = \sqrt{2t}$.

Singularities of the vector field then provide a compact abstraction for the dense vector representation. These singularities can be characterized by point or linear features. Point features include vortices and saddle points. Once these patterns are detected, the corresponding objects can be extracted. Rao and Jain (IEEE Trans. Patt. Anal. Mach. Intell., pages 225-270 [1994]) used local Jacobian for feature extraction from the underlying vector field to detect singularities. However, the approach of the present invention is more robust and provides a measure for the size of the vortex as well. The vortex size complements localization of convex blobs, even though they are connected or touching one another. This is based on Jordan index, to localize singularities in the underlying vector field. Let $F=(u,v)$ be a vector field and J be a Jordan curve with no critical point on it. The index of J is defined by:

$$\text{Index}(J) = 1/2\pi \oint u dv - v du / u^2 + v^2$$

At each point P, a small circle of radius R (denoted by $J^R_P$) around P is chosen, and the Index($J^R_P$) is computed. The flow field (u,v) can then be classified according to:

1. The index of a vortex is equal to +1 (i.e., the classification of singular points in a vector field is given in Rao and Jain, supra), and
2. The index of a saddle point is equal to −1.

There is no node in the vector field because its divergence is zero everywhere:

$$\text{div } v = \partial/\partial_x(-\partial_f/\partial_y) + \partial/\partial_y \partial_f/\partial_x = 0$$

The vortex size is then estimated by a simple search technique. If a point a (x,y) is a vortex, then its size $R^*(x,y)$ can be defined as:

$$R^*(x,y) = \max \{R | \text{Index}(J^R_{(x,y)}) = 1\}$$

In other words, $R^*(x,y)$ is the largest R such that the index of $J^R_{(x,y)}$ remains 1. Being an integral of the first order partial derivatives, the Jordan index is, in some sense, a function of the intensity image. In contrast, other techniques are based on high order derivatives, which are bound to be more noisy. Various Figures (not provided) show the result of vortices and region segmentation on a synthetic image, nuclei labeled with fluorescent dye, and cells observed with transmission light.

In experiments conducted during the course of the present invention, results on the nuclei of living and lysed cells labeled with the fluorescent dye Hoechst 33342 were demonstrated. For example, results on living cells imaged using a 20× phase contrast objective and transmitted light were demonstrated. The later result is significant because current techniques in localizing individual cells are limited to fluorescent imaging, which adds a layer of complexity to the design of dynamic experiments. The results on living cells imaged using a 20× phase contrast objective were the only digital images that were not acquired using a 10× NA 0.5 Zeiss Fluar objective. All images were 1024×1024, and the CCD chip in the camera had pixels of 6.8×6.8μ. Thus, all images taken at 10× show a field of view that is approximately 700μ high and 700μ wide.

C. Regularized Centroid Transform

Let $I(x, y)$ be the original intensity image. At each point $(x_0, y_0)$, its equal-height contour is defined by Equation 4:

$$I(x,y)=I(x_0,y_0)$$

Expanding and truncating the above equation using Taylor's series produces the following estimation (Equation 5):

$$I_x u + I_y v + \frac{1}{2}[I_{xx}u^2 + 2I_{xy}uv + I_{yy}v^2] = 0$$

where $u=x-x_0$, and $v=y-y_0$, or in the following standard form (Equation 6)

$$\frac{1}{2}w^T A w + b^T w = 0$$

where $$A = \begin{pmatrix} I_{xx} & I_{xy} \\ I_{xy} & I_{yy} \end{pmatrix}_{(x_0,y_0)}$$

A is the Hessian matrix, $$b = \begin{pmatrix} I_x \\ I_y \end{pmatrix}_{(x_0,y_0)}$$

b is the gradient of intensity, and $w=(u, v)^T$ is the centroid in the local coordinate system. It is well-known that the centroid of the quadratic curve defined by Equation (6) satisfies the following linear constraint (Equation 7):

$$Aw+b=0$$

If A is non-singular, then the centroid can be determined directly (i.e., Equation 8):

$$w=-A^{-1}b$$

However, this is not always true, and in general, the zero set defined by Equation 9:

$$\begin{vmatrix} I_{xx} & I_{xy} \\ I_{xy} & I_{yy} \end{vmatrix} = I_{xx}I_{yy} - I_{xy}^2 = 0$$

is non-trivial. In addition, it can be further classified into two categories:
1. uniform regions, which correspond to regions where the gradient of intensity is zero. For binary images, information exists only along the contour; and
2. non-uniform regions, which correspond to elliptic features in the gray level image.

The centroids at these points are not well defined Furthermore, from the point of view of computational stability, those points nearby cannot be reliably computed because of the singularity. In order to deal with these difficulties, the problem needs to be regularized. Suppose the centroid at $(x, y)$ is denoted by $(u(x, y), v(x, y))^T$, the regularized model can be formulated as Equation 10 or Equation 11 below:

$$\min E(u,v) = \tfrac{1}{2} \iint \|A \cdot (u,v)^T + b\|^2 + \alpha(\|\nabla u\|^2) dx dy \qquad \text{(Eq. 10)}$$

or $$\min E(u,v) = \tfrac{1}{2} \iint (I_{xx}u + I_{xy}v + I_x)^2 + (I_{xy}u + I_{yy}v + I_y)^2 + \alpha(u_x^2 + u_y^2 + v_x^2 v_y^2) dx dy \qquad \text{(Eq. 11)}$$

where the first and second terms are the error of estimation, the third term is the smoothness constraint, and $\alpha$ (>0) is the weight. The solution to this problem is referred to as "Regularized Centroid Transform" (RCT). The Euler-Lagrange equations of the variational problem Equation 11 are (Equation 12):

$$\begin{cases} I_{xx}(I_{xx}u + I_{xy}v + I_x) + I_{xy}(I_{xy}u + I_{yy}v + I_y) - \alpha(u_{xx} + u_{yy}) = 0 \\ I_{xy}(I_{xx}u + I_{xy}v + I_x) + I_{yy}(I_{xy}u + I_{yy}v + I_y) - \alpha(v_{xx} + v_{yy}) = 0 \end{cases}$$

Substituting the finite difference approximations of partial derivatives into the above partial differentiation equations, results in Equation 13:

$$\begin{cases} I_{xx}[I_{xx}u(x,y) + I_{xy}v(x,y) + I_x] + I_{xy}[I_{xy}u(x,y) + I_{yy}v(x,y) + I_y] - \\ \alpha[u(x+1,y) + u(x-1,y) + u(x,y+1) + u(x,y-1) - 4u(x,y)] = 0 \\ I_{xy}[I_{xx}u(x,y) + I_{xy}v(x,y) + I_x] + I_{yy}[I_{xy}u(x,y) + I_{yy}v(x,y) + I_y] - \\ \alpha[v(x+1,y) + v(x-1,y) + v(x,y+1) + v(x,y-1) - 4v(x,y)] = 0 \end{cases}$$

which can be re-written as Equation 14:

$$\begin{cases} a \cdot u(x,y) + b \cdot v(x,y) = e \\ c \cdot u(x,y) + d \cdot v(x,y) = f \end{cases}$$

where (Equation 15):

$$a = I_{xx}^2 + I_{xy}^2 + 4\alpha$$

$$b = c = I_{xx}I_{xy} + I_{xx}I_{yy}$$

$$d = I_{xy}^2 + I_{yy}^2 + 4\alpha$$

$$e = -I_xI_{xx} - I_yI_{xy} + \alpha[u(x+1,y) + u(x-1,y) + u(x,y+1) + u(x,y-1)]$$

$$f = -I_xI_{xy} - I_yI_{yy} + \alpha[v(x+1,y) + v(x-1,y) + v(x,y+1) + v(x,y-1)]$$

All of these coefficients are the functions of partial derivatives and the neighborhood of $(u(x, y), v(x, y))$. The determinant (Equation 16):

$$\Delta = ad - bc > 16\alpha^2$$

is always positive, and the solution to Equation (14) is Equation 17:

$$\begin{cases} u(x,y) = \dfrac{de-bf}{\Delta} \\ v(x,y) = \dfrac{-ce+af}{\Delta} \end{cases}$$

Hence, a new set of estimates ($u^{n+1}$, $v^{n+1}$) from the estimated partial derivatives ad the previous estimates ($u^n$, $v^n$) by Equation 18:

$$\begin{cases} u^{n+1}(x,y) = \dfrac{d''e'' - b''f''}{\Delta''} \\ v^{n+1}(x,y) = \dfrac{-c''e'' + a''f''}{\Delta''} \end{cases}$$

e. Representation and Classification

The imaging of living cells, and fluorescence microscope imaging in general, is often multispectral for separating structural and functional information. In some embodiments, a sample is tagged with fluorescent dye and imaged at 360 nm, to reveal nuclear formation (e.g., shape and organization). Responses are imaged at other excitation frequencies (e.g., 490 nm and 570 nm). In some embodiments of the present invention, each nucleus is represented with an ellipse, as well as hyperquadrics, and its response is read directly from other channels.

The ellipse fit is based on estimating the parameters of polynomial F (a, x)=$ax^2+bxy+cy^2+dx+ey+f$, subject to the constraint that $4ac-b^2=1$ (Fitzgibbon et al., Proc. Intl. Conf. Patt. Recogn., 253-257 [1996]).

A 2D hyperquadric (Hanson, Comp. Vision Graph. Image Proc., 44:191-210 [1988]; and Kumar et al., IEEE Trans. Patt. Anal. Mach. Intell., 17:1079-1083 [1995]), is a closed curve defined by Equation 19:

$$\sum_{i=1}^{N} |A_i x + B_i y + C_i|^{\gamma_1} = 1$$

Since $Y_i > 0$ (Roskelley et al., Curr. Opin. Cell Biol., 7:736-747 [1995]) implies that (Equation 20):

$$|A_i x + B_i y + C_i| \leq 1 \forall i = 1, 2, \ldots, N$$

which corresponds to a pair of parallel line segment for each i. These line segments define a convex polytope (for large Y) within which the hyperquadric is constrained to lie. This representation is valid across a broad range of shapes which need not be symmetric. The parameters $A_i$ and $B_i$ determine the slopes of the bonding lines and, along with $C_i$, the distance between them $Y_i$ determines the "squareness" of the shape.

The fitting problem is as follows. Assume that m data points $p_j = (x_j, y_j)$, j=1, 2, ..., m from n segments ($m = \Sigma_i^n = 1 m_i$) are given. The cost function is defined as Equation 21:

$$c^2 = \sum_{j=1}^{m} \dfrac{1}{\|\nabla F_j(p_j)\|^2} (1 - F_j(p_j))^2 + \lambda \sum_{i=1}^{N} Q_i$$

where $$F_j(p_j) = \Sigma_i^N = 11 |A_i x_j + B_i y_j + C_i|^{Y_i},$$

Figure 8:
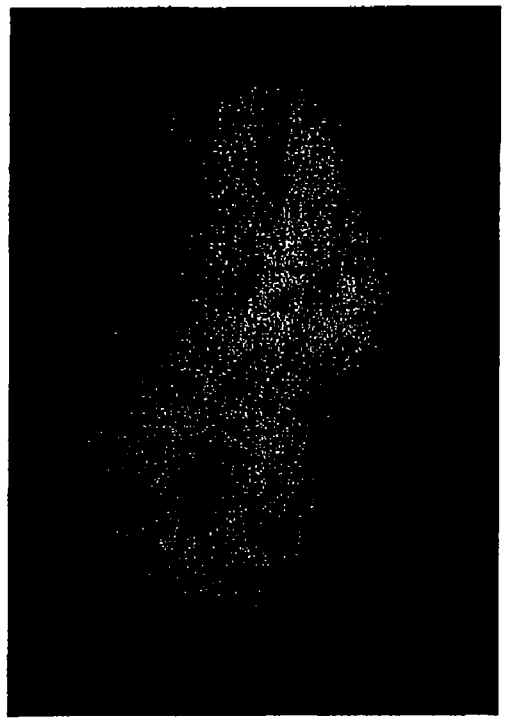
FIG. 8 provides a photograph showing original cells.
Figure 9:
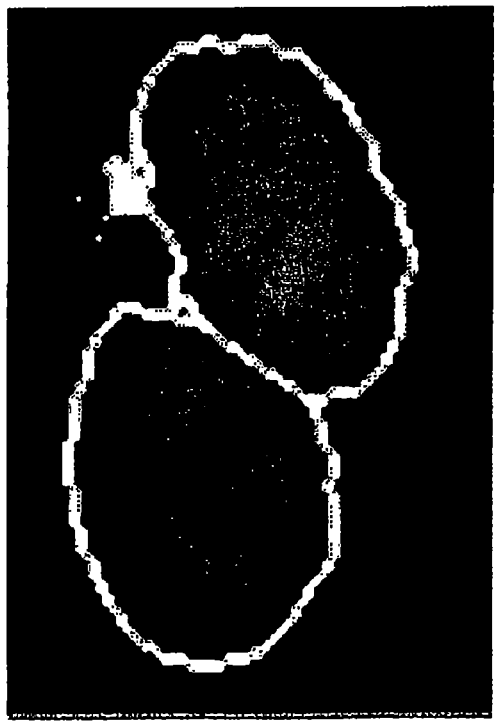
FIG. 9 provides segmentation results for nuclei stained with DAPI.
Figure 10:
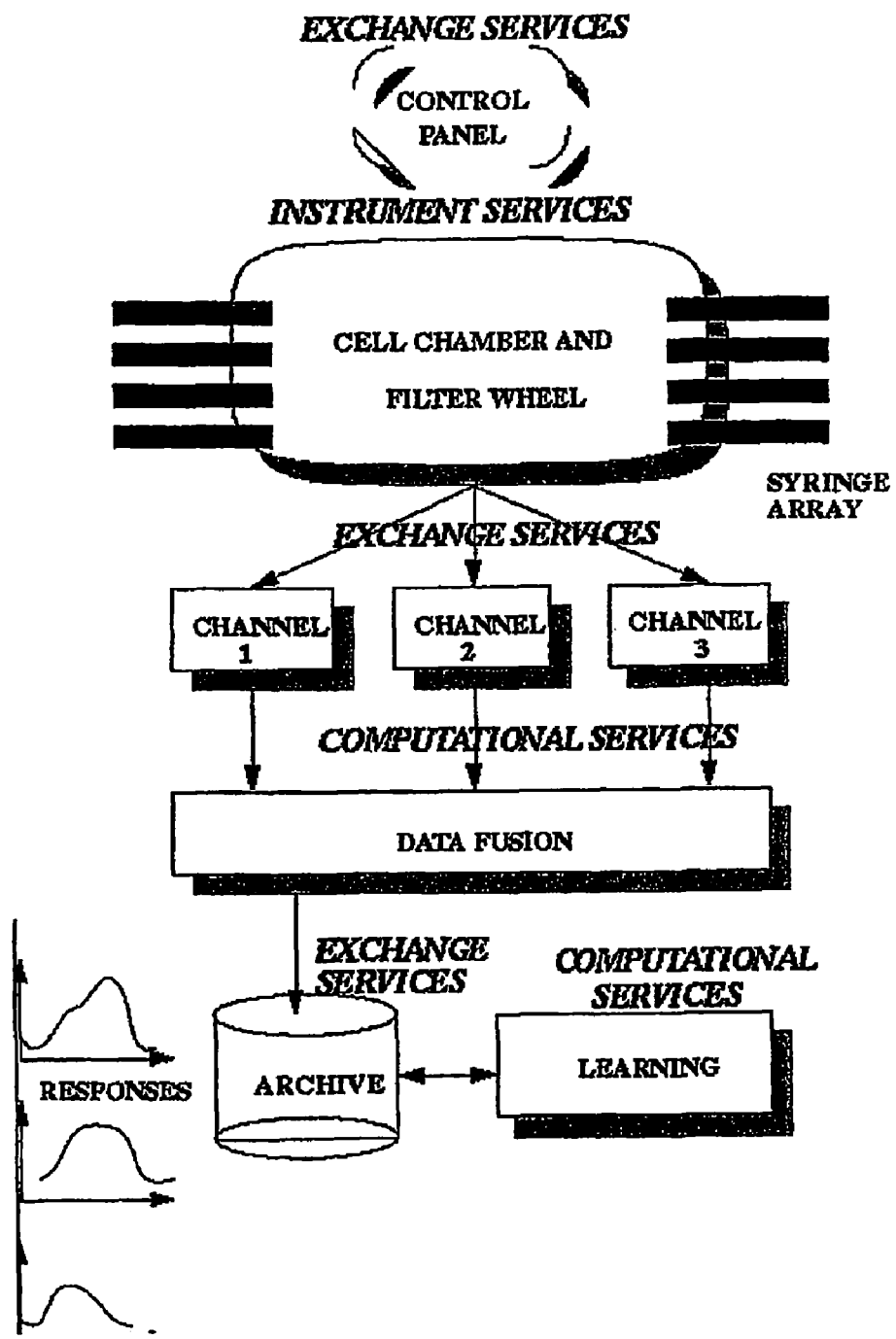
FIG. 10 provides a schematic showing the interaction of various components in one embodiment of the knowledge-based VSOM of the present invention. In this Figure, the italics refer to services defined in the overall system architecture.

$\nabla$ is the gradient operator, $\lambda$ is the regularization parameter, and $Q_i$ is the constraint term (Kumar et al., IEEE Trans. Patt. Anal. Mach. Intell., 17:1079-1083 [1995]). The parameters $A_i$, $B_i$, $C_i$, and $Y_i$ are calculated by minimizing $\epsilon$, using the Levenberg-Marquar non-linear optimization method (Press et al., *Numerical Recipes in C*, Cambridge University Press [1992]), from a suitable initial guess (Kumar et al., IEEE Trans. Patt. Anal. Mach. Intell., 17:1079-1083 [1995]). Each nucleus in the image is further classified with respect to the position in the lumen. FIGS. 8 and 9 show an example of ellipse fitting and classification of nuclei in the image.

f. Analysis of Regularized Centroid Transform

In one embodiment of the present invention, extraction of nuclei in the scene is different than well-known morphological operators. One particular technique is watershed transformation (See e.g., Najman and Schmidt, IEEE Trans. Patt. Anal. Mach. Intell., 18:1163-1173 [1996]), which views the image as a three-dimensional structure. By flooding the image from its local minima and inhibiting merging of the regions that originated from different local minima, the image is partitioned into catchment and basins and watershed lines. In alternative embodiments, such a partition is initiated from edges by finding a downstream path from each edge point to a local minimum. The watershed transformation leads to oversegmentation requiring complex morphological operation to merge adjacent regions. In contrast, preferred embodiments of the present invention initiate from a binarized image followed by collapsing boundary points that belong to a nucleus into a single point. However, from the point of view of moving boundary points into a local basin to reveal a natural partition, watershed and centroid transform share the same idea. Using this method, the energy landscape corresponding to the distance transform shows many local minima. In contrast, regularized centroid transform has a smooth energy landscape with a single local minimum.

The centroid transform essentially partitions a binary blob into distinct convex regions, where each convex region corresponds to a nucleus or another subcompartment Partition is evolutionary and occurs along natural boundaries In contrast, in earlier work conducted during the development of the present invention (See e.g., Cong and Parvin, Patt. Recog., 33:1383-1393 [2000]), such a partition did not necessarily occur along natural object boundaries.

Thus, the present invention provides methods for a bioinformatics approach to microscopy and image analysis useful in building a more detailed picture of the signaling that occurs between cells as a result of various stimuli (e.g., an exogenous applied stimulus) that result in biological responses (e.g., biological functions). These methods are described in greater detail below.

Importantly, the VSOM of the present invention is suitable for interfacing with DeepView, a channel for distributed microscopy and informatics, discussed in greater detail in our previous work. DeepView provides a scalable interface for adding any instrument into its framework. It also provides means for data transfer and viewing over wide area networks. The system has a generic GUI that interacts with the target instrument through advertisement of its properties. In the case of VSOM, related properties are computer-controlled syringes, shutters, and xy stage, a z-axis focus motor, a filter wheel, and camera control parameters. This concept of advertising capabilities (functionalities) of an instrument leads to a more uniform interface and reduces maintenance cost through software reusability.

E. Segmentation

As indicated above, automatic delineation of cell nuclei and cytoplasm is an important step in mapping cell responses into specific cellular compartments. This computational component interacts with the VSOM system to acquire image data from one channel or multiple channels (e.g., by rotating the filter wheel or opening and closing shutters). Segmentation of images from a single channel is described above. A brief overview of multichannel segmentation follows.

Another tedious type of data collection is in the analysis of multichannel images. In this scenario, a cell is imaged with different fluorescent probes and using different excitation filters to accentuate different components of the cells. Here, the system must be able to simultaneously analyze several channels of data, select a specific intracellular and make repeated measurements. An efficient approach to fusion of images based on a Bayesian framework has been developed. This approach can also be extended to 3D (with confocal microscopy), as demonstrated by work performed during the development of the present invention (See, Parvin et al., AAAI Symp. Appln. Comp. Vis. Med. Imaging [1995]). The purpose of data fusion is for complementary processing of different modalities for segmentation and labeling. From this perspective, the segmentation procedure should label each pixel in the data volume accordingly. However, there are a number of ambiguities that can complicate the labeling process. These ambiguities can arise from purely local processing and the absence of any high level feedback.

The sources for the ambiguities include corruption of data by noise, performance limitation of algorithms for extracting local features, and existence of non-essential features that impede the labeling task. One aspect of region segmentation involves estimating the average intensity of each region that is accomplished by the analysis of a histogram. In some embodiments, the initial position of the peaks in the histogram are approximated and then refined with least square approximation. The next step of the computational process is to use these peaks as cluster centers to enforce local consistency in the image space. Here, a Bayesian framework is used to label images based on their multiple channel information. Specifically, the present invention uses a Bayesian hierarchical model with three levels of hierarchy. The first level is a model for the underlying classification, Z. Under ideal conditions, observing Z under M different modalities (e.g., three fluorescence images corresponding to blue, green and red fluorescence emission, respectively) specifies an ideal representation, $X_i$ of the data that are corrupted by different types of noise in the imaging system. The third level of the hierarchy corresponds to the actual observation of data $Y_i$. The first level uses Markov Random Field (MRF) with prior probability density function in the form of Ising model with a positive parameter. This parameter encourages cooperation among nearby pixels. In a Bayesian framework, the assumption may be made that there is prior ignorance about the scene content. The second level models X as conditionally dependent given Z, (i.e., $P(X_1, \ldots, X_M|Z)=P(X_1|Z) \ldots P(X_M|Z)$). This is reasonable, since if a classification is labeled as cytoplasm, than the ideal response of the green channel (i.e., cytoplasm) and the blue channel (i.e., nuclei) will not affect each other. Finally, the third level of hierarchy, $Y_i$ is modeled as a Gaussian distribution. As a result, $Y_i$ will be a locally blurred representation of $X_i$. The full model can be written as Equation 22:

$$P(Z,\{X_i\},\{Y_i\})=\Pi_{i=1}^M P(Y_i|X_i)\Pi_{i=1}^M P(X_i|Z)P(Z)$$

A maximum a posteriori (MAP) estimate is used to obtain $X_i$ and Z. However, since MAP computation is inherently infeasible, a numerical approximation based on iterative conditioning modes (ICM) is used to find the local optimum (See, Besag, J. Roy. Stat. Soc. B, 48:259-302 [1986]).

F. Software

As discussed in greater detail herein, the functional architecture of the VSOM used in the experiments described herein consists of an image-acquisition module, an image-analysis module, servoing, and an archive. The image-acquisition module provides the means for time-lapsed high resolution video microscopy, with six excitation filters. This module has a recipe manager to allow either manual or pre-programmed capture of images at different temporal and excitation frequencies. The recipe is expressed in XML notation that provides semantic interoperability. The analytical module integrates a unique segmentation algorithm that provides a feature-based summary of images based on size, location, response, and the bounding contours. Thus, the analytical module has a pool of unique segmentation algorithms that provide a feature-based summary of images based on an attributed graph model. Accordingly, each node in the graph corresponds to a homogeneous region (e.g., nucleus, cytoplasm, etc.) in the image.

Attributes of each node include the bounding contours, parametric representation of this contour with hyperquadrics, a number of derived features, and the response of subcellular compartments(s) under observation. The links in the graph encode the adjacency relationship between various nodes. The attributed graph model completely expresses the structural definition of each cell and its neighborhood. The servoing module controls the concentration of various compounds in the tissue culture vessel, by controlling the flow in any of the four syringes positioned near the microscope. The servoing provides three operational modes, with each mode subsequently registered with the recipe manager. These modes include (1) a static recipe, in which the flow rate of each compound, its start point in time, and duration are specified; (2) a dynamic recipe mode, in which the flow rate and duration are altered as a function of a particular response of the cells under observation; and (3) a modulating recipe under program control that turns the flow on and off at a specified frequency. The archival system stores the images, their computed graph model, and annotation data in a flat file environment. One major feature of the present invention is that it can be operated remotely from multiple sites. This unique feature allows researchers to collaborate on a given experiment although they are physically located at geographically remote locations.

Figure 14:
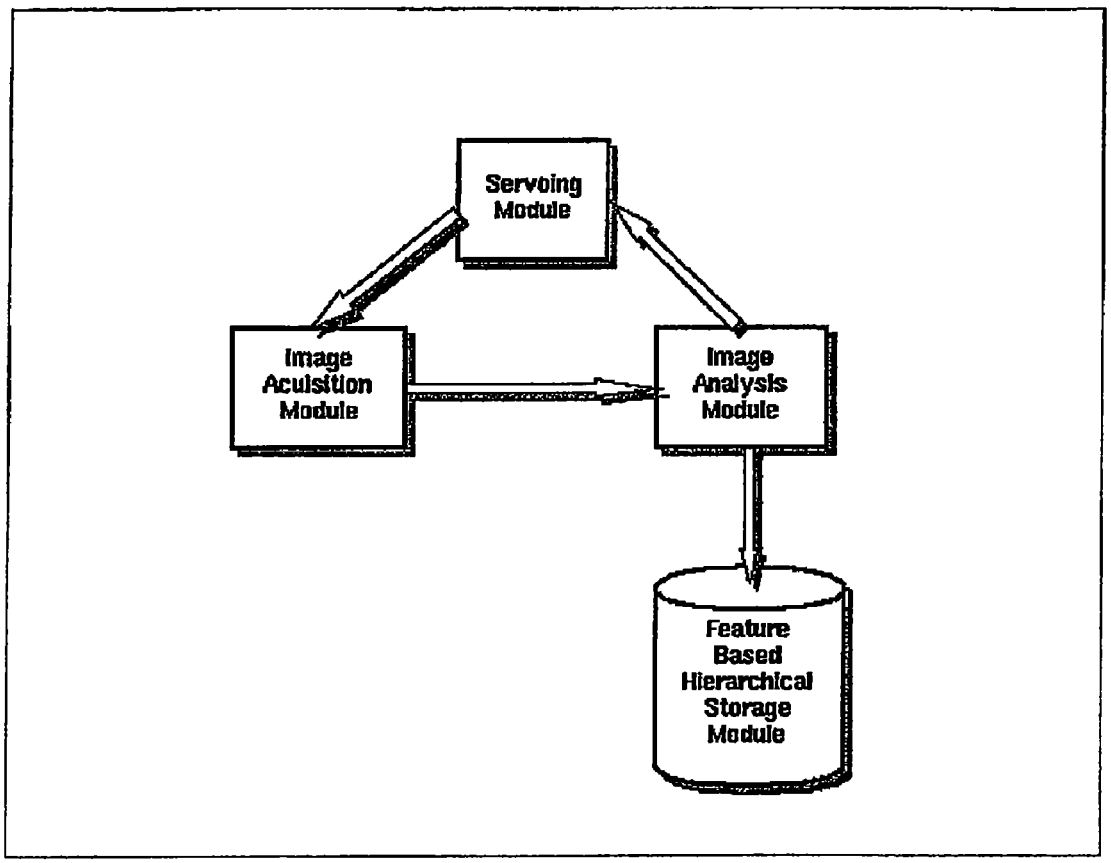
FIG. 14 provides schematics of one embodiment of the present invention. Panel A provides a schematic of the functional architecture of the DeepView Bioinformatics system. Panel B shows an example of a pump log, while Panel C provides an example of an XML recipe file, and Panel D provides an ICS image header.

The present invention maximizes the flexibility available to the users. For example, a user can enter a recipe for a particular experiment that allows for controlling the perfusion rate(s) into the cell chamber, setting camera exposure times, selecting the location of the optical filter wheel, and setting the sampling rate for data collection. One preferred embodiment of the operational VSOM software packages for image acquisition and control is referred to herein as "VX5," while another preferred embodiment is referred to as "ADR." VX5 is designed for static recipe control of the system, while ADR is designed to run dynamic recipe visual-servoing experiments locally or over the network. FIG. 14 provides schematics of the functional architecture of DeepView (Panel A), as well as a sample XML recipe file (FIG. 14, Panel C) for a VX5 run, an example of data found in the pump log (FIG. 14, Panel B), and an example of an ICS digital image header (FIG. 14, Panel D).

G. Feature-Based Image Storage

Figure 15:
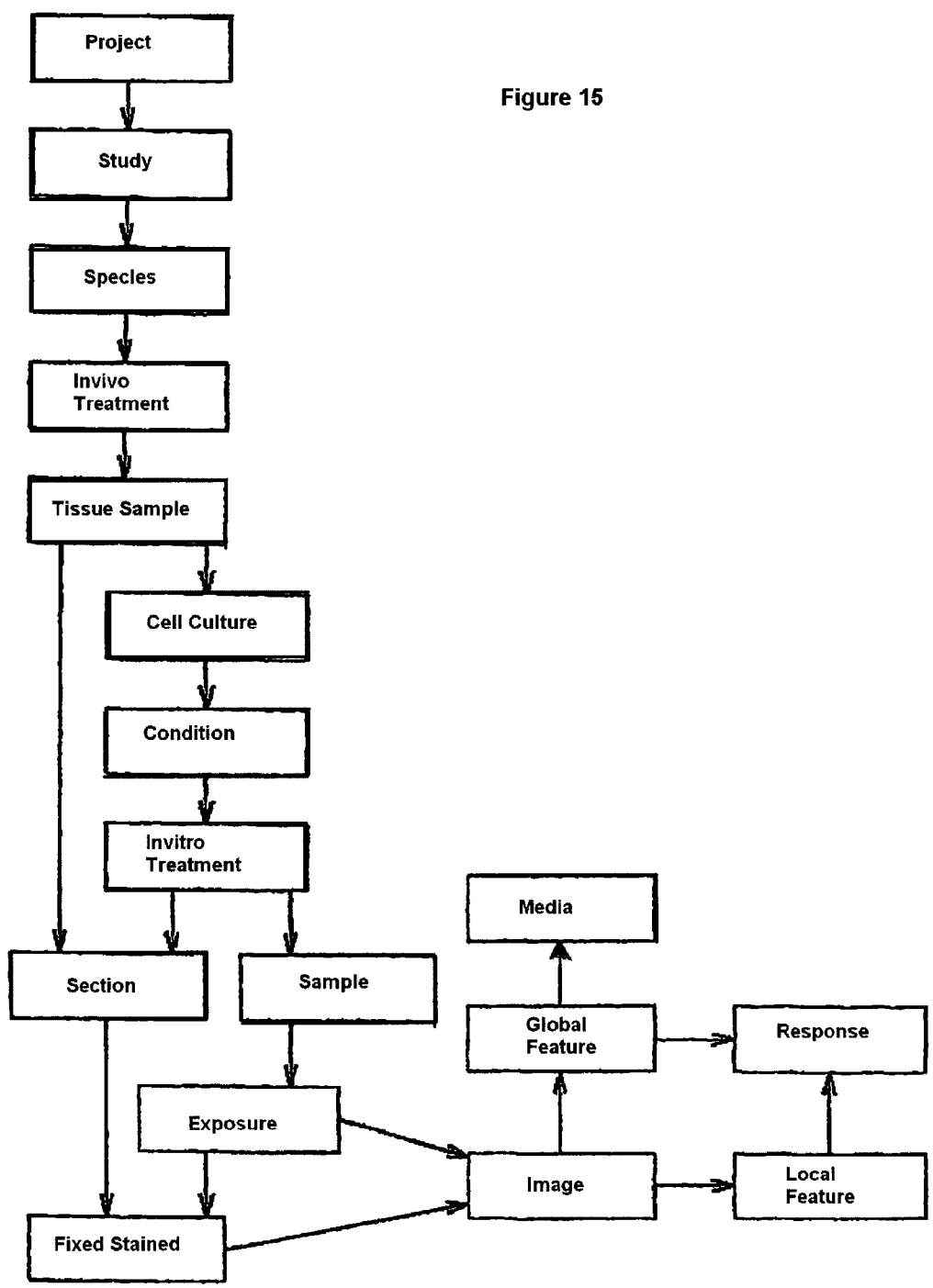
FIG. 15 provides a data model for in vivo and in vitro studies.
Figure 16:
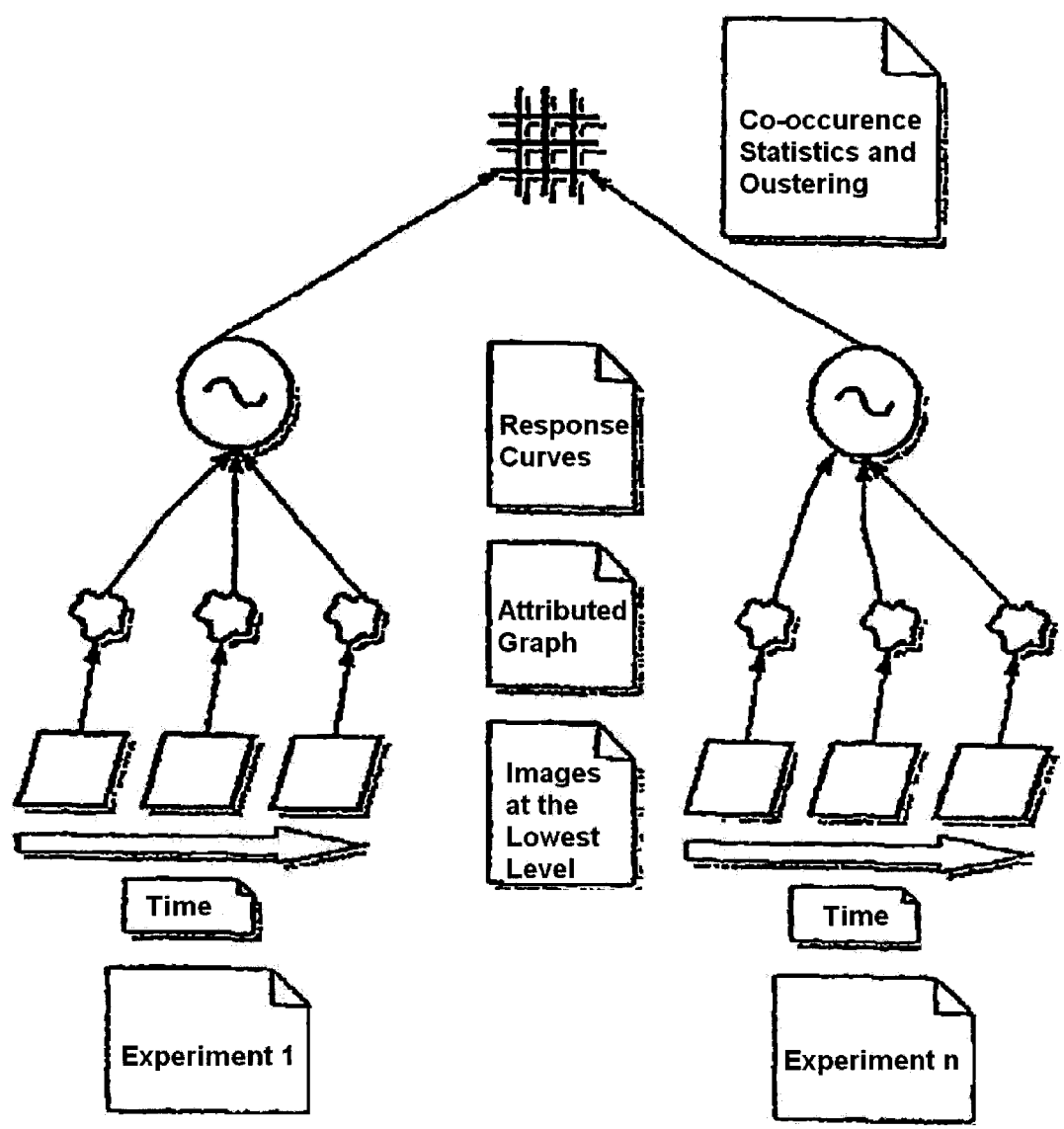
FIG. 16 provides a schematic showing feature-based hierarchal storage of computed structure and function in each compartment of a cell. Each experiment consists of time-lapsed video imaging and the required manipulation of perfusion pumps (not shown). Images are stored at the lowest level. The next level stores the structure and function of the subcellular anatomy as an attributed graph. The third level constructs the corresponding response curves at a specific location and inferred trajectories of the compound. The fourth layer provides a mechanism to construct the transition probabilities together with cross-correlation studies between experiments.

Presently storage models are commonly build on flat files that are difficult to search and maintain. The present invention provides means to leverage an active bioinformatic program to build the required schema for storage handling. A design of a one schema is shown in FIG. 15. This design was extended to accommodate VSOM and to produce a feature-based spatio-temporal database useful for constructing a model of which specific subcellular compartment(s) "respond" to applied stimuli, and to what degree. The multidimensional database shown in FIG. 16 provides a representation of cellular responses, including response curves for each subcellular compartment, and the movement of fluorescent probes from one compartment to the next.

During use of preferred embodiments, each experiment consists of a target frame (i.e., image) that corresponds to a specific physical location in the specimen vessel (e.g., petri dish). The subcellular structures in the cell are segmented and stored as an attribute graph along with the annotation data. The target frame is then observed as a series of digital images collected over time as stimuli are applied to the living cells under computer control. The response in each compartment is recorded and the movement of fluorescent probes is tracked as they move into the cell, or between subcellular compartments.

The functional view of the stored data is hierarchical. At the lowest level, raw images and the corresponding physical annotation of images are stored. At the next level, the attributed graph model (i.e., structure), corresponding responses (i.e., function), and dynamic annotation of environmental conditions (e.g., stimulus type, flow rate, concentration, etc.) are stored. At the next level, the temporal expression of each compartment in a cell is summarized as a response curve along with a trajectory of the compound as it reapportions within different subcellular compartments. These responses may not be similar for all cells under observation. However, it is contemplated that these responses will form clusters, with each cluster corresponding to a group of cells of a particular type, or in a similar physiological state. These clusters must be identified for subsequent correlation studies. Each cluster corresponds to a time series event that corresponds to a particular subcellular compartment of the cells. The average behavior of these responses in each cluster is represented through single value decomposition. Formally, the observed response is a multi-variable function defined as (Equation 28):

$$f_t(\text{Channel}, \text{CellType}, \text{Compartment}, \text{Dye}) = f([\text{Dye}], f/t, \text{Flow}_{ci}/t, T)$$

Where $f$ is the mean fluorescence intensity observed in a specific compartment at time t, [Dye] is the concentration of dye, Channel is the position of the excitation filter, T is temperature, and Flow corresponds to changes in the flow of compounds being injected. Schema are developed to capture this time-varying information to store the observations into a database for subsequent knowledge discovery. Each experimental cycle generates a fingerprint for each observed cell. These individual responses provide a compact representation of intracellular activities in the image space that can be visualized per cell, population of cells, cell types, etc.

H. Learning from Cell Responses

The learning techniques of the present invention are used to optimize and discover cell specific differences between cell types. In this context, computed responses, together with their organization and trajectories aid in development of a model by which subsequent stepwise searches for optimized discriminators of cell types are facilitated. The basis for any learning approach involves a policy, rewards, values, and a model of environment. One purpose of model reconstruction is to evaluate various policies and reward functions. It is contemplated that models will vary from one cell type to another. These variations are significant on their own merit and when quantified, can serve as a valuable validation. The database content provides the basis for evaluation, refinement, and localization of similarity measures. Similarities are measured by analyzing clusters on the basis of state and action. These clusters aid in computation of co-occurrence statistics over different responses for establishment of equivalence classes. Alternatively, a cell response and its corresponding attributes (dynamic annotations) generate a representation within a sequence. This representation is then available for construction of joint occurrence statistics in that sequence, together with transition probabilities. The co-occurrence statistics aid in hypothesizing a binary tree classification of an ensemble of representative features. One utility of this method is in detecting and classifying correlated sequences. Furthermore, once a model is established, co-occurrence statistics provide a means of detecting outliers. The transition probabilities provide the knowledge of environment, which can then be used for reinforcement learning. In addition, means to model cell responses as a time-varying linear system are provided. Linear systems are simple and powerful techniques to characterize the behavior of a system. In this context, a state space representation of the system with variable memory (delay) is constructed and parameters of the associated matrices are estimated and validated.

I. Reinforcement Learning

In this phase, prior knowledge is used as a starting point to learn how to modulate the uptake of a fluorescent probe, an optimize its intracellular uptake in a systematic way. This is often referred to as "reinforcement learning," and in some embodiments, is modeled as a Markov decision process (MDP). A particular MDP is defined by its state (i.e., observed response) and action set that includes modifications of the intracellular concentration of fluorescent probes (e.g., by infusing biological inhibitors, altering the concentrations of physiologicallly important ions in the medium, etc.). The reward in such a system can be measured as the changes—in computed response or its episodic gradient. Furthermore, in some embodiments, the transition probabilities (of MDP) are then computed from observations made from the same assay in the database. These transition probabilities provide the enabling technology for an optimal policy (i.e., schedule). In general, such a policy can be expressed as dynamic programming, Monte Carlo methods, and temporal difference learning. Dynamic programming requires a model of cell response. Such a model is hypothesized from the database. In addition, as the database expands, models become more accessible. Monte Carlo methods do not require a model, but they are not suitable for step-by-step incremental computation. On the other hand, temporal methods require no model and are fully incremental. Nonetheless, all three methods are applicable to embodiments of the present invention. For example, Monte Carlo techniques are applicable for use in one incremental step (i.e., one episode) if sample transition probabilities (not a complete one) exist. Finally, temporal differencing is the combination of Monte Carlo and dynamic programming (i.e., learning directly from raw experience without the model, and then updating estimates based on part on learned estimates).

J. Methods for Rapid Discovery of Physiological Characteristics That Distinguish Malignant and Non-malignant Breast Epithelial Cells Recent advances in the in vitro propagation of primary breast tumor cells allow relatively small numbers of tumor cells harvested from fine-needle aspirates (FNAs) to be passaged and expanded in culture (Li et al., Canc. Res., 58:5271-5274 [1998]). Indeed, a great deal of progress has been made in the primary culture of malignant human breast epithelial cells (BECs) (Band et al., Canc. Res., 50:7351-7357 [1990];

Ethier et al., Canc. Res., 53:627-635 [1993]; Dairkee et al., Canc. Res., 57:1590-1596 [1995]; Tomida and Tsuruo, Anti-Canc. Drug Des., 14:169-177 [1999]; and Brown and Giaccia, Canc. Res., 58:1408-1416 [1998]).

The in vivo environment associated with malignant cells is believed to consist of regions of low oxygen (i.e., hypoxia), low pH, low glucose levels, and high levels of metabolic waste. It has been demonstrated that when these conditions are simulated in culture it is possible to isolate relatively pure populations of primary breast tumor cells (Dairkee et al., supra), as non-malignant cells are unable to survive these hostile environmental conditions in vitro. A common misconception is that malignant BECs proliferate more rapidly than non-malignant cells. Thus, an additional benefit to providing cultures of malignant cells with a harsh environment is that non-malignant epithelium, with its higher proliferation rate, is not present and is not able to overgrow the tumor cells. In addition, drug resistance in tumor cells may depend upon and be the result of the stress of a hostile microenvironment (Tomida and Tsuruo, supra). For this reason, it was contemplated that accurate measurements of drug resistance may require that the assays be performed on cells in the proper microenvironment. Indeed, some of the most successful in vitro chemosensitivity tests involved the culture of cells in tiny capillary tubes that were sealed at both ends and incubated for 14 days. The resultant microenvironment in the tubes is likely to be even more hostile than that generated using the sandwiched coverslip method (See, Dairkee et al., supra).

Moreover, in culture, the resultant cells (up to $10^7$ cells) closely resemble the original tumor and display one or more tumor phenotypes, including growth on soft agar. There is a great deal of interest in the unique physiology of solid tumors. Indeed, it is likely that a suboptimal, nutritionally-depleted environment exists in breast tumors (Dairkee et al., supra; Tomida and Tsuruo supra; and Brown and Giaccia supra). The present invention provides means to improve the culture of primary breast tumor specimens. For example, it is contemplated that tumor and normal cells show very different pH behavior as a function of incubator $CO_2$, levels. In addition, the pH range tolerated by each cell type is likely to vary. The net effect is that there is not a common $CO_2$ level that allows these different cell types (in separate flasks, in the media that each prefers) to simultaneously propagate in a single incubator. Indeed, it is contemplated that normal cells tolerate a much narrower range of pHs than do cancer cells. None of the cell lines was found to prefer a lower pH environment (<7.1).

Thus, if it is true that successful propagation of human tumor breast epithelial cells requires pHs<7.0, then it is also clear why previous in vitro chemosensitivity assays have not been successful. Most media and cell incubation conditions have been designed for pHs>7.0. Thus, when human tumor biopsy specimens are cultured under these conditions, it is the normal cells that attach and proliferate, not the tumor cells. Chemosensitivity tests are then unknowingly conducted on normal cells, rather than the tumor cells. This may be the reason for the previous failure of these assays during clinical trials. However, an understanding of the mechanism(s) is not necessary in order to use the present invention and it is not intended that the present invention be limited to any particular mechanism(s). However, the present invention provides means to monitor, analyze and quantify morphological transformations in normal and abnormal cells as a function of pH and other microenvironmental aspects (e.g., by a VSOM system with the ability to segment cells in transmitted light).

K. Repeated Observation and Analysis of a Particular Field of Cells

The present invention further provides the means to repeatedly observe and image many fields of cells in closed tissue culture flasks, in a manner similar to that described herein for multi-well plates. The ability to segment cells in transmitted light means that cell shapes, locations and relative positions can saved, so that when the flask is returned to the microscope stage, the VSOM system returns to tile same field(s) of cells, acquires new images, and quantifies any morphological changes. This is an example of a more mechanical visual servoing application, where the system relocates the same field of cells, even in situations where cell numbers, relative positions, and shapes had changed.

Figure 17:
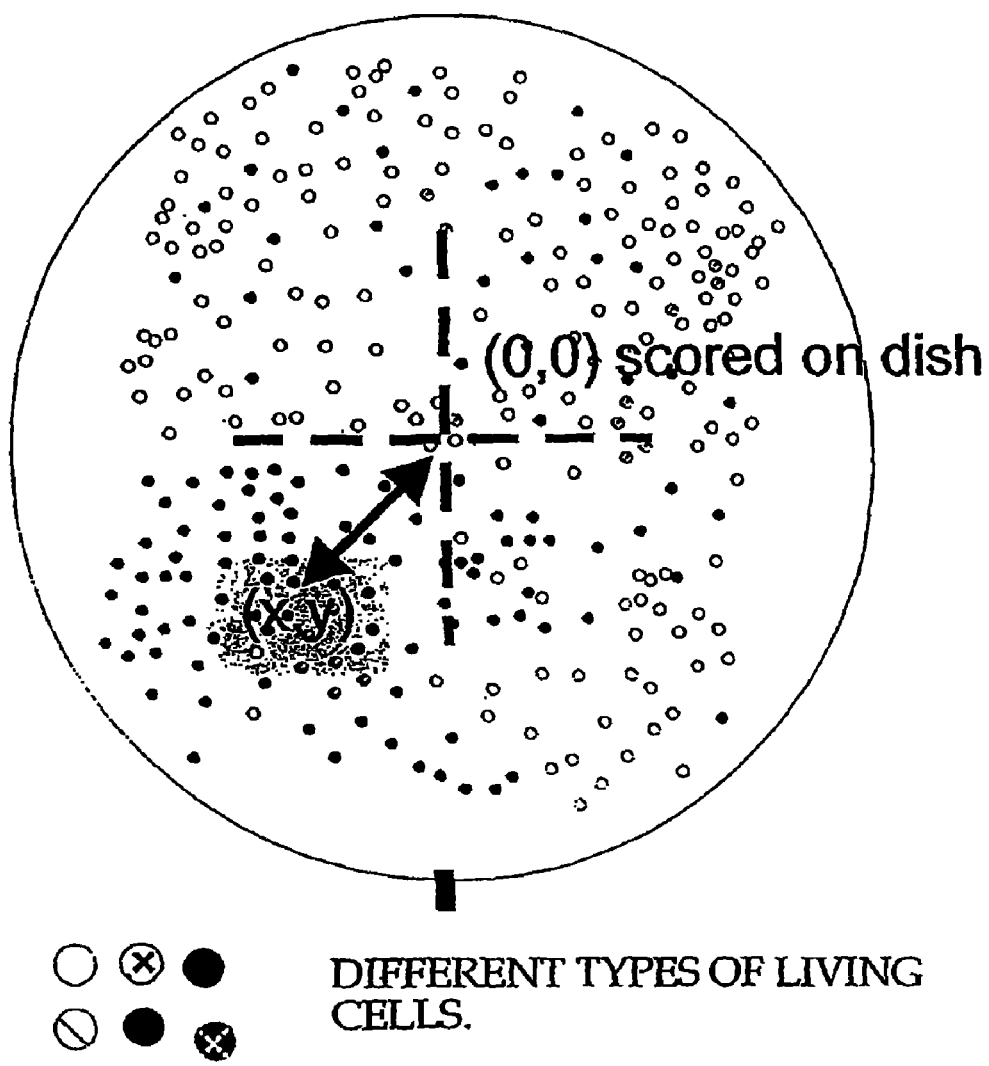
FIG. 17 provides a close-up schematic diagram illustrating the use of an etched culture dish for the purpose of establishing a frame of reference for cell location in the dish.

Thus, in some embodiments of the present invention, the system provides means position relative to an extremely fine grid ("+") that is gently etched into the sterile culture dish using a glazier's microfinish wheel. The dish can then be removed and placed back in the incubator or stored under conditions, as appropriate. When it is time to reimage the cells, the system is calibrated by reference to the "+" on the dish and the (0,0) point of the coordinate is taken to be the center of the "+." The user can easily see the etching under transmitted light for initial positioning. FIG. 17 provides a close-up schematic diagram illustrating the use of an etched culture dish for the purpose of establishing a frame of reference for cell location in the dish. Thus, the goal of annotating each cellular response within the actual physical location of that cell in the dish is met. In addition, the etching facilitates the observation of the same field of cells hours or days later, in order to monitor cell responses to stimuli, etc. over time.

The system used in these experiments references its position relative to an extremely fine grid ("+") that is gently etched into the sterile culture dish using a glazier's microfinish wheel. The dish can then be removed and placed back in the incubator or stored under conditions, as appropriate. When it is time to reimage the cells, the system is calibrated by reference to the "+" on the dish and the (0,0) point of the coordinate is taken to be the center of the "+." The user can easily see the etching under transmitted light for initial positioning. FIG. 17 provides a close-up schematic diagram illustrating the use of an etched culture dish for the purpose of establishing a frame of reference for cell location in the dish. Thus, the goal of annotating each cellular response within the actual physical location of that cell in the dish is met. In addition, the etching facilitates the observation of the same field of cells hours or days later, in order to monitor cell responses to stimuli, etc. over time.

Thus, the present invention not only provides methods and systems to identify and exploit differences between cell types to give a growth advantage to specified cells (i.e., primary breast tumor cells), while giving a growth disadvantage to other cells (i.e., normal mammary epithelial cells), the present invention provides VSOM fluorescence assays that can quantify the proliferation rate of living cells on a cell-by-cell basis.

L. Improvements in In Vitro Drug and Chemosensitivity Testing

In addition to providing improved means to grow and analyze malignant cells, the present invention provides significant improvements in in vitro drug testing and chemosensitivity assays that facilitate patient-directed therapies to improve clinical outcomes for cancer patients (e.g., breast cancer patients).

A summary of clinical correlations can be made using the following nomenclature: TP (true positive, patients whose cells are sensitive in vitro and respond to chemotherapy), TN (true negative, patients whose cells are resistant in vitro and do not respond to chemotherapy), FP (false positive, patients whose cells are resistant in vitro, but resistant clinically), FN (false negative, patients whose cells are resistant in vitro, but respond clinically), PPA (positive predictive accuracy)=TP/ (TP−FP), percentage of patients with sensitivity in the test system and who respond to therapy, and NPA (negative predictive accuracy)=TN/(TN+FN), the percentage of patients with sensitivity in the test and don't respond to therapy.

Data from previous correlations of in vitro test results with patient responses show an overall PPA of 72% and an NPA of 90%. This corresponds to a sensitivity (i.e., the ability to detect clinically responsive patients) of 85%, and a specificity (i.e., the ability to detect unresponsive patients) of 89%. These numbers represent an average of seven different assay types in studies involving 4263 patients, and results were pooled from several individual studies (DeVita, *Cancer: Principles and Practice of Oncology*, Lippincott-Raven, Philadelphia [1997]). These authors suggested that these assays be referred to as "drug-response" assays, rather than "chemotherapy" assays, because they are more successful at predicting patient drug resistance than predicting patient response.

Digital imaging fluorescence microscopy, real-time analysis of digital images, and bioinformatic databases combined into "visual servoing" (VS), a robotic vision technique, refers to the dynamic manipulations of experimental parameters based on analysis of digital image content. In addition, VSOM has the ability to scan back and forth across multiple fields of view and in this way, monitor very large numbers or different populations of living cells.

As discussed above, VSOM further provides the ability to repeatedly return to the same field of cells of interest, in order to monitor the changes on a cell-by-cell basis. This capability facilitates the correlation of early physiological responses observed in cells and the future biological state or ultimate fate of the cells, whether it be proliferation, apoptosis, ar arrest in some stages of the cell cycle. Indeed, one of the embodiments of the present invention provides the most desirable predictive assays. Importantly, these assays are dynamic and adaptive.

In one embodiment, the adaptive VSOM fluorescence assay involves the observations of the cells' early physiological responses to intelligently chosen, computer-controlled stimuli. In some preferred embodiments, these stimuli and perturbations are reversible and do not permanently commit the cell to a given biological path. For example, a particular subpopulation of cells is identified based on an observed stress response as the pH of the extracellular medium is decreased. An intelligent response of the system would be to lower the pH of the medium until the cells of interest were identified and then return the cells to a higher pH before they are irreversibly damaged. The cells of interest are then identified on a cell-by-cell basis, and the system used to conduct additional tests, in order to optimize and/or exploit this differential response to an environment with a low pH.

The present invention also provides the ability to repeatedly probe the cell for physiological characteristics that can be exploited by anti-cancer drugs or combinations of drugs. Thus, in preferred embodiments, the VSOM fluorescence assays of the present invention provide a means for rapid cell identification using a complicated mixture of cells, wherein the fluorescent probe is non-toxic to the cells, cells are identified based on characteristic physiological responses to applied stimuli or perturbations, and the stimuli or perturbations do not have an irreversible effect on the cells. Indeed, in particularly preferred embodiments, the predictive assays of the present invention are dynamic and adaptive VSOM fluorescence assays that involve the observation of a series of early physiological responses to intelligently chosen computer-controlled stimuli. This approach is even more powerful when such stimuli and perturbations are reversible and do not permanently commit the cell to a given biological path. The ability to repeatedly apply relatively innocuous stimuli and perturbations to living cells allows the repeated probing of the cells for the physiological characteristics that can be exploited by anti-cancer drugs or combinations of anti-cancer drugs. The VSOM fluorescence assays of the present invention are highly predictive of cells' future behavior and/or ultimate fate. For example, the present invention provides means to determine whether a cell has been sufficiently stimulated to proliferate or whether it has been stressed to the point where apoptosis is inevitable. This capability assists in making correlations between the early physiological responses observed in cells and the future biological state or ultimate biological fate of the cells (i.e., proliferation, apoptosis, arrest in a particular cell cycle stage, etc.).

Furthermore, the present invention provides an object-oriented database containing records of previously observed physiological cell responses. This database provides a very valuable resource for the implementation of knowledge-based control of VSOM assays. The ability to remotely access this database (i.e., through any VS-enabled microscope) makes these instruments controllable over the Internet and greatly increases their functionality, while greatly decreasing the expense of these instruments and the computer power needed to operate them.

At least three prospective clinical trials have attempted to use in vitro chemosensitivity testing to improve patient chemotherapy response and cancer survival. However, these trials failed to demonstrate increased survival for patients who were administered chemotherapy based on results of in vitro chemosensitivity tests. However, every patient is at least slightly different from every other patient. For example, one patient may have an adverse reaction to a drug, while another patient experiences no side effects. In the case where a patient adversely reacts to a drug or their tumor does not respond to drug, the physician changes the drug and/or treatment regimen in an attempt to identify a drug that will work. In the case of breast cancer, physicians must choose a drug (or more than one drug) from a wide range of possibilities and find the combination that is most effective against each individual patient's tumor and produces the fewest side effects in each individual patient. In many cases, the physician is forced to try a series of drugs with each patient (i.e., these are in vivo drug response tests to determine the optimum treatment regimen). The potential advantage of testing the drug response in vitro is that a wider range of drugs can be tested over a shorter time period, sparing the patient a series of debilitating trial-and-error attempts to find an appropriate treatment. Thus, for over 40 years, attempts have been made to remove tumor cells form the patient's body and test them in vitro.

The two in vitro chemosensitivity assays used in these failed methods were the HTCA (human tumor cloning assay) and the DiSC (differential staining cytotoxicity assay). In these assays, the in vitro cell culture and propagation techniques used and the biological end-points measured differ significantly. The HTCA calls for the culture of minced tumor tissue in very small capillary tubes that are sealed at both ends and then incubated for 14 days. Before this mixture of malignant and non-malignant cells (0.2 to $1.0 \times 10^5$ cells) is sealed in the tubes, the cells are exposed for 1 hour to standard anti-cancer agents at concentrations corresponding to one-tenth the peak plasma concentration observed in humans. The cells are then suspended in 0.3% agar and sealed in 100 µl capillary tubes for 14 days at 37° C., and 7% $CO_2$. After 14 days, the cells are extracted from the tubes and the number of colonies is manually determined, using a microscope. This capillary cloning system was used because fewer tumor cells are initially required and the subsequent outgrowth of colonies with significant numbers of cells is improved.

The DiSC assay is a non-clonogenic assay, where tumor cells are cultured in liquid medium in small polypropylene tubes for 4-6 days, in order to amplify the number of cells available for testing. Drug exposure times range from 1 hour to 4 days, depending upon the drug. In general, drug concentrations are empirically determined and are higher than those used in the HTCA. For example, cells were treated with doxorubicin for 1 hour at 0.04 µg/ml in the HTCA, but for 1 hour at 1.2 µ/ml in the DiSC assay. In the DiSC assay, cell membrane integrity is assessed by staining dead cells in suspension with Fast Green. Acetaldehyde-fixed duck red blood cells (DRBC) are added to the culture as an internal standard and the entire mixture is cytocentrifuged onto a microscope slide, with the living cells appearing clear, while the dead cells and DRBC are stained green. The slides are then counterstained with HE (hematoxylin-eosin) to stain the living cells. The cells are then microscopically identified as tumor or normal cells by a skilled technician. The ratio of living tumor cells compared to DRBC is then determined.

A common set of problems was noted in the data emanating from the trials described above. Both assays are manual and labor-intensive, are dependent upon human judgment for quantitation and often fail to produce any results, because tumor cells from some patients do not grow well in these in vitro systems. For such reasons, clinician perception and acceptance of these assays have been poor. Thus, patient and specimen accrual has been difficult. Nonetheless, these tests have been supplanted by "second generation" tests which are excellent at identifying drugs that have no effect on a patient's tumor cells. Thus, by eliminating some drugs, physicians do not have to consider these drugs when performing in vivo drug response tests in patients. These tests are based on methods that have long been available, although they are labor-intensive. However, the tests are slow, labor-intensive, and subject to human error.

It is possible that the failure of these previous clinical studies to produce dramatic increases in patient response and/or survival may be the result of various factors, including the microenvironment (e.g., the microenvironment favored by tumor cells was not properly simulated in vitro), the physiological responses of individual cells were not closely monitored throughout the assay, and/or the drug concentrations, combinations and exposure times were limited and not scientifically optimized.

However, during the development of the present invention (i.e., a member of the "third generation" of tests), advanced cell culture techniques and innovative technology derived from the fields of robotic vision and digital imaging fluorescence microscopy are contemplated. Visual servoing optical microscopy (VSOM) of the present invention is useful for the rapid discovery, etc., of key physiological characteristics which distinguish malignant and non-malignant cells (e.g., breast epithelial cells [BECs]). As described above, VSOM is capable of the rapid and automated production of in vitro microenvironments that favor the propagation of cells of interest (e.g., tumor cells), as well as the production of in vitro fluorescence assays that predict cell behavior on the basis of early physiological responses to applied stress. Thus, the present invention provides a means to overcome the problems associated with the clinical trials described above, including difficulties in getting tumor cells to grow in vitro, the limited ability to observe cells at intervals during the course of the assay, the limited number of biological endpoints observable per assay, and the lack of automation. The present invention also provides the means to rapidly discover and optimize microenviromental conditions suitable for the successful in vitro propagation and chemosensitivity testing of primary breast tumor cells (e.g., human cells). Moreover, the present invention provides the means to accomplish this goal on a tumor-by-tumor basis.

M. Monitoring of Microenvironmental Parameters

The present invention provides means use of biosensors and associated electronics necessary for on-line monitoring of important microenvironmental parameters useful for VSOM experiments. It is contemplated that sensors used in these experiments are ZABS flow-through sensors suitable for connection in series to perfusion lines. Thus, it is possible to continuously monitor and log several important properties of the media just before reaching the cells. As there is insufficient room to place all of these sensors in the actual cell perfusion chamber in some embodiments of the present invention, due to the presence of the large transmitted light condenser, the temperature probe, and the vacuum aspirator. Thus, the pH, L-lactate or glucose, extracellular calcium, and $pO_2$ of the media are monitored as they are continuously perfused into the microincubation chamber.

In some embodiments, the VSOM methods involve the use of four syringe perfusion pumps under computer control. In addition, the microincubation chamber was modified to firmly mount to the computer-controlled xy scanning stage. A vacuum-powered aspirator removes excess liquid and a temperature probe provides feedback for temperature control.

In various embodiments, electronics packages find use with the present invention. For example, the electronics package "PLUGSYS" finds use in these experiments. PLUGSYS is modular in design and the basic system case has sufficient slots to hold the various amplifier modules necessary for the measurement of pH, L-lactate or glucose, extracellular calcium, $pO_2$, etc. The PLUGSYS case is also compatible with the data acquisition hardware used, which include a PCI A/D converter board for a PC. This equipment provides important, real-time data for VSOM system control and allows for the continuous monitoring and logging of microenvironmental parameters that are important for execution and interpretation of VSOM experiments and associated electronics necessary for on-line monitoring of important microenvironmental parameters used during VSOM experiments.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: VS (visual servoing); VSOM (visual servoing optical microscope/microscopy); ° C. (degrees Centigrade); rpm (revolutions per minute); BSA (bovine serum albumin); $H_2O$ (water); aa (amino acid); bp (base pair); kb (idlobase pair); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); µM (micromolar); U (units); V (volts); MW (molecular weight); s and sec (seconds); min(s) (minute/minutes); hr(s) (hour/hours); $MgCl_2$ (magnesium chloride); NaCl (sodium chloride); $OD_{280}$ (optical density at 280 nm); OD600 (optical density at 600 nm);

$[Ca^{+2}]_{in}$ (intracellular calcium concentration); $[Ca^{+2}]_{ex}$ (extracellular calcium concentration); DOX (doxorubicin); BEC (breast epithelial cell); HMEC (human mammary epithelial cell); MCF-7 (a human breast cancer cell line); MCF-7 WTC (MCF-7 Wild Type Cowan); HTCA (human tumor cloning assay); DiSC (differential staining cytotoxicity); CAM (calcein-AM); DRBC (duck red blood cell); DS (drug sensitive); MDR (multi-drug resistant); EH (ethidium homodimer); MEBM (mammary epithelial cell basal medium); MEGM (mammary epithelial cell growth medium); PBS (phosphate buffered saline); D_PBS (Dulbecco's PBS); FN (false negative); TN (true negative); FP (false positive); TP (true positive); NPA (negative predictive accuracy); PPA (positive predictive accuracy); PMA (phorbol 12-myristate 13-acetate); TRME (tetramethylrhodamine ethyl ester); TG (thapsigargin); FURA-2-PE3 (a calcium sensitive fluorescence dye); H42 (Hoechst 33342); LT-R (Lysotracker-Red); FNA (fine needle aspirate); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); SDS (sodium dodecyl sulfate); Tris (tris(hydroxymethyl)aminomethane); DMSO (dimethyl sulfoxide); w/v (weight to volume); v/v (volume to volume); Amersham (Amersham Life Science, Inc. Arlington Heights, Ill.); ICN (ICN Pharmaceuticals, Inc., Costa Mesa, Calif.); ATCC (American Type Culture Collection, Rockville, Md.); Becton Dickinson (Becton Dickinson Labware, Lincoln Park, N.J.); BioRad (BioRad, Richmond, Calif.); Clonetics (Clonetics, San Diego); Clontech (CLONTECH Laboratories, Palo Alto, Calif.); Molecular Probes (Molecular Probes, Eugene, Oreg.); GIBCO BRL or Gibco BRL (Life Technologies, Inc., Gaithersburg, Md.); Invitrogen (Invitrogen Corp., San Diego, Calif.); New England Biolabs (New England Biolabs, Inc., Beverly, Mass.); Novagen (Novagen, Inc., Madison, Wis.); Pharmacia (Pharmacia, Inc., Piscataway, N.J.); Sigma (Sigma Chemical Co., St. Louis, Mo.); Stratagene (Stratagene Cloning Systems, La Jolla, Calif.); Creative Scientific Methods (Creative Scientific Methods, Inc., www., followed by, cre8ive-sci.com); and Zeiss (Carl Zeiss, Inc., Thornwood, N.Y.).

Example I

Imaging Protocol for Repeatedly Returning to the Same Set of Cells

In these experiments, methods for repeatedly returning to the same set of cells in a culture are described. Using these methods, observations are made possible on one or more sets of living cells in a cell culture dish placed on a moveable microscope stage. Importantly, the dish can then be removed from the stage and placed in an incubator in order to allow the cells to grow, etc. The dish can then be placed on the microscope stage and the same set of cells automatically presented for observation. These steps can be repeated as many times as desired or needed.

In these experiments, responses of a set of cells (500-1000 cells at 10× magnification) can be monitored while various compounds are perfused into the culture dish. A stack of images consisting of a specified number of channels are acquired one or more times at specified intervals for a specified length of time. An editable (text) recipe file specifies the experimental recipe used. For "snapshots," only one image stack is acquired, while for "time-lapse" experiments, a complete stack of images can be acquired at regular intervals. The present invention facilitates the performance of several time-lapse experiments in sequence on the same set of cells before removing the dish, as it is preferable that the user not move the stage nor dish between sequential time-lapse experiments. Following the desired analysis the dish is removed from the microscope stage and placed in the incubator for hours or days, as needed. When the dish is returned to the microscope stage, the cells may be either be alive or dead (e.g., fixed and stained cells). Of course, when dead cells are used, time-lapse experiments are not performed. However, in these experiments, the surrounding fields of cells are also imaged by taking "snapshot" image stacks, in order to verify that the single set of cells repeatedly monitored was representative of many surrounding sets of cells.

In these experiments, the "channel specifier" is designated in the filenames by _0, 1, _2, _3, _4, _5, and _X. The numbers refer to a specific position on the optical filter wheel, and the _X refers to a transmitted light image. The identity of the optical filter at each position in the filter wheel is noted in the header of each image according to wavelength. The type of transmitted light used is not specified. For example, "dc122999dc2.0001.1_0.cs" indicates that the image was acquired with the filter wheel in position "0." Based on the image header, the filter at this position is a 360 nm fluorescence excitation filter. The channel specifier "dc122999dc2.0001.1_X.ics" indicates that the image was acquired by opening the transmitted light shutter. This image may be phase contrast, DIC, bright field, etc. The maximum wavelength identities of the optical filters at each position of the filter wheel used in these experiments are indicated in the editable config text file, described in greater detail below.

The "set of cells" refers to all of the cells visible in a particular field of view in a digital image at a specific magnification. Over the course of hours and days, single living cells may enlarge and divide into two cells, cells may disintegrate, cells may die and float away, and individual living cells may move. The initial location of a set of cells is specified as a location relative to a (0,0) point which is a "+" (crosshairs) symbol physically etched on the surface of the culture dish (e.g., a Petri dish) (See, FIG. 17).

The "stack of images" is the collection of all the specified channels at a single time point. For example, the 7th stack in a time-lapse series of image stacks could read:
    dc12999dc13.0007.1_0.ics
    dc12999dc13.0007.1_1.ics
    dc12999dc13.0007.1_2.ics
    dc12999dc13.0007.1_3.ics
    dc12999dc13.0007.1_3.ics
    dc12999dc13.0007.1_X.ics A "recipe file" is a text file that specifies a protocol that is used. For example, the recipe file includes the following:
    Which fluorescence channels go into a complete image stack
    Exposure time for each channel
    Order in which image channels are acquired
    Interval between acquired image stacks in time-lapse experiments
    Number of stacks to acquire
    Identity of excitation filters at each location in the filter wheel During the implementation of the methods, multiple iterations are possible. For example, a "first iteration" involves a dish of cells that have never been imaged. The (0,0) mark is set on the computer screen, using the crosshairs etched on the culture dish holding the cells. The user searches for a set of cells to observe. In this step, various shutters are opened and closed, the filter wheel is moved to different positions, and the program must keep track of where the user has moved the dish, relative to the (0,0) mark. The user then focuses on the set of cells of interest. The experiments are then conducted, based on the information in the recipe file. This first experiment is typically performed as a time-lapse assay of living cells.

However, in other embodiments, a series of "snapshots" of fixed and stained cells is used. Then, the recipe file is re-edited, without moving the cells or stage (refocusing is allowed) and one or more time-lapse experiments are conducted. The dish containing the cells is then removed and place in the incubator (or other storage location) until needed. In some embodiments involving "snapshots," the user moves the dish so as to observe another set of cells and additional snapshots are taken.

In a "second iteration," a set of cells is re-observed. This set of cells has been imaged and information regarding their location has been stored. First, the culture dish containing cells to be analyzed is positioned on the microscope stage. An initial transmitted light image of the crosshair mark is acquired. The user "clicks" on the (0,0) mark on the screen, and the program is told which set of cells is to be observed. The program moves the field to the (0,0) mark and then to the proper field of cells. The user focuses on the cells and performs the experiment based on information in the edited recipe file. In this step, the user opens shutters and moves the filter wheel in order to focus. The recipe file is the re-edited, without moving the cells or stage (re-focusing is permitted), and one or more additional time-lapse experiments are performed. For snapshot experiments, the field is changed as desired, and as many additional snapshots are taken as desired. At the conclusion of the experimental protocol, the culture dish of cells is removed from the stage and returned to its storage location (e.g., an incubator). For "nth iterations," a set of living cells is repeatedly imaged and information about the cell locations is stored. The sequence of events is similar to the second iteration.

Example 2

Use of VSOM

In this Example, the equipment and other aspects of the VSOM of the present invention are described.

A. VSOM System Optical Platform

In most embodiments, a VSOM system is built around an inverted (i.e., the objective lens points upwards) fluorescence microscope because cell chambers and cell vessels are typically easier to design when the microscope has this geometry. However, cell chambers do exist that can be used with upright microscopes (where the objective lens points downwards). The VSOM of the present invention is suitable for use with such an optical platform. Biological research grade fluorescence microscopes are preferred, where the microscope has sufficient weight to be stable once the camera and microscope peripherals are mounted on the microscope. A standard 10× objective is sufficient for some VSOM experiments. Research grade microscopes, objectives and various peripherals are made by various manufacturers, including Carl Zeiss, Inc (Thornwood, N.Y.), and Nikon USA (Melville, N.Y.). Environmentally controlled cell chambers are manufactured by various manufacturers, including Zeiss, Harvard Apparatus (Holliston, Mass.), and Bioptechs, Inc. (Biological Optical Technologies, Butler, Pa.).

B. VSOM Peripherals

Digital cameras that find use in preferred embodiments of the present invention include those designed for low-light fluorescence microscopy applications (e.g., those manufactured by companies such as Roper Scientific Inc., (Tucson, Ariz.), and Quantitative Imaging Corp. (Burnaby, Canada)). Such cameras come equipped with scientific grade CCDs with 12 bit digitizing capability, and contain a total of approximately 1 million pixels, that are approximately 7 µm×7 µm in size. Such cameras are available with software development kits that include C++ source code and software development kits, or host connectivity kits that can be used to write software that integrates the camera operation with software, optical, electrical, and mechanical elements (i.e., microscope peripherals) on the host PC. These cameras are provided with a variety of industry standard computer interfaces such as PCI computer interface cards, or direct "Firewire" (IEEE 1394) cable connections so that features of the camera are programmable through the host computer.

In addition to digital cameras, other peripherals find use with the present invention, including XY scanning stages, optical filter wheels, coarse z-axis focusing motors, and transmitted and epifluorescence shutters (e.g., peripherals available from manufacturers such as LUDL Electronics Products, Ltd. (Hawthorne, N.Y.)). Various manufacturers provide other equipment. For example, Sutter Instrument Co. (Novato, Calif.) manufactures optical filter wheels and robotic micromanipulators, while syringe pumps are available from: Harvard Apparatus (Holliston, Mass.), and microscope objective nanopositioners (piezoelectric positioner, Physik Intrumente, Waldbronn, Germany). These companies also sell the appropriate programmable controllers for their respective peripherals. Harvard Apparatus also sells PLUG-SYS and similar measuring and controller for the operation and interfacing of various environmental sensors (such as oxygen, lactate, glucose, pH, etc.) with a host computer.

C. Biological Reagents

Biological reagents and fluorescent labels, etc., are available from numerous manufacturers. For example, fluorescent probes for living cells are available from Molecular Probes (Eugene, Oreg.). Other cell culture media, cell propagation and related equipment and supplies are available from standard vendors (e.g., Sigma, Fisher, etc.).

D. VSOM Host Computer

In preferred embodiments of the present invention an industry standard 450 MHz Pentium III class PC, running a version of LINUX or Microsoft Windows, with one or more available PCI slots (depending on whether the digital camera requires a PCI slot for its interface to the host computer), standard serial and parallel ports, an OHCI compliant IEEE1394 port (if required by a FireWire capable digital camera), 256 MB RAM, one or more 18 Gbyte hard drives, a tape backup unit, Ethernet adapter, 32-bit color video card, and High resolution monitor (1280×1024 pixels is preferred) is required. Standard C++ computer programming skills are required to integrate the operation of the digital camera and various microscope peripherals with the software and algorithms discussed above for on-line image segmentation and analysis. Thus, standard C++ programming software, and an integrated software development package such as Microsoft Visual Studio C++ are required. In addition, software packages containing C++ libraries for standard digital image acquisition, peripherals control and automation, and standard image processing, plotting, and display operations are desirable. Such packages include: "SCIL Image" (TNO, Delft, The Netherlands); "MetaFluor," and "Metamorph" (Universal Imaging Corporation, Downingtown, Pa.); and "Component Works++" (National Instruments, Austin Tex.). In addition, standard analog to digital interface cards, such as those made by National Instruments, are in some cases necessary, as the number of microscope peripherals and environmental sensors controlled by the VSOM system increases.

E. Implementation of VSOM

In addition to the optical platform, at least one each of the following are required for minimal implementation of VSOM: a temperature-controlled cell chamber, computer-controlled syringe pump, illumination shutter, and an optical filter wheel. Transmitted light capability is not required for a minimal implementation experiment; only fluorescence microscopy is required. The only microenvironmental control required is a temperature control unit that can maintain temperature at 37 C, with a temperature probe that can be inserted into the specimen vessel. This unit need not be computer-controlled. In minimal implementation experiments, z-control of the objective is not required, assuming the optical platform is relatively stable and vibration-free. An xy positioning stage is not required, because only a single field of cells (not multiple fields) need be observed. However, it is not intended that the present invention be limited to this specific format or design.

In one embodiment, cells are grown in standard plastic petri dishes in a standard cell incubator, prior to the experiment, using standard techniques. In some embodiments, prior to the experiment, the cells are labeled with a nuclear stain suitable for living cells. For example Hoechst 33342 (H42) is used to stain the nucleus of living cells in the following manner. Cells that have been allowed to attach for 24 hrs in the proper size specimen vessel (a round, 35 mm cell culture dish, for example) are exposed to 1.0 µg/mL of H42 for approximately 90 min in a cell incubator. After this exposure, the H42 and any phenol red indicator present in the cell growth medium are washed off and replaced with fresh medium that does not contain phenol red or excessive amounts of fetal bovine serum. The specimen vessel is placed in the cell chamber and the operator brings a suitable field of cells into focus, then directs the image output to a digital camera. One computer-controlled syringe is filled with a suitable solution (such as cell medium without serum or phenol red) that contains no fluorescent probe, and the other syringe is filled with the same solution and a fluorescent probe suitable for living cells. For example, calcein-AM (CAM) is a suitable fluorescent probe that can indicate the existence of multi-drug drug resistance (MDR) in a cell line. In a minimal, VSOM-enabled computer controlled MDR assay, an approximately 1.0 µM solution of CAM is perfused into the cell chamber at approximately 0.5 mL per minute. This compound passes through the membrane of living cells, and then is metabolized, becomes fluorescent, and is retained within the cell. If the cells possesses one or more of MDR proteins, it has the ability to pump CAM out of the cells as is well known to those in the field. In these cases, the cells take up the compound more slowly when CAM is present, and retain CAM less well once it is flushed out of the chamber.

The VSOM system begins the perfusion of the CAM solution, and continuously segments the field of living cells using the blue nuclear fluorescence signal of H42 in the cell nuclei. The contours which delineate the nucleus are thus obtained in the blue channel. These same contours are used in the green channel to calculate the mean fluorescence intensity of CAM in the nuclear region. CAM is often uniformly distributed throughout the cell, so that it is not necessary to detect the cytoplasmic region in addition to the nuclear region. The mean intracellular fluorescence intensity in the green channel (MI) is thus observed in the nuclear region for each individual cell as images are acquired at an appropriate interval (e.g., every 60 s).

A computer algorithm then performs the following servo-loop operations described below in order adjust the amount of CAM in the cell chamber in the following manner. The average MI (as defined above) for all the cells is monitored at each image acquisition point, and then:

a) the syringe containing CAM is shut off, and the syringe without CAM is turned on, when the average MI, for all cells in the field of view, achieves a user defined threshold, b) the syringe without CAM is shut off, when the average MI, for all cells in the field of view, decreases by a user-defined percentage of the maximum average MI previously achieved in (a)

c) end of experiment

In such a minimal experiment, the individual rates of CAM uptake and retention are obtained on cell by cell basis. The system is then able to report, at the end of the experiment, the number (or percentage) of individual cells in the field which exhibited MDR. In addition, such cells are thereby identified and available for subsequent test for compounds which modulate MDR. However, it is not intended that the present invention be limited to this particular system, format, cells, etc. Indeed, the present invention provides maximum flexibility to the user in terms of experimental design.

Example 3

VSOM Experiment

In this Example, a VSOM experiment conducted as described in Example 2 is described, with the indicated modifications.

The optical platform used was a Zeiss Axiovert 135H/DIC, TV inverted microscope equipped for transmitted light (phase and DIC) and multi-color fluorescence microscopy. It was equipped with a computer-controlled xy scanning stage, z-axis stepping motor, and a six-position filter wheel (LUDL Electronic Products, Ltd. Hawthorne, N.Y.). A 12-bit Xillix CCD camera (Xillix Technologies, Vancouver, BC) containing a Kodak KAF-1400 CCD chip (1317×1035 pixels, 7×7 micron pixel size) was used for these studies. This camera has a readout rate of 8 MHz (i.e., approximately four full size images per set). Images from the camera were directly read out into the host computer, which was a Sparcstation Ultra 1, a multi-tasking UNIX workstation.

In addition, a Peltier temperature-controlled microperfusion chamber (PDMI-2 open chamber with TC-202 Biopolar temperature controller, Harvard Apparatus/Medical Systems Research Products, Holliston, Mass.) and a dual-syringe pump (Pump-33, Harvard Apparatus) were used. These syringes do not have to be the same size; each syringe has its own computer-controlled block, so that perfusion rates can be independently controlled. A "bath" type thermistor (BSC-T3, 36K Ohms total) was used with the PDMI-2.

The inverted design of the microscope in some preferred embodiments allowed perfusion of living cells, with immobilized cells imaged from below. An oil-immersion objective finds use in some embodiments of the present invention. Also, in some embodiments, cells are grown in 35 mm Petri dishes, while in other embodiments, cells are grown on circular coverslips, and viewed from below. This inverted microscope configuration allows the user to switch from fluorescence to transmitted light detection (phase or DIC) and verify cell locations and morphology. This is achieved with a computer-controlled transmitted light shutter. A computer-controlled epifluorescence shutter in the filter wheel is also available for use (LUDL). In these experiments, automated visual servoing operation of the system (i.e., control of pumps, illumination shutters, filter wheel, and Xillix camera) was performed by the program "ADR." VSOM experiments that were performed using a preprogrammed recipe were conducted using the program "VX5."

A. ADR Visual Servoing Experiment

MCF-7 WTC cells were grown in 35 mm cell culture dishes, and were pre-stained with H42. After an approximately 1 hr pre-incubation with H42, cells were rinsed with DPBSGP and were placed in the warm microscope chamber. The ADR program successfully operated in the following fashion. Three digital images (360 nm excitation, 490 nm excitation, and transmitted light, brightfield) were acquired at regular specified intervals through this experiment and all the H42 stained nuclei were detected and segmented before the next image interval. The nuclear contours for each nucleus that were delineated in the blue channel were used to calculate a mean cellular fluorescence intensity value from the green channel (MI). An initial perfusion of DBPSGP solution only (syringe #1) was performed at 1.0 mL/min for 8.3 minutes, (as specified by the user), and then syringe #1 was stopped. Next, a perfusion of DBPSGP solution containing 1 µM CAM (syringe #2) was begun at 0.5 mL/min. When the average MI of all the cells reached a specified threshold, syringe #2 was stopped via successful visual servoing. It took 13.9 minutes for the cells to accumulate sufficient CAM, and for the system to detect sufficient intracellular CAM (in the nuclear region), before the system successfully stopped syringe #2, and restarted syringe #1. After 11.4 min (as specified) the system stopped syringe #1 again. It then continued to monitor the cells in chamber (as specified), in the absence of any flow for an additional 24.9 min. It then stopped acquiring images at the end of the experiment.

Example 4

MDR Assay-Test Kit and VSOM Experiment

Figure 11:
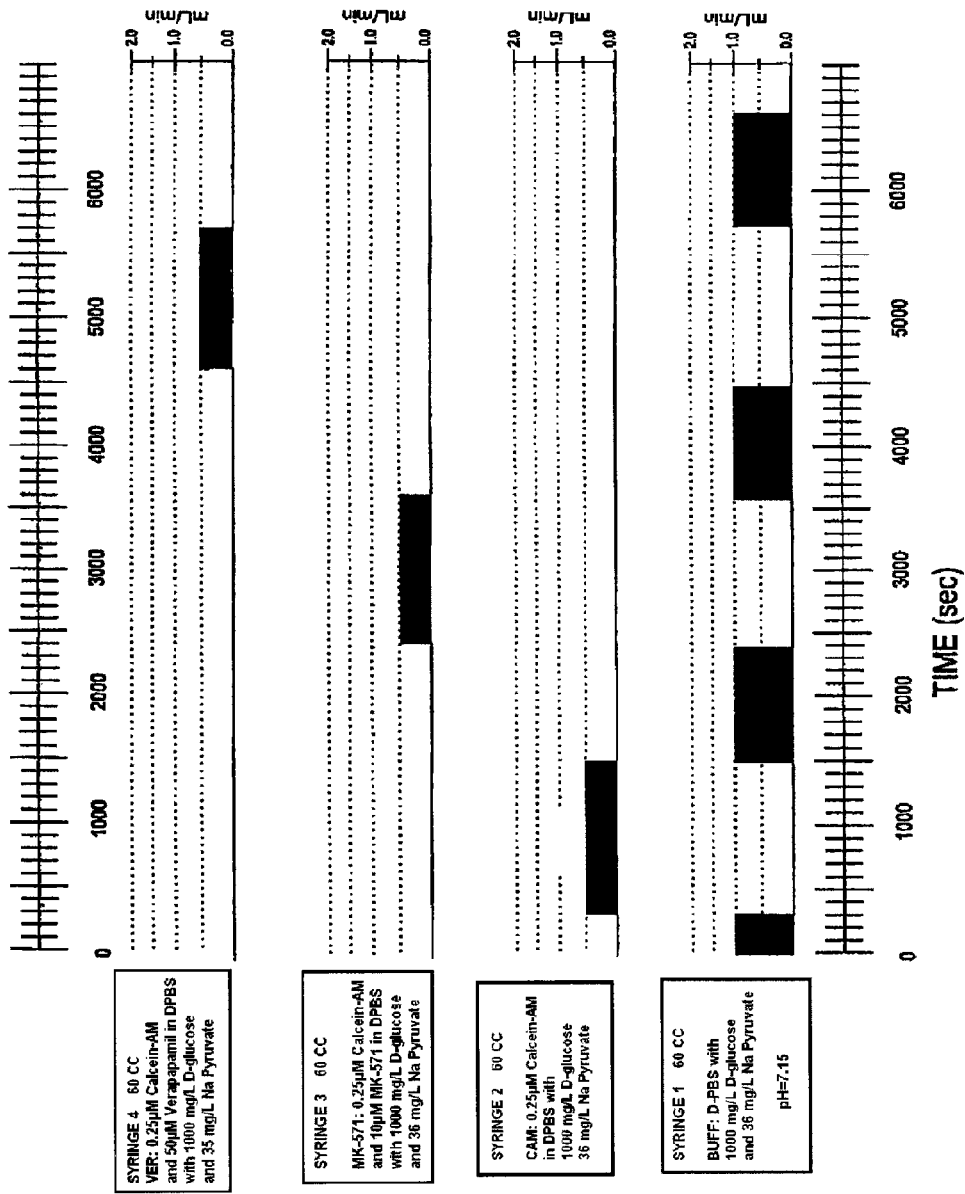
FIG. 11 provides a diagram of detailed information on the syringes, compositions of solutions in the syringes, flow rates, and perfusion intervals used in some VSOM experiments described herein (See, Example 5). Both runs used the pump schedule. After the two runs were performed (one after the other, on the same day), the plot which was displayed on the computer screen was saved. The plots for runs 1 and 2 are shown in black windows at the bottom of the Figure. The red line in each case represents the average of all the cell responses in the entire field of view. As indicated in these two plots recorded for MCF-7 WTC (DS, run 1) and MCF-7 (MDR, run 2), DS cells (upper plot) accumulated more calcein (240±82, N=336), than did the MDR cells (103±80, N=161). This is in agreement with the relative differences in calcein accumulation observed between the same DS and MDR cells in the multi-well plate experiments which represent an average over many cells.

The MDR Assay β-Test kit was also tested in a VSOM experiment, as described herein. FIG. 11 provides a schematic diagram of this VSOM experiment. Pumps are turned on and off at specified flow rates according to a pre-programmed recipe, or based on real-time analysis of individual cell responses. The CAM, V, and MK concentrations used are noted in the figure. The three exposures to CAM were 900 seconds (20 min) each, and thus the total exposure to CAM was 60 min. The black windows at the bottom of the Figure show the mean response of all cells in the field of view. This mean response plot is displayed on the computer screen during the VSOM experiment, and digital images from one or more channels (transmitted light is usually one of the channels displayed) are displayed on the screen as well.

The plot and images were continuously refreshed and updated during the experiment. In the two plots recorded for MCF-7 (DS, run #1) and MCF-7 ADR (MDR, run #2), the DS cells were found to accumulate more calcein (240±82, N=336) than did the MDR cells (103±80, N=161). This is in agreement with the relative differences in calcein accumulation observed between DS and MDR cells in the multiwell plate experiments which represent an average over many cells. However, the mean cellular fluorescence of each cell was monitored during VSOM experiments, and making deviations from the mean easily detectable. For example, several cells began to lose viability and plasma membrane integrity. Such cells are unable to retain calcein, and it leaks out, causing the fluorescence signal to drop. It is possible that this is an effect related to DMSO toxicity. However, an understanding of the mechanisms is not necessary in order to use the present invention and it is not intended that the present invention be limited to any particular mechanism(s). Nonetheless, it should be noted that the current VSOM system is capable of easily terminating the exposure/perfusion as soon as a single cell death is noted.

Figure 12:
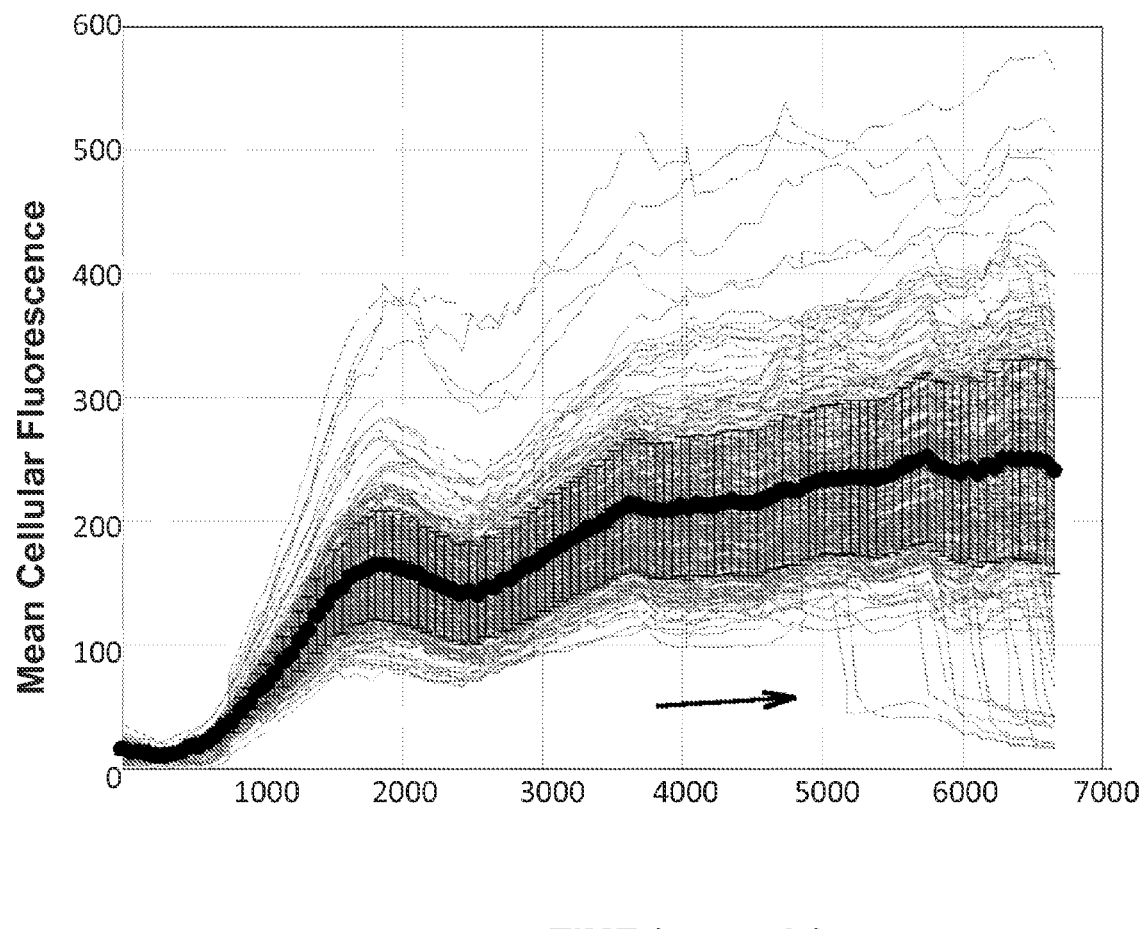
FIG. 12 provides a graph showing the individual cell responses of each DS cell in run 1 of Example 4. The mean response±standard deviation of all the cells is shown overlaid in black. The individual responses are indicated by the individual lines in this graph. During VSOM experiments, the mean cellular fluorescence of each cell was monitored and deviations from the population mean were detected. For example, the arrow indicates several cells that began to lose viability and plasma membrane integrity. Such cells are unable to retain calcein and the fluorescence signal drops.
Figure 13:
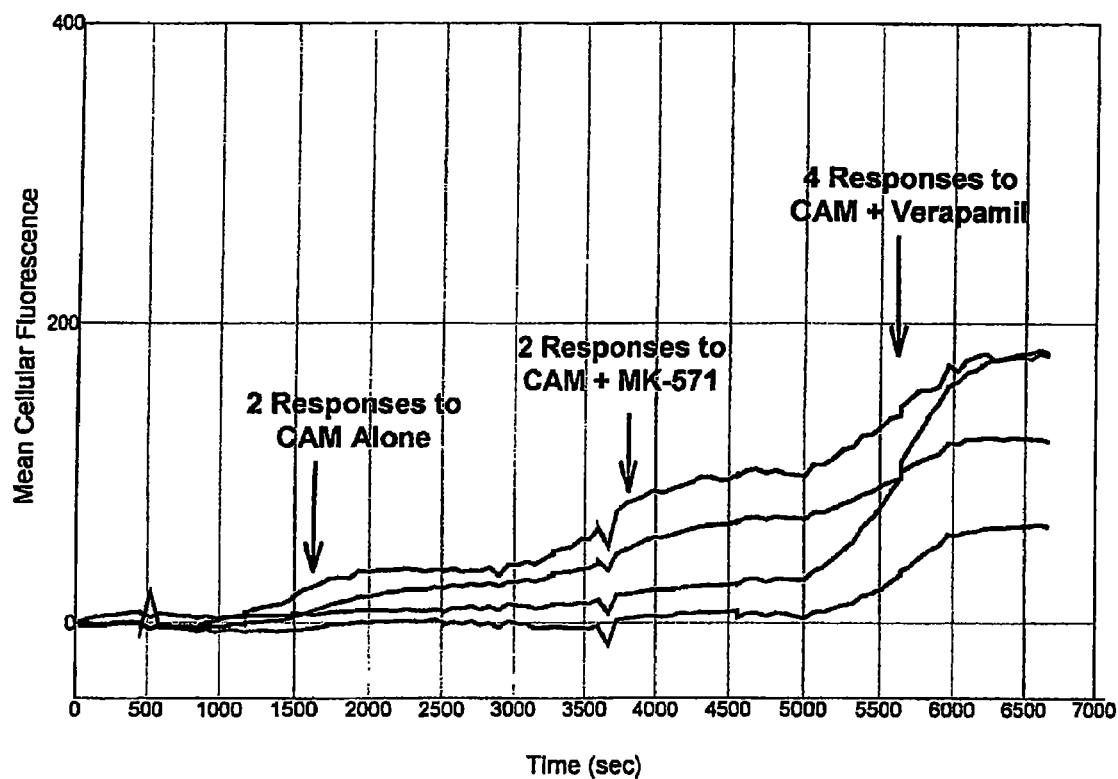
FIG. 13 shows results for selected individual cell responses from four cells in run 2 (Example 4). This is the type of detailed physiological information that flow cytometry and multi-well plate assays cannot provide and it demonstrates that the VSOM technology of the present invention has desirable capabilities. Detailed rate information on calcein accumulation and retention is available throughout the VSOM experiments, as indicated.

FIG. 13 shows four selected single cell responses from run #2, of this Example. These response curves are good examples of the underlying principle of the β-Test kit. In two of the response curves (FIG. 13), the cells do not accumulate calcein until verapamil (V) exposure during the operation of syringe #5 (FIG. 11). Thus, the inference can be made that these cells only express Pgp pumps, because the pumps are not inhibited by MK-571 (MK). It can clearly be seen than none of these cells were present in the DS cell population (FIG. 12). Further, after CAM+V exposure, one of the cells rapidly accumulated calcein until its mean cellular fluorescence fell within one standard deviation of the mean response of cells observed for DS cells (FIG. 12). If the assumption is made that all other factors are the same, the prediction can be made that the second cell contains fewer Pgp molecules. The remaining two curves (FIG. 13) show additional responses during CAM (only) and CAM+MK exposures, requiring additional analysis. The curves observed cannot be explained in terms of the presence or absence of only two pump types, neither having, the ability to extrude internalized calcein. However, an understanding of the mechanism(s) is not necessary in order to use the present invention, and it is not intended that the present invention be limited to any particular mechanism(s). Thus, this is the type of detailed physiological information that flow cytometry assays and multiwell plate assays cannot provide. In contrast, the VSOM technology provided herein has these capabilities.

For example, detailed rate information on calcein accumulation and retention is made available throughout VSOM experiments. For some response curves, the rate of calcein accumulation during the three CAM perfusions can be calculated. In addition, the rate of calcein retention during BUFF perfusions can also be calculated. Calcein accumulation was found to occur in the 1500, 3500, and 5500 second time periods, and plateaus corresponding to excellent calcein retention were observed in the 2500, 4500, 6500 second time intervals. As noted above, some MDR pumps have the ability to extrude calcein after it has been internalized in the cell. The ability of DS cells to extrude internalized calcein is apparent during the 2500 second period (See, FIG. 12), corresponding to BUFF perfusion. However, 2 MDR cells (FIG. 13) do not have this ability.

In addition, using the above teachings the pre-programmed manipulations are suitable for a visual-servoing operation, in which the computer makes decisions.

Example 5

Digital Imaging Fluorescence with Modulating Agents

Using VSOM it is possible to automate digital imaging fluorescence microscope. For example, one can perfuse calcein-AM (CAM, 0.25 µM) containing modulating agents MK-571 (10 µM) or verapamil (50 µM) into a microperfusion chamber. MK-571 is a specific inhibitor of the transmembrane protein MRP, while verapamil inhibits MRP, as well as the transmembrane protein PgP. Both of these transmembrane proteins extrude foreign compounds and it is contemplated that they play a role in multiple-drug resistance. Separate genes encode these two different proteins. The drug cross-resistance profiles (spectra) of these proteins overlap, but are not identical. In addition, as indicated above, these proteins have different sensitivities to various inhibitors.

MCF-7ADR cells labeled with Hoechst 33342 are observed at 35° C. for the mean fluorescence intensity (MI, calcein) per cell. The mean fluorescence intensity per cell (MI, calcein) is calculated in real-time and the software operation of syringe pumps is based on these calculations (i.e., visual servoing). The protocol used in these experiments is based on the MDR Beta-Test Kit (Molecular Probes) described above. Images are acquired during three perfusion intervals: (1) 0-2100 seconds, CAM; (2) 8600-11,000 seconds, CAM+MK-751; and (3) 14,000-16,000 seconds, CAM+verapamil. Typically, all cells respond by the third perfusion interval. Subpopulations expressing MRP and/or PgP are inferred based on responses where MI>200: (a) responses in 1 (no PgP or MK-571), (b) none until 2 (MRP), and (c) none in 1 or 2 (PgP only). During interval 1, no PgP or MK-571 expression was observed, while MRP expression was observed during interval 2. The increase in MI due to calcein accumulation was greater than 200 in 30 cells, due to inhibition of MRP by MK-571.

Example 6

BrdU Proliferation Assay for Living Cells

In this Example, BrdU proliferation assay systems for living cells are described. The power of any VSOM predictive assay is improved if specific cell responses can be correlated with specific biological endpoints. Several fluorescence assays for apoptosis exist, but there are few fluorescence assays for living cells that can measure important parameters, such as BrdU incorporation, which can be used to quantify DNA synthesis or cell proliferation. In these experiments, an imaging ratioing technique was developed to detect the proliferation state of living cells by quantifying the amount of BrdU incorporation. The protocol for this assay was adapted from the published protocol of Dr. Paul Yaswen (Stampfer, et al., Exp. Cell Res., 208:175-188 [1993]). The same cell lines and media were used. However, for DNA synthesis assays, 5-bromo-2'-deoxy uridine (BrdU) was substituted for [$^3$H]-thymidine. These experiments were performed using a 5-bromo-2'-deoxy uridine labeling and detection kit (No. 1296736, Boehringer Mannheim). Thus, after a VSOM experiment, the cells were fixed and the VSOM results verified based on digital image ratioing, using traditional indirect immunofluorescence assays.

Cells that have been stimulated to grow (proliferate) synthesize twice their normal complement of DNA in preparation for cell division. These actively growing cells can take the nucleotides A, T, C, and G from the extracellular media and use them to construct DNA. However, when BrdU is present, it is used instead of T to synthesize DNA. Thus, during exposure of a population of cells to BrdU for a short period (e.g., 1 h), the subpopulation of cells that were synthesizing DNA during that 1 h period will incorporate the most BrdU into their nuclear DNA. This is referred to as a "pulse-labeling" experiment. The goal of this experiment was to determine whether the ratio of Hoechst 33342 (H42) and Syto 16 (S16) fluorescence emission intensities is useful for determining the amount of BrdU incorporation on a cell-by-cell basis.

H42 and S16 stain the nuclei of living or fixed cells. H42 fluorescence emission is quenched (reduced) if the DNA contains incorporated BrdU. However, the fluorescence emission of S16 is not affected by the presence of incorporated BrdU. Thus, the ratio of H42/S16 fluorescence intensities (calculated on a pixel by pixel basis using digital images) should be proportional to the amount of BrdU incorporated into each cell's DNA.

In order to determine this, three dishes of 184B5 cells were used in these experiments. For the first 48 hrs, two dishes received serum-free formulations of MEBM (Mammary Epithelial Cell Basal Medium, CC-3151, Clonetics) while the third dish received serum-free MEGM (Mammary Epithelial Cell Growth Media, MEGM, CC-3051, Clonetics). MEGM contains bovine pituitary extract (BPE), hydrocortisone, human epidermal growth factor (EGF), and insulin, while MEBM does not. Thus, for the first 48 hrs, Dish 3 received all the factors commonly required for propagation, while Dishes 1 and 2 did not. MEBM only supports cells at a basal level of metabolism and is not intended to support cell attachment or propagation. After 48 hrs, Dish 2 was refed with MEGM (this two step process is referred to as 'MEBM+EGF"), Dish 3 was also refed with MEGM, but Dish 1 received MEGM-hEGF (BPE, hydrocortisone, and insulin were present). The Dish 1 treatment is referred to as 'MEBM–EGF."

As indicated in FIG. 4 of Stampfer et al., for 184B5 cells, DNA synthesis reaches a peak approximately 18 hrs after feeding, with MEGM cells showing the greatest amount of DNA synthesis, followed by MEBM+EGF cells which showed decreased DNA synthesis. Cells maintained in MEBM–EGF showed little DNA synthesis. These results were obtained using [$^3$H]-thymidine. In the experiments conducted during the development of the present invention, pulse-labeling with BrdU was performed for 1 hr, and then the living cells were dual-stained with H42 and S16. One digital image was acquired of cells with 360 nm excitation (H42 signal), and a second was acquired at 490 nm excitation (S16 signal). These images were processed and ratioed on a pixel by pixel basis. The resulting ratio values were then color coded for ease in analysis. These results agreed with those obtained by traditional [$^3$H]-thymidine incorporation assays. MEGM cells (Dish 3) showed the greatest degree of BrdU incorporation, followed by MEBM+EGF cells (Dish 2), with MEBM–EGF cells (Dish 1) showing little BrdU incorporation.

To further verify these observations, the cells were fixed with 70% ethanol and 50 mM glycine, pH 2.0, at –30EC, and indirect immunofluorescence staining was performed. After this staining, cells were restained with H42 and S16 to determine whether fixed cells labeled with the anti-BrdU antibody also had low H42 fluorescence, indicative of BrdU quenching. Indeed, there was some evidence of this effect. The MEGM cells exhibited the greatest amount of BrdU staining. Examination of the same in the blue channel indicate the general trend that cells that stain for BrdU exhibit lower H42 fluorescence signals. There are two ways to quantify BrdU incorporation. The first is anti-BrdU antibody detection, represented by the intensity of red fluorescence. The second is the calculation of the ratio of blue nuclear fluorescence intensity (H42) divided by green nuclear fluorescence intensity (S16) on a pixel by pixel bases (i.e., image ratioing). As H42 is quenched by BrdU incorporation and S16 is not, the nuclei that appear red should exhibit lower H42 fluorescence in the blue channel.

Example 7

Imaging of mRNA Transcripts

In this Example, experiments that demonstrate the strengths of VSOM experiments are presented. It is contemplated that such experiments will provide means to image mRNA transcripts in real time in tissue culture as an aid in the development of anti-sense compounds, delivery systems, and signal amplification methods. Experiments to provide radiolabeled anti-sense compounds suitable for real-time medical imaging are also described.

In these VSOM experiments, the human breast cancer cell line, BT-474, is used as a model system, along with mRNA encoding the bcl-2 protein. Fluorescently labeled antisense compounds within individual living cells are tracked, guided to the appropriate target mRNA in the cell, and the is determination made whether individual cells are affected in the manner predicted. Digital imaging fluorescence microscopy, novel computational techniques and bioinformatic tools are used in these compounds to track the fluorescent anti-sense compounds in one channel, while other cell responses (e.g., apoptosis) are monitored in another channel. The expression of bcl-2 at the mRNA level as a function of time, external cell stress, and anti-sense compound structure is imaged. These observations are correlated with bcl-2 protein levels in each cell and the ultimate fate of each cell. Thus, these experiments provide detailed information on the biophysical properties of specific anti-sense compounds useful for the intelligent design of anti-sense compounds for imaging gene expression with PET. Indeed, the in vitro technology of the present invention allows for the testing of more modifications of compounds than is possible in in vivo studies (e.g., in nude mice bearing BT-474 tumor xenografts).

In some experiments, AS-ODN (antisense oligodeoxyribonucleotides) compounds of the same sequence, but with modifications at the 5' terminus are used, so as to allow both VSOM experiments and in vivo PET imaging studies. In the case of VSOM experiments, a fluorochrome is used, while for PET imaging studies, one of two radiofluorinated moieties is used. In both cases, a hexyl-amine linker is attached to the 5'-terminus, to facilitate attachment of the fluorochrome and radiolabel. In additional experiments, liposomes and immunoliposomes s are provided as delivery vehicles. For some experiments, the biological endpoints are based on non-fluorescent, non-radioactive versions of the fluorinated moiety used in radiolabel studies. In this manner, the consequences of different substituents at the 5' terminus of the AS-ODN are determined. In addition, the amount of signal amplification produced in a β-galactosidase protocol finds use with the present invention. In other embodiment, peptide nucleic acids are used. Peptide nucleic acid (PNA) is a modified oligonucleotide in which the entire deoxyribose backbone has been replaced with a polyamide (peptide) chain (Gewirtz et al., Blood 92:36 [1998]; and Temsamani and Guinot, Biotechnol. Appl. Biochem., 26:65-71 [1997]).

In one embodiment, the ASD-ODN sequences used are:

```
1. PT-G3139: TCTC CCAG CGTG CGCC AT   (SEQ ID NO: 1)

2. PNA-1: CCCC AGCC CCTA CCC          (SEQ ID NO: 2)

3. PNA-4: AGCG TGCG CCAT CCC          (SEQ ID NO: 3)
```

The full phosphorothioate of the 18-mer shown in SEQ ID NO:1, with sequence anti-sense to the first six codons of the open reading frame of bcl-2 has shown efficacy against the DoHH2 lymphoma implanted in severe immunodeficient mice (Raynaud et al., [1997]). The two 15-mer PNA-ODNs (peptide nucleic acid oligodeoxyribonucleotide) (SEQ ID NOS:2 and 3) have been evaluated in vitro in a cell-free system (Mologni et al., [1999]). Of particular interest is the fact that a complete block of mRNA translation is only achieved when both PNA-ODNs are simultaneously present.

Fluorescence-labeled PT-G3139, PNA-1 and PNA-4 are obtained from commercial sources (e.g., Genset, http://, followed by, www., followed by, gensetoligos.com). Modifications of these AS-ODNs in which the backbone consists entirely of PD (phosphodiester), PT (phosphorothioate), MP (methylphosphonate) or PNA backbone linkages are also used, as well as compounds with various permutations and mixtures of backbone linkages.

Initial experiments are performed and recorded in the database as a series of single-cell responses. A set of fluorescently labeled AS-ODNs with various modifications of the backbone linkages described above are used. A set of baseline VSOM runs is performed. In these runs, cells are grown on microscope coverslips, and a 63×NA 1.3, oil-immersion objective is used to observe the cells. Cells are placed in a temperature-controlled microperfusion chamber. Initial segmentation of the cytoplasmic, nucleoplasmic and mitochondrial compartments is performed as described above.

A computer-controlled syringe pump injects the fluorescent compound TMRE (tetramethyl rhodamine ethyl ester; Molecular Probes) in a Dulbecco's phosphate-buffer saline (D-PBS) containing calcium, magnesium, glucose, and pyruvate into the cell chamber. The compound TMRE is a cationic redistribution dye used to determine the mitochondrial membrane potential according to the Nerst equation (Farkas et al., supra). Unlike the mitochondrial dye rhodamine 123, TMRE equilibrates rapidly and reversibly into the mitochondria and to a lesser extent, the cytoplasm. It does not stain the nucleoplasmic compartment.

Next, TMRE is flushed out of the cells using a computer-controlled syringe containing only buffer. TMRE is readily rinsed out of the cell. Fluorescently-labeled AS-ODN is then injected into the microperfusion chamber using another computer-controlled syringe. The concentration at which the fluorescent signal from the AS-ODN becomes visible is noted and the AS-ODN perfusion automatically stopped. This represents the completion of the first half of a VSOM run.

All digital images are added to the database, in order to permit replay to verify VSOM operation. Thus, multi-channel digital images, experimental parameters, and single cell responses (5-10 cells at 63×) to computer-controlled compound perfusions become part of the database.

The second half of the initial VSOM runs involve the comparison of the fluorescence distribution pattern of the fluorescently labeled AS-ODN with either previously observed fluorescence distribution patterns obtained for the same cell type, using organelle-specific fluorescence dyes (Molecular Probes), or the existing fluorescence pattern in a separate fluorescence channel for the current cells, dual-stained with both fluorescent AS-ODN and an organelle-specific fluorescence dye. After the VSOM makes a determination of the AS-ODN location within the cell, it applies the appropriate compound from the appropriate syringe and observes the effects on the AS-ODN distribution within the cell.

In the case of lysosomal sequestration of fluorescently labeled AS-ODN, compounds known to selectively permeabilize lysosomes are perfused into the chamber at a controlled rate by the computer-controlled perfusion pumps. Several compounds, such as the sodium proton ionophore monensin have been demonstrated to free fluorescent compounds trapped in the acidic vesicles of human breast cancer cells (See, Schindler et al., [1996]). The amount of monensin (for example) required to free fluorescently labeled AS-ODNs is logged into the database. The time for redistribution to the next compartment (e.g., the nucleus) and the resulting pattern of staining in the nucleus are also recorded.

VSOM perturbations to dislodge AS-ODNs from the nucleus are performed using "clamping" techniques known in the art. These techniques allow the user to vary the concentration of intracellular ions (e.g., potassium) by simply varying the potassium concentration of the surrounding extracellular medium (Negulescu et al., supra). These same methods can be used to alter levels of intracellular calcium. The VSOM system ramps up the concentrations of such ions within the cells in order to interfere with the binding of AS-ODN to basic nuclear proteins. Once again, the concentrations and other environmental conditions necessary to dislodge the compounds from the nuclear environment are recorded. In cases where this method is unsuccessful, on-line hypotonic lysis of cells is performed and harsher environmental conditions applied in subsequent experiments.

In some embodiments, VSOM perturbations to dislodge cytoplasmic membrane-associated AS-ODNs consist of buffer rinses at non-physiological pH or rinses with buffer containing trypsin. Once again, quantitative data on the magnitude of perturbation required to free the fluorescently labeled AS-ODN are recorded on a cell-by-cell basis and correlated with the chemical structure of the current AS-ODN.

In preferred embodiments, the physiological effects of the AS-ODNs (both fluorescent and non-fluorescent) are assessed in several ways. In most cases, an apoptosis-inducing extracellular stress (e.g., UV light, anti-cancer drugs, calcium ionophores, etc.) is applied. In cases where the AS-ODN successfully reduces the amount of bcl-2 protein in BT-474 cells, decreases in bcl-2 protein and these cells' ability to resist apoptosis are observed. The most direct method involves fixing the cells after the VSOM experiments, indirect immunofluorescence analysis using an antibody directed against the bcl-2 protein, followed by a return to the same field of cells to quantify the amount of bcl-2 protein (this is proportional to the observed fluorescence signal on a cell-by-cell basis). However, it is not intended that the present invention be limited to this particular set of steps, as those in the art recognize that other methods are also suitable for use in conjunction with the present invention.

Many other markers for apoptosis known in the art find use with the present invention. These methods include morphological and fluorescent assay systems. For examples, one of the channels collected during VSOM experiments is the transmitted light channel, through which membrane blebbing can be observed. There are also a variety of antibodies to proteins (e.g., annexin V) and DNA stains which reveal the nuclear fragmentation characteristic of apoptosis. In addition, cytoplasmic membrane integrity (e.g., cell viability) stains such as calcein-AM is suitable for use in one of the fluorescence channels during VSOM experiments. In addition, the loss of mitochondrial membrane potential that occurs early in apoptosis is useful as an indicator of apoptosis, as described in greater detail above for LDS-751 stained 185b5 cells.

From the above it should be clear that the present invention provides improved methods and systems for the knowledge-based discovery and optimization of differences between cell types. In particular, the present invention provides visual servoing optical microscopy, as well as analysis methods. The present invention provides means for the close monitoring of hundreds of individual, living cells over time; quantification of dynamic physiological responses in multiple channels; real-time digital image segmentation and analysis; intelligent, repetitive computer-applied cell stress and cell stimulation; and the ability to return to the same field of cells for long-term studies and observation. The present invention further provides means to optimize culture conditions for specific subpopulations of cells.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in relevant fields are intended to be within the scope of the following claims.

The invention claimed is:

1. An automated method for recording cellular responses in a living cell population, said method comprising:
   A. providing a computer, living cells, and a detection device, wherein said detection device is configured to monitor said living cells and obtain cellular image data;
   B. obtaining a first set of cellular image data from said living cells;
   C. automatically communicating said first set of cellular image data to said computer;
   D. defining said first set of cellular image data with said computer, wherein said defining comprises at least one analysis selected from the group consisting of analyzing the morphometry of said living cells, analyzing the subcellular components of said living cells, analyzing the color of said living cells, and analyzing the motion of said living cells;
   E. automatically stimulating said living cells to evoke a cellular response;
   F. obtaining a responsive set of cellular image data from said living cells with said detection device upon evocation of said cellular response;
   G. automatically communicating said responsive set of cellular image data to said computer;
   H. defining said responsive set of cellular image data with said computer, wherein said defining comprises at least one analysis selected from the group consisting of analyzing the morphometry of said living cells, analyzing the subcellular components of said living cells, analyzing the color of said living cells, and analyzing the motion of said living cells;
   I. automatically identifying a first set of differences between said defined first set of cellular image data and said defined responsive set of cellular image data, wherein said automatically identifying differences comprises identifying differences between
      i) said defined first set of cellular image data and/or said defined responsive set of cellular image data, and
      ii) a database of defined cellular image data, wherein said database of defined cellular image data comprises one or more of
         a) identified sets of differences between sets of defined cellular image data, and
         b) additional defined data that facilitates the performance of visual-servoing optical microscopy;
   J. generating a signal from said computer in response to said identified first set of differences;
   K. independently automatically actuating in response to said signal one or more stimulating devices configured to interact with said living cells;
   L. obtaining a second responsive set of cellular image data from said living cells following said independent automatic actuating of said one or more stimulating devices;
   M. automatically communicating said second responsive set of cellular image data to said computer;
   N. defining said second responsive set of cellular image data with said computer, wherein said defining comprises at least one analysis selected from the group consisting of analyzing the morphometry of said living cells, analyzing the subcellular components of said living cells, analyzing the color of said living cells, and analyzing the motion of said living cells;
   O. automatically identifying a second set of differences between said defined first set of cellular image data, said defined responsive set of cellular image data, and said defined second responsive set of cellular image data, wherein said automatically identifying differences comprises identifying differences between
      i) said defined second set of cellular image data and/or said defined responsive set of cellular image data, and
      ii) a database of defined cellular image data, wherein said database of defined cellular image data comprises one or more of
         a) identified sets of differences between sets of defined cellular image data, and
         b) additional defined data that facilitates the performance of visual-servoing optical microscopy;
   P. generating a second signal from said computer in response to said identified second set of differences;
   Q. independently automatically actuating in response to said second signal said one or more stimulating devices configured to interact with said living cells; and
   R. obtaining a third responsive set of cellular image data from said living cells with said detection device upon evocation of said third cellular response.

2. The method of claim 1, wherein said database of defined cellular image data is comprised of machine-readable data.

3. The method of claim 1, wherein said automatically stimulating said living cells to evoke a cellular response is performed by said one or more stimulating devices configured to interact with said living cells.

4. The method of claim 1, wherein said automatically stimulating comprises one or more actions specified prior to obtaining said first set of cellular image data.

5. The method of claim 1, wherein said independently automatically stimulating comprises one or more actions not specified prior to obtaining said a first set of cellular image data.

6. The method of claim 1, wherein said living cell population can be repeatedly mounted and dismounted from the detection device.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Homo sapiens

<400> SEQUENCE: 1
tctcccagcg tgcgccat                                         18

<210> SEQ ID NO 2
<211> LENGTH: 15
<212> TYPE: DNA
<213> ORGANISM: Homo sapiens

<400> SEQUENCE: 2
ccccagcccc taccc                                            15

<210> SEQ ID NO 3
<211> LENGTH: 15

```
<212> TYPE: DNA
<213> ORGANISM: Homo sapiens

<400> SEQUENCE: 3
agcgtgcgcc atccc                                                        15
```